US012342718B2

(12) United States Patent
Parham et al.

(10) Patent No.: US 12,342,718 B2
(45) Date of Patent: Jun. 24, 2025

(54) MATERIALS FOR ELECTRONIC DEVICES

(71) Applicant: Merck Patent GmbH, Darmstadt (DE)

(72) Inventors: Amir Hossain Parham, Darmstadt (DE); Christian Ehrenreich, Darmstadt (DE); Jens Engelhart, Darmstadt (DE)

(73) Assignee: MERCK KGAA, Darmstadt (DE)

( * ) Notice: Subject to any disclaimer, the term of this patent is extended or adjusted under 35 U.S.C. 154(b) by 78 days.

(21) Appl. No.: 17/912,872

(22) PCT Filed: Mar. 22, 2021

(86) PCT No.: PCT/EP2021/057202
§ 371 (c)(1),
(2) Date: Sep. 20, 2022

(87) PCT Pub. No.: WO2021/191117
PCT Pub. Date: Sep. 30, 2021

(65) Prior Publication Data
US 2023/0371372 A1 Nov. 16, 2023

(30) Foreign Application Priority Data

Mar. 24, 2020 (EP) .................................... 20165094

(51) Int. Cl.
| | | |
|---|---|---|
| H10K 85/60 | (2023.01) |
| C07D 471/04 | (2006.01) |
| C07D 487/04 | (2006.01) |
| C07D 495/14 | (2006.01) |
| C09K 11/06 | (2006.01) |
| H10K 50/12 | (2023.01) |

(52) U.S. Cl.
CPC ....... *H10K 85/6572* (2023.02); *C07D 471/04* (2013.01); *C07D 487/04* (2013.01); *C07D 495/14* (2013.01); *C09K 11/06* (2013.01); *H10K 85/622* (2023.02); *H10K 85/624* (2023.02); *H10K 85/633* (2023.02); *H10K 85/636* (2023.02); *H10K 85/654* (2023.02); *H10K 85/657* (2023.02); *H10K 85/6574* (2023.02); *H10K 85/6576* (2023.02); *C09K 2211/1018* (2013.01); *H10K 50/12* (2023.02); *H10K 85/615* (2023.02)

(58) Field of Classification Search
CPC .. C07D 471/04; C07D 487/04; C07D 495/14; H10K 50/11; H10K 50/16; H10K 50/18; H10K 85/633; H10K 85/636; H10K 85/654; H10K 85/6572; H10K 85/6574; H10K 2101/10; H10K 2101/90; C09K 11/06
USPC ................................................ 252/500, 510
See application file for complete search history.

(56) References Cited

U.S. PATENT DOCUMENTS

2016/0372681 A1* 12/2016 Parham ................. H10K 85/657
2018/0114641 A1* 4/2018 Lazarev .................... H01G 4/08

FOREIGN PATENT DOCUMENTS

| | | | |
|---|---|---|---|
| CN | 104024371 A | 9/2014 |
| CN | 105593228 A | 5/2016 |
| WO | WO-2009037565 A2 * | 3/2009 | ......... G02F 1/13363 |
| WO | 2012/064618 A1 | 5/2012 |
| WO | 2013/064206 A1 | 5/2013 |
| WO | 2015/000542 A1 | 1/2015 |
| WO | 2015/172558 A1 | 11/2015 |
| WO | 2016/073522 A1 | 5/2016 |
| WO | 2016/138310 A1 | 9/2016 |

OTHER PUBLICATIONS

Ram "Synthesis of angular annulated heteroaromatic quinazolino[3,2-a]quinazolines." Liebigs Annalen der Chemie / Liebigs Ann. Chem., 7, pp. 701-702. (Year: 1990).*
Abdel-Rehman, Taha M., "Heterocyclic Compounds from 4H-3,1-Benzoxazin-4-one Derivatives as Anticancer Agent", Journal of Heterocyclic Chemistry, vol. 42, Issue 7, Nov. 2005, pp. 1257-1265.
Bergman et al., "Oxidative Ring Expansion of Spirocyclic Oxindole Derivatives," The Journal of Organic Chemistry, vol. 79, No. 19, Sep. 4, 2014, pp. 9065-9073.
El-Hashash et al., "Regiospecific Isomerization of 2-Benzoxazinon-2-yl Benzoic Acid Toward Some Nitrogen Nucleophiles as Environmental Insecticide," Journal of Heterocyclic Chemistry, vol. 54, Issue 6, Nov. 2017, pp. 3716-3724.
El-Hashash et al., "Ultrasonic Aptitude of Regioselective Reaction of 6-bromo-spiro-3,1-benzoxazinone2,1'-isobenzofuran-3',4-dione Towards Some Electrophilic and Nucleophilic Reagents", Journal of Heterocyclic Chemistry, vol. 55, Issue 9, Sep. 2018, pp. 2090-2098.
International Search Report and Written Opinion received for PCT Patent Application No. PCT/EP2021/057202, mailed on May 31, 2021, 15 pages (3 pages of English Translation and 12 pages of Original Document).
Liu et al., "Copper-Catalyzed Domino Synthesis of Isoquinolino[2,3-a]quinazolinones," Advanced Synthesis Catalysis, vol. 354, Issue 8, May 21, 2012, pp. 1579-1584.
Mahmoud et al., "Synthesis and antitumor evaluation of novel tetrahydrobenzo[4',5']thieno[40',2':5,6]pyrimido[1,2-b]isoquinoline derivatives", Synthetic Communications, vol. 48, No. 4, Jan. 8, 2018, pp. 428-438.
Molina et al., "New Methodology for the Preparation of Quinazoline Derivatives via Tandem AZA-Wittig/Heterocumulene-Mediated Annulation. Synthesis of 4(3H)-Quinazolinones, Benzimidazo[1,2-c]Quinazolines, Quinazolino[3,2-a]Quinazolines and Benzothiazolo[3,2-C]Quinazolines," Tetrahedon, vol. 45, No. 13, Apr. 7, 1989, pp. 4263-4286.
Nassar, I. F., "Synthesis of Some Quinazolines Derived From 6,8-Dibromo2-(2-Carboxy-Phenyl)-4H-3,1-Benzoxazin-4-One as Antimicrobial Agents," Chemistry of Heterocyclic Compounds, vol. 45, No. 12, Dec. 4, 2009, pp. 1515-1522.

(Continued)

*Primary Examiner* — Tri V Nguyen
(74) *Attorney, Agent, or Firm* — Faegre Drinker Biddle & Reath LLP

(57) ABSTRACT

The application relates to heterocyclic compounds of formulae (IV) to (VII), to the use of said compounds in an electronic device, and to methods for producing said compounds.

10 Claims, No Drawings

(56) References Cited

OTHER PUBLICATIONS

Pestellini et al., "Anti-inflammatory and antalgic activity of fused ring polycyclic compounds: 2, 10-dioxo-pyridazino(3, 2-b) quinazolines," European Journal of Medicinal Chemistry, vol. 3, 1978, pp. 296-296.
Zeng et al., "One-Step Synthesis of Quinazolino[3,2-a]quinazolinones via Palladium-Catalyzed Domino Addition/Carboxamidation Reactions," Organic Letters, vol. 12, No. 16, Jun. 21, 2010, pp. 3642-3644.
International Preliminary Report on Patentability received for PCT Patent Application No. PCT/EP2021/057202, mailed on Sep. 22, 2022, 13 pages (7 pages of English Translation and 6 pages of Original Document).
STN Reg Database, STN data platform, Case RN. 683779-66-0, pp. 1-23.

* cited by examiner

MATERIALS FOR ELECTRONIC DEVICES

CROSS-REFERENCE TO RELATED APPLICATIONS

This application is a national stage application (under 35 U.S.C. § 371) of PCT/EP2021/057202, filed Mar. 22, 2021, which claims benefit of European Application No. 20165094.2, filed Mar. 24, 2020, both of which are incorporated herein by reference in their entirety.

The present invention relates to materials for use in electronic devices and to electronic devices comprising these materials.

Electronic devices in the context of this application are understood to mean what are called organic electronic devices, which comprise organic semiconductor materials as functional materials. More particularly, these are understood to mean OLEDs (organic electroluminescent devices). The term OLEDs is understood to mean electronic devices which have one or more layers comprising organic compounds and emit light on application of electrical voltage. The construction and general principle of function of OLEDs are known to those skilled in the art.

Emitting materials used in OLEDs are frequently phosphorescent organometallic complexes. In general terms, there is still a need for improvement in OLEDs, especially also in OLEDs which exhibit triplet emission (phosphorescence), for example with regard to efficiency, operating voltage and lifetime. The properties of phosphorescent OLEDs are not just determined by the triplet emitters used. More particularly, the other materials used, such as matrix materials, are also of particular significance here. Improvements to these materials can thus also lead to improvements in the OLED properties. An example of a known class of materials that are used as matrix materials for triplet emitters in OLEDs is that of aromatic isoquinolines.

It is an object of the present invention to provide compounds which are suitable for use in an OLED, especially as matrix material for phosphorescent emitters or as electron transport material, and which lead to improved properties therein.

It has been found that, surprisingly, this object is achieved by particular compounds described in detail hereinafter that are of good suitability for use in OLEDs. These OLEDs especially have a long lifetime, high efficiency and low operating voltage. The present invention therefore provides these compounds and electronic devices, especially organic electroluminescent devices, comprising these compounds.

The present application thus provides a compound of a formula (I)

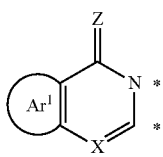

where a unit of formula (II) or formula (III) is bonded at the bonding sites labeled * in the ring, in each case via the bonds labeled *,

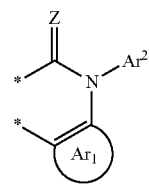

Formula (II)

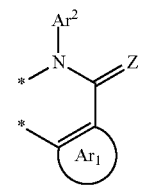

Formula (III)

and where the variables that occur are as follows:

X is N or $CAr^3$;

Z is the same or different at each instance and is selected from O and S;

$Ar^1$ is the same or different at each instance and is selected from fused-on aromatic ring systems having 6 to 40 aromatic ring atoms, and fused-on heteroaromatic ring systems having 5 to 40 aromatic ring atoms; where the aromatic ring systems and heteroaromatic ring systems are each substituted by $R^1$ radicals;

$Ar^2$ is selected from branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where the groups mentioned are each substituted by one or more $R^2$ radicals;

$Ar^3$ is selected from H, D, F, Cl, Br, I, C(=O)$R^3$, CN, Si($R^3$)$_3$, N($R^3$)$_2$, P(=O)($R^3$)$_2$, O$R^3$, S(=O)$R^3$, S(=O)$_2R^3$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where the alkyl, alkoxy, alkenyl and alkynyl groups mentioned and the aromatic ring systems and heteroaromatic ring systems mentioned are each substituted by $R^3$ radicals; and where one or more CH$_2$ groups in the alkyl, alkoxy, alkenyl and alkynyl groups mentioned may be replaced by —$R^3$C=C$R^3$—, —C≡C—, Si($R^3$)$_2$, C=O, C=N$R^3$, —C(=O)O—, —C(=O)N$R^3$—, N$R^3$, P(=O)($R^3$), —O—, —S—, SO or SO$_2$, $R^1$ is the same or different at each instance and is selected from H, D, F, Cl, Br, I, C(=O)$R^4$, CN, Si($R^4$)$_3$, N($R^4$)$_2$, P(=O)($R^4$)$_2$, O$R^4$, S(=O)$R^4$, S(=O)$_2R^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ radicals may be joined to one another and may form a ring; where the alkyl, alkoxy, alkenyl and alkynyl groups mentioned and the aromatic ring systems and heteroaromatic ring systems mentioned are each substituted by $R^4$ radicals; and where one or more CH$_2$ groups in the alkyl, alkoxy, alkenyl and alkynyl groups mentioned may be replaced by —R⁴C═CR⁴—, —C≡C—, Si(R⁴)₂, C═O, C═NR⁴, —C(═O)O—, —C(═O)NR⁴—, NR⁴, P(═O)(R⁴), —O—, —S—, SO or SO₂;

R² is the same or different at each instance and is selected from H, D, F, Cl, Br, I, C(═O)R⁴, CN, Si(R⁴)₃, N(R⁴)₂, P(═O)(R⁴)₂, OR⁴, S(═O)R⁴, S(═O)₂R⁴, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R² radicals may be joined to one another and may form a ring; where the alkyl, alkoxy, alkenyl and alkynyl groups mentioned and the aromatic ring systems and heteroaromatic ring systems mentioned are each substituted by R⁴ radicals; and where one or more CH₂ groups in the alkyl, alkoxy, alkenyl and alkynyl groups mentioned may be replaced by —R⁴C═CR⁴—, —C≡C—, Si(R⁴)₂, C═O, C═NR⁴, —C(═O)O—, —C(═O)NR⁴—, NR⁴, P(═O)(R⁴), —O—, —S—, SO or SO₂, R³ is the same or different at each instance and is selected from H, D, F, Cl, Br, I, C(═O)R⁴, CN, Si(R⁴)₃, N(R⁴)₂, P(═O)(R⁴)₂, OR⁴, S(═O)R⁴, S(═O)₂R⁴, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R³ radicals may be joined to one another and may form a ring; where the alkyl, alkoxy, alkenyl and alkynyl groups mentioned and the aromatic ring systems and heteroaromatic ring systems mentioned are each substituted by R⁴ radicals; and where one or more CH₂ groups in the alkyl, alkoxy, alkenyl and alkynyl groups mentioned may be replaced by —R⁴C═CR⁴—, —C≡C—, Si(R⁴)₂, C═O, C═NR⁴, —C(═O)O—, —C(═O)NR⁴—, NR⁴, P(═O)(R⁴), —O—, —S—, SO or SO₂;

R⁴ is the same or different at each instance and is selected from H, D, F, Cl, Br, I, C(═O)R⁵, CN, Si(R⁵)₃, N(R⁵)₂, P(═O)(R⁵)₂, OR⁵, S(═O)R⁵, S(═O)₂R⁵, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R⁴ radicals may be joined to one another and may form a ring; where the alkyl, alkoxy, alkenyl and alkynyl groups mentioned and the aromatic ring systems and heteroaromatic ring systems mentioned are each substituted by R⁵ radicals; and where one or more CH₂ groups in the alkyl, alkoxy, alkenyl and alkynyl groups mentioned may be replaced by —R⁵C═CR⁵—, —C≡C—, Si(R⁵)₂, C═O, C═NR⁵, —C(═O)O—, —C(═O)NR⁵—, NR⁵, P(═O)(R⁵), —O—, —S—, SO or SO₂, R⁵ is the same or different at each instance and is selected from H, D, F, Cl, Br, I, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more R⁵ radicals may be joined to one another and may form a ring; and where the alkyl, alkoxy, alkenyl and alkynyl groups, aromatic ring systems and heteroaromatic ring systems mentioned may be substituted by one or more radicals selected from F and CN; excluding the following compounds:

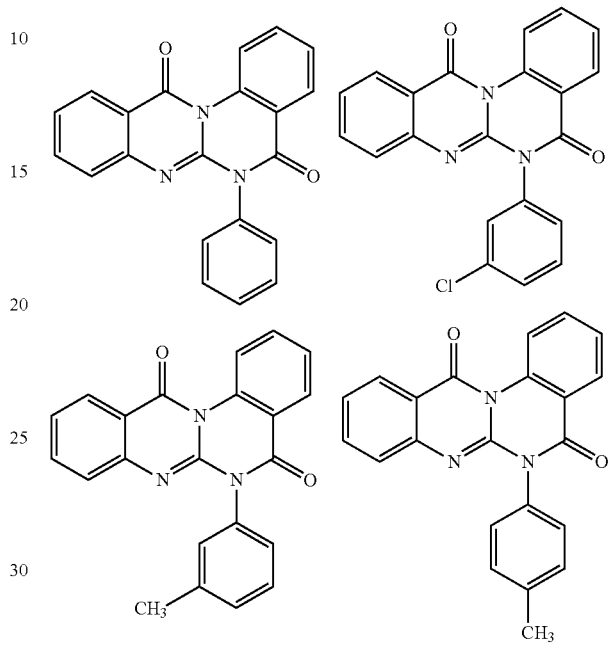

The definitions which follow are applicable to the chemical groups that are used in the present application. They are applicable unless any more specific definitions are given.

An aryl group in the context of this invention is understood to mean either a single aromatic cycle, i.e. benzene, or a fused aromatic polycycle, for example naphthalene, phenanthrene or anthracene. A fused aromatic polycycle in the context of the present application consists of two or more single aromatic cycles fused to one another. Fusion between cycles is understood here to mean that the cycles share at least one edge with one another. An aryl group in the context of this invention contains 6 to 40 aromatic ring atoms. In addition, an aryl group does not contain any heteroatom as aromatic ring atom, but only carbon atoms.

A heteroaryl group in the context of this invention is understood to mean either a single heteroaromatic cycle, for example pyridine, pyrimidine or thiophene, or a fused heteroaromatic polycycle, for example quinoline or carbazole. A fused heteroaromatic polycycle in the context of the present application consists of two or more single aromatic or heteroaromatic cycles that are fused to one another, where at least one of the aromatic and heteroaromatic cycles is a heteroaromatic cycle. Fusion between cycles is understood here to mean that the cycles share at least one edge with one another. A heteroaryl group in the context of this invention contains 5 to 40 aromatic ring atoms of which at least one is a heteroatom. The heteroatoms of the heteroaryl group are preferably selected from N, O and S.

An aryl or heteroaryl group, each of which may be substituted by the abovementioned radicals, is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, benzimidazolo[1,2-a]benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the context of this invention is a system which does not necessarily contain solely aryl groups, but which may additionally contain one or more nonaromatic rings fused to at least one aryl group. These nonaromatic rings contain exclusively carbon atoms as ring atoms. Examples of groups covered by this definition are tetrahydronaphthalene, fluorene and spirobifluorene. In addition, the term "aromatic ring system" includes systems that consist of two or more aromatic ring systems joined to one another via single bonds, for example biphenyl, terphenyl, 7-phenyl-2-fluorenyl, quaterphenyl and 3,5-diphenyl-1-phenyl. An aromatic ring system in the context of this invention contains 6 to 40 carbon atoms and no heteroatoms in the ring system. The definition of "aromatic ring system" does not include heteroaryl groups.

A heteroaromatic ring system conforms to the abovementioned definition of an aromatic ring system, except that it must contain at least one heteroatom as ring atom. As is the case for the aromatic ring system, the heteroaromatic ring system need not contain exclusively aryl groups and heteroaryl groups, but may additionally contain one or more nonaromatic rings fused to at least one aryl or heteroaryl group. The nonaromatic rings may contain exclusively carbon atoms as ring atoms, or they may additionally contain one or more heteroatoms, where the heteroatoms are preferably selected from N, O and S. One example of such a heteroaromatic ring system is benzopyranyl. In addition, the term "heteroaromatic ring system" is understood to mean systems that consist of two or more aromatic or heteroaromatic ring systems that are bonded to one another via single bonds, for example 4,6-diphenyl-2-triazinyl. A heteroaromatic ring system in the context of this invention contains 5 to 40 ring atoms selected from carbon and heteroatoms, where at least one of the ring atoms is a heteroatom. The heteroatoms of the heteroaromatic ring system are preferably selected from N, O and S.

The terms "heteroaromatic ring system" and "aromatic ring system" as defined in the present application thus differ from one another in that an aromatic ring system cannot have a heteroatom as ring atom, whereas a heteroaromatic ring system must have at least one heteroatom as ring atom. This heteroatom may be present as a ring atom of a nonaromatic heterocyclic ring or as a ring atom of an aromatic heterocyclic ring.

In accordance with the above definitions, any aryl group is covered by the term "aromatic ring system", and any heteroaryl group is covered by the term "heteroaromatic ring system".

An aromatic ring system having 6 to 40 aromatic ring atoms or a heteroaromatic ring system having 5 to 40 aromatic ring atoms is especially understood to mean groups derived from the groups mentioned above under aryl groups and heteroaryl groups, and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, or from combinations of these groups.

In the context of the present invention, a straight-chain alkyl group having 1 to 20 carbon atoms and a branched or cyclic alkyl group having 3 to 20 carbon atoms and an alkenyl or alkynyl group having 2 to 40 carbon atoms in which individual hydrogen atoms or $CH_2$ groups may also be substituted by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals.

An alkoxy or thioalkyl group having 1 to 20 carbon atoms in which individual hydrogen atoms or $CH_2$ groups may also be substituted by the groups mentioned above in the definition of the radicals is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. In addition, however, the abovementioned wording shall also be understood to mean that, if one of the two radicals is hydrogen, the second radical binds to the position to which the hydrogen atom was bonded, forming a ring.

Preferably, Z is O.

Preferably, X is N. In an alternative, likewise preferred embodiment, X is $CAr^3$.

Preferably, $Ar^1$ is the same or different at each instance and is selected from fused-on aromatic ring systems having 6 to 18 aromatic ring atoms, and fused-on heteroaromatic ring systems having 5 to 18 aromatic ring atoms, where the ring systems mentioned are substituted by $R^1$ radicals. Further preferably, $Ar^1$ is the same or different at each instance and is selected from fused-on aryl groups having 6 to 18 aromatic ring atoms and fused-on heteroaryl groups having 5 to 18 aromatic ring atoms, each substituted by $R^1$ radicals. More preferably, Ar¹ is the same or different at each instance and is selected from fused-on groups selected from benzene, biphenyl, pyridine, pyrimidine, pyridazine, naphthalene, quinoline, quinazoline, phenanthrene, anthracene, fluorene, carbazole, furan, dibenzofuran, thiophene and dibenzothiophene, especially preferably benzene, pyridine, furan and thiophene, most preferably benzene, each substituted by $R^1$ radicals.

Preferably, $Ar^2$ is an aromatic ring system which has 6 to 40 aromatic ring atoms and is substituted by $R^2$ radicals. More preferably, $Ar^2$ is selected from benzene, pyridine, pyrimidine, pyridazine, naphthalene, quinoline, quinazoline, phenanthrene, anthracene, fluorene, carbazole, dibenzofuran, dibenzothiophene, biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, each substituted by $R^2$ radicals, or from combinations of these groups; $Ar^2$ is most preferably selected from phenyl, pyridine, naphthalene, triphenylene, carbazole, pyrimidine, triazine, triazinylphenylene and biphenyl, each substituted by $R^2$ radicals.

Preferably, $Ar^3$ is the same or different at each instance and is selected from aromatic ring systems which have 6 to 40 aromatic ring atoms and are substituted by $R^3$ radicals, and heteroaromatic ring systems which have 5 to aromatic ring atoms and are substituted by $R^3$ radicals.

Preferably, $R^1$ is the same or different at each instance and is selected from H, D, F, CN, $Si(R^4)_3$, $N(R^4)_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where the alkyl groups mentioned, the aromatic ring systems mentioned and the heteroaromatic ring systems mentioned are each substituted by $R^4$ radicals; and where one or more $CH_2$ groups in the alkyl groups mentioned may be replaced by —C≡C—, —$R^4$C=C$R^4$—, $Si(R^4)_2$, C=O, C=N$R^4$, —N$R^4$—, —O—, —S—, —C(=O)O— or —C(=O)N$R^4$—.

Preferably, $R^2$ is the same or different at each instance and is selected from H, D, F, CN, $Si(R^4)_3$, $N(R^4)_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where the alkyl groups mentioned, the aromatic ring systems mentioned and the heteroaromatic ring systems mentioned are each substituted by $R^4$ radicals; and where one or more $CH_2$ groups in the alkyl groups mentioned may be replaced by —C≡C—, —$R^4$C=C$R^4$—, $Si(R^4)_2$, C=O, C=N$R^4$, —N$R^4$—, —O—, —S—, —C(=O)O— or —C(=O)N$R^4$—.

Preferably, $R^3$ is the same or different at each instance and is selected from H, D, F, CN, $Si(R^4)_3$, $N(R^4)_2$, straight-chain alkyl groups having 1 to 20 carbon atoms, branched or cyclic alkyl groups having 3 to 20 carbon atoms, aromatic ring systems having 6 to 40 aromatic ring atoms and heteroaromatic ring systems having 5 to 40 aromatic ring atoms; where the alkyl groups mentioned, the aromatic ring systems mentioned and the heteroaromatic ring systems mentioned are each substituted by $R^4$ radicals; and where one or more $CH_2$ groups in the alkyl groups mentioned may be replaced by —C≡C—, —$R^4$C=C$R^4$—, $Si(R^4)_2$, C=O, C=N$R^4$, —N$R^4$—, —O—, —S—, —C(=O)O— or —C(=O)N$R^4$—.

Preferably, $R^4$ is the same or different at each instance and is selected from H, D, F, CN, alkyl groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^4$ radicals may be joined to one another and may form a ring; and where the alkyl, alkenyl and alkynyl groups, aromatic ring systems and heteroaromatic ring systems mentioned may be substituted by one or more radicals selected from F and CN.

Preferably, the compounds of the formula (I) conform to one of the formulae (IV) to (VII):

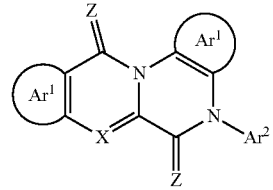

Formula (IV)

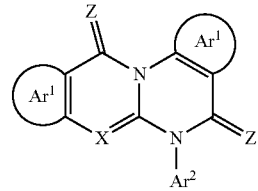

Formula (V)

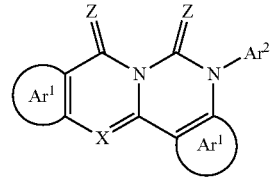

Formula (VI)

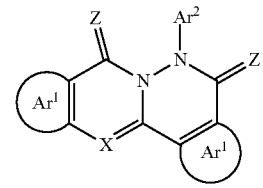

Formula (VII)

where the variables are as defined for compounds of the formula (I).

Among the abovementioned formulae, particular preference is given to the formulae (IV), (V) and (VI).

More preferably, the compounds of the formula (IV) conform to one of the formulae (VIII) and (IX):

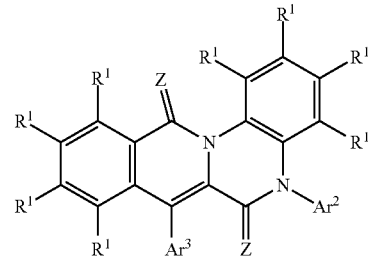

Formula (VIII)

-continued

Formula (IX)

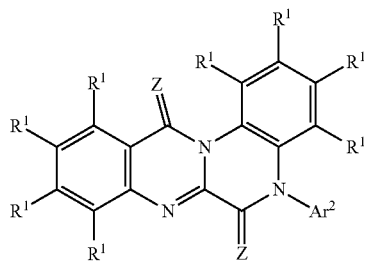

where the variables are as defined for compounds of the formula (I). Preferably, the variables in formulae (VIII) and (IX) correspond to their above-specified preferred embodiments.

More preferably, the compounds of the formula (V) conform to one of the formulae (X) and (XI):

Formula (X)

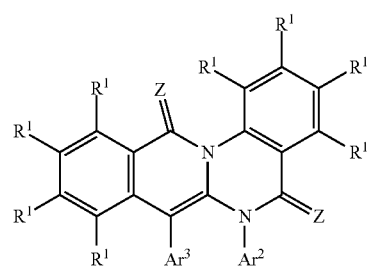

Formula (XI)

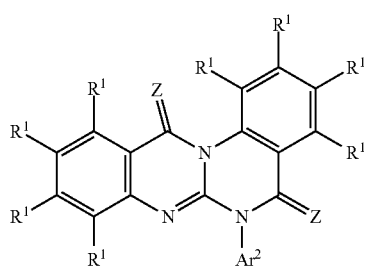

where the variables are as defined for compounds of the formula (I). Preferably, the variables in formulae (X) and (XI) correspond to their above-specified preferred embodiments.

More preferably, the compounds of the formula (VI) conform to one of the formulae (XII) and (XIII):

Formula (XII)

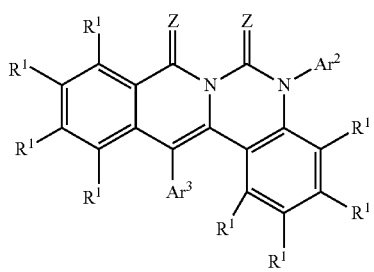

-continued

Formula (XIII)

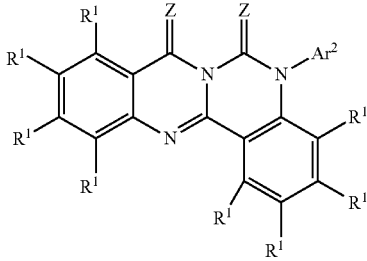

where the variables are as defined for compounds of the formula (I). Preferably, the variables in formulae (XII) and (XIII) correspond to their above-specified preferred embodiments.

Particular preference is further given to compounds of the formula (I) in which at least one group, preferably two groups, selected from $R^1$, $Ar^2$ and $Ar^3$, and more preferably at least one group, preferably two groups, selected from $R^1$ and $Ar^2$, is/are selected from aromatic ring systems which have 6 to aromatic ring atoms and are substituted by $R^4$ or $R^2$ or $R^3$ radicals, and heteroaromatic ring systems which have 5 to 40 aromatic ring atoms and are substituted by $R^4$ or $R^2$ or $R^3$ radicals.

In these cases, the aromatic and heteroaromatic ring systems are preferably selected from the R-1 to R-84 groups:

R-1

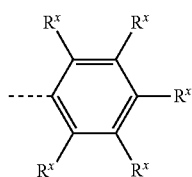

R-2

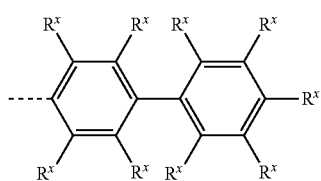

R-3

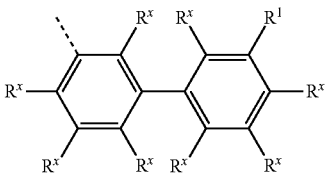

R-4

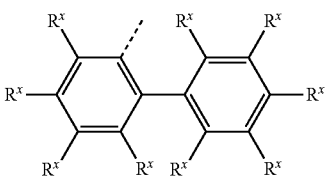

-continued
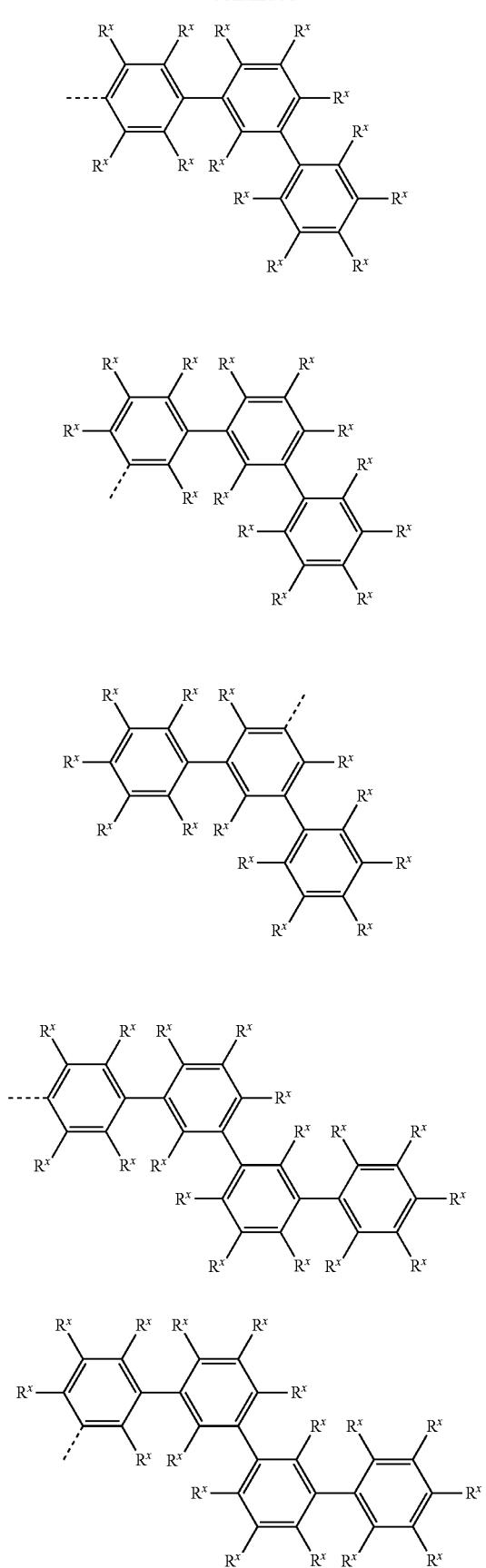
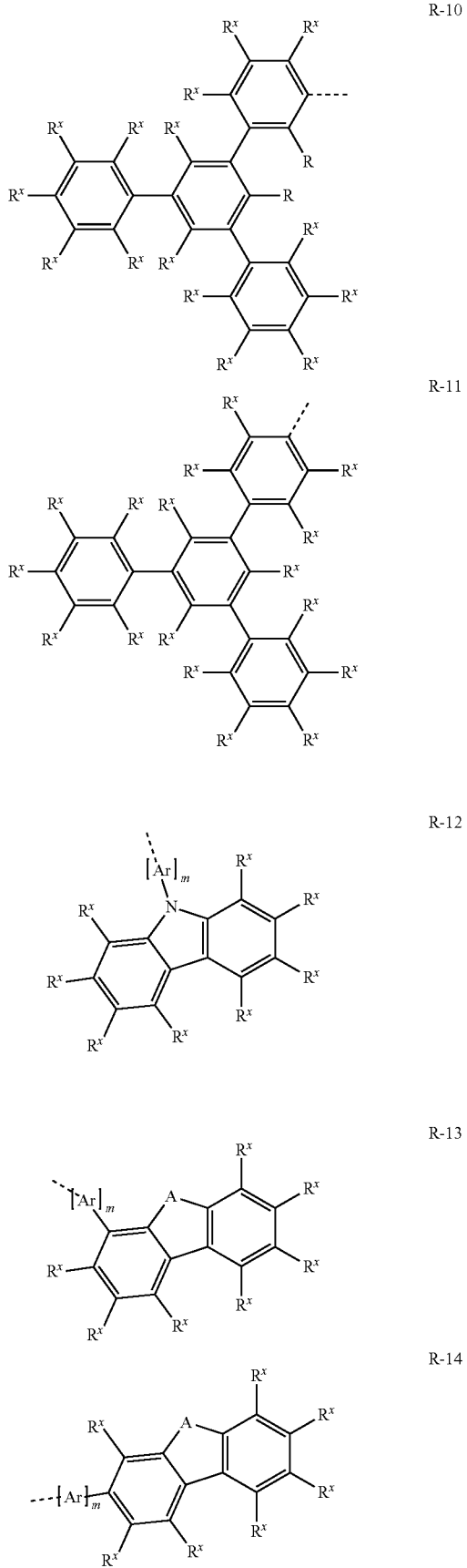

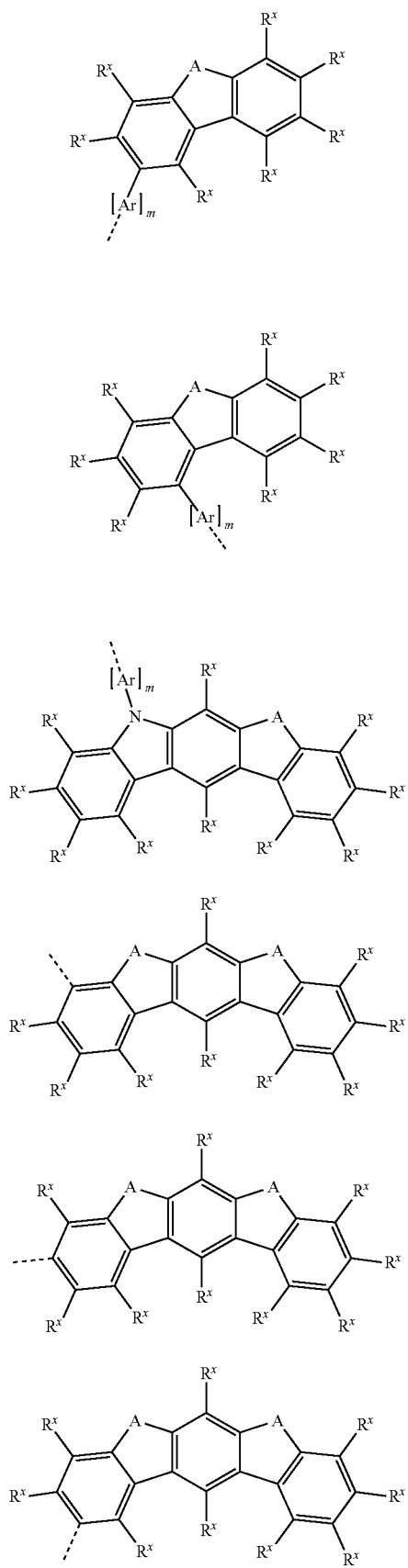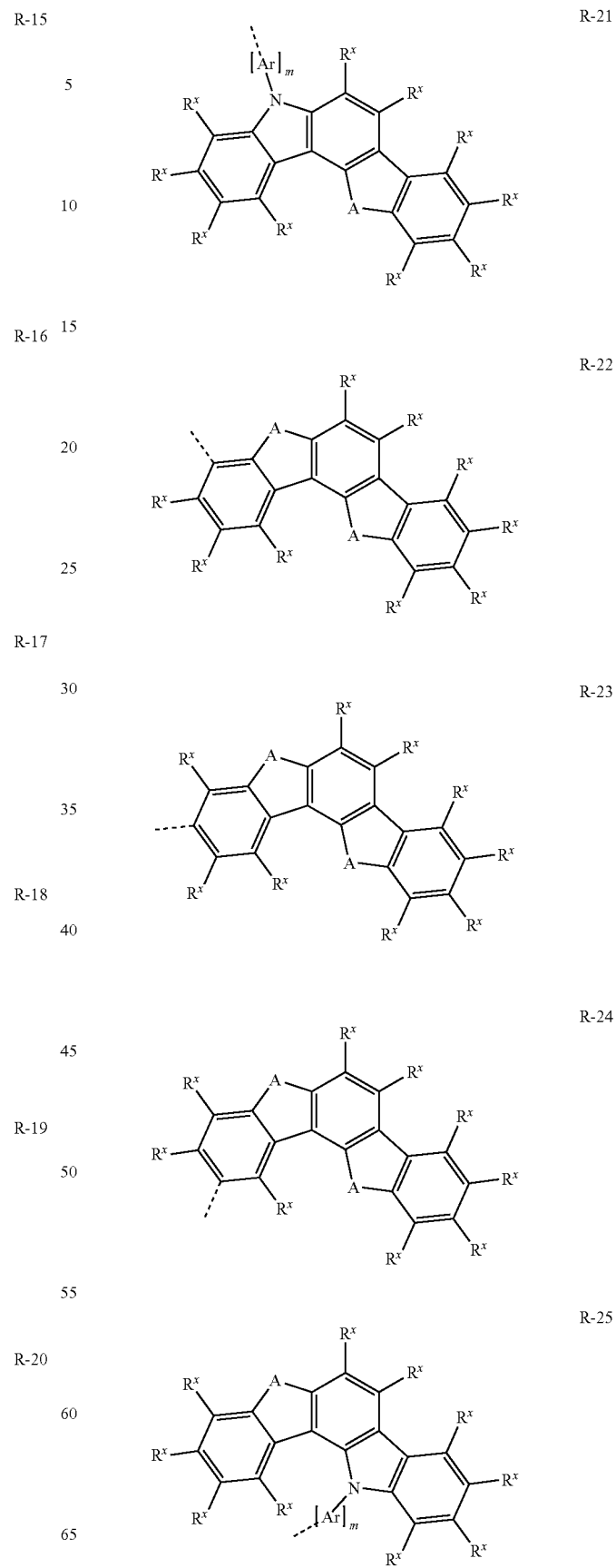

R-26
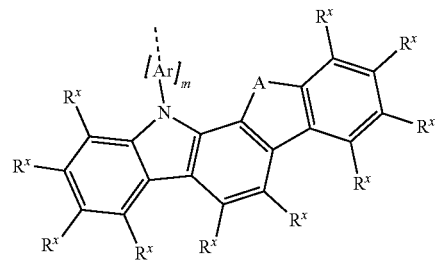
R-27
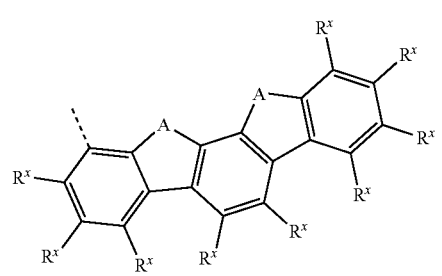
R-28
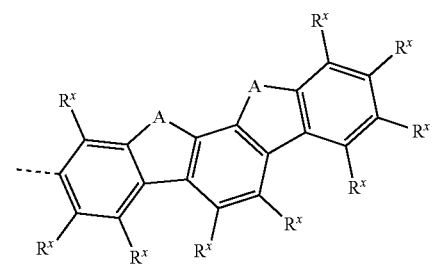
R-29
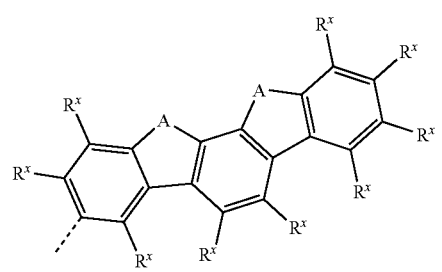
R-30
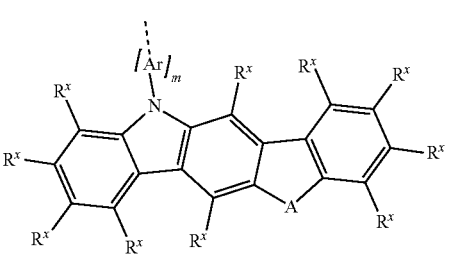
R-31
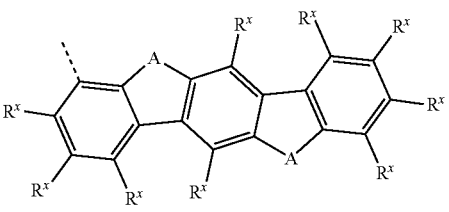
R-32
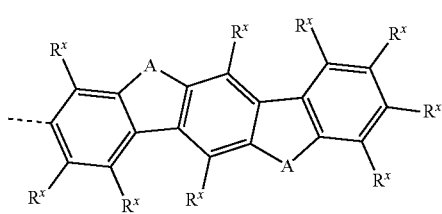
R-33
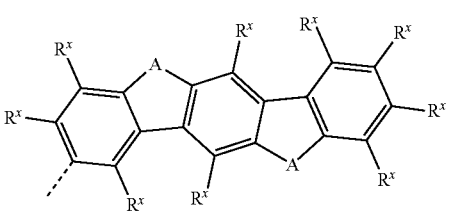
R-34
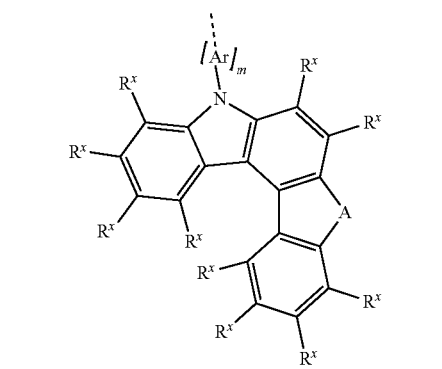
R-35
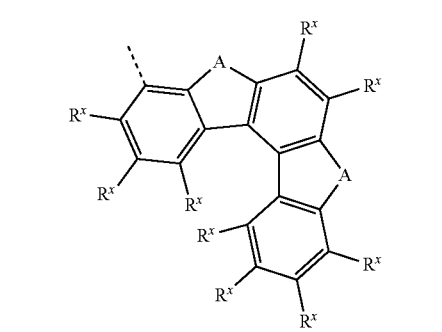
R-36
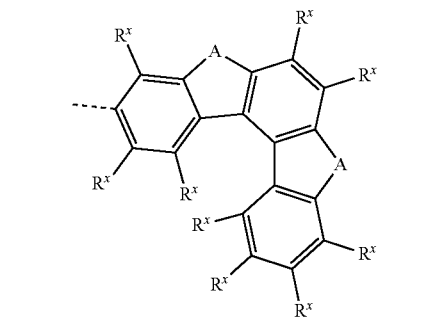

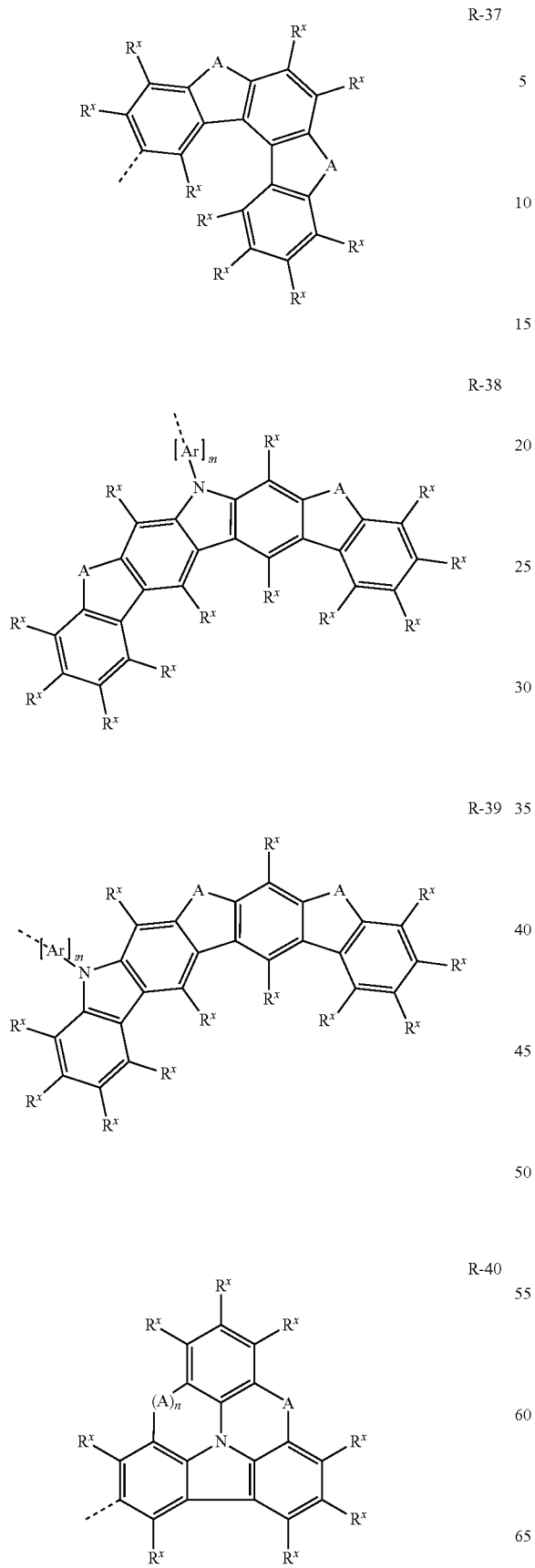

-continued
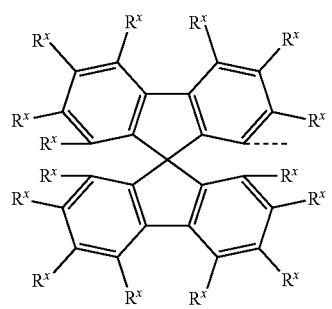
R-46
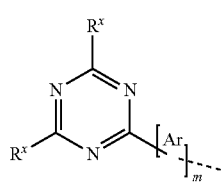
R-47
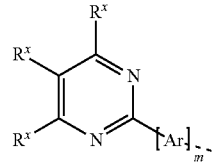
R-48
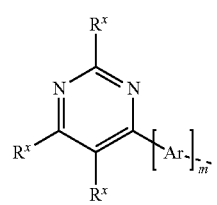
R-49
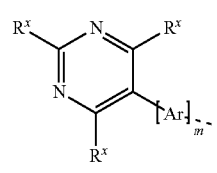
R-50
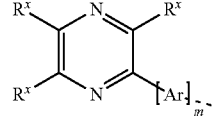
R-51
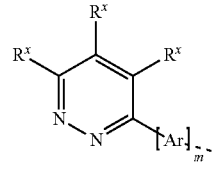
R-52
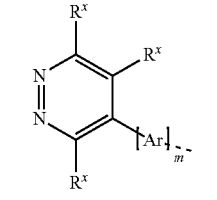
R-53
-continued
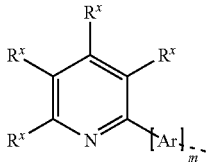
R-54
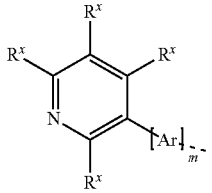
R-55
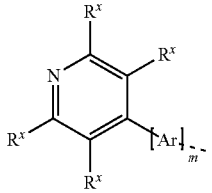
R-56
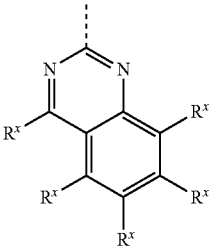
R-57
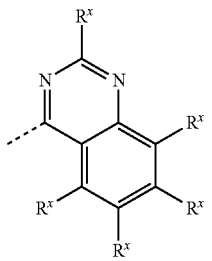
R-58
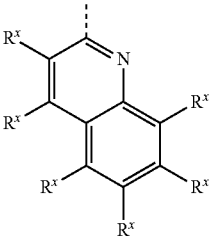
R-59
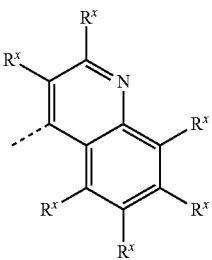
R-60

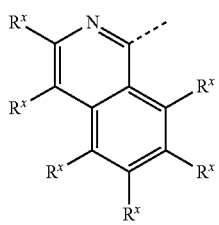 R-61
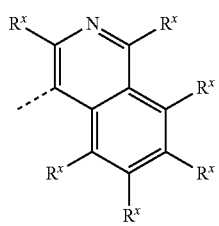 R-62
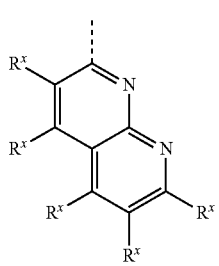 R-63
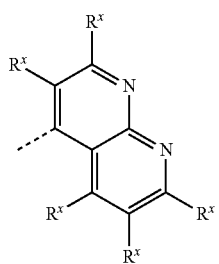 R-64
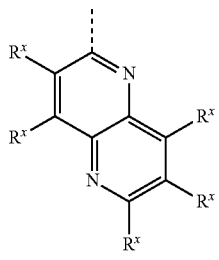 R-65
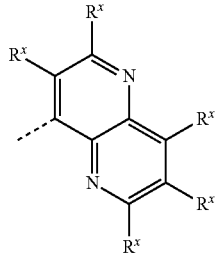 R-66
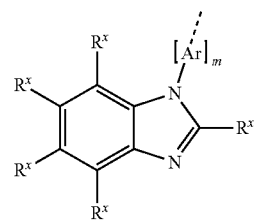 R-67
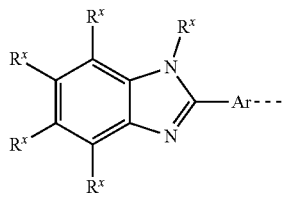 R-68
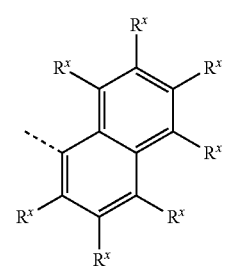 R-69
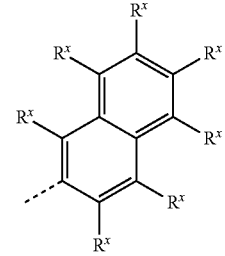 R-70
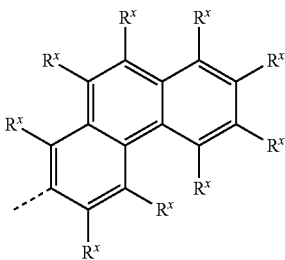 R-71
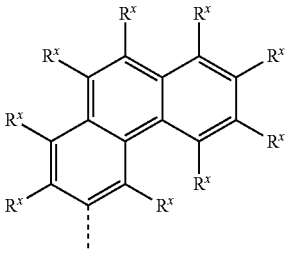 R-72

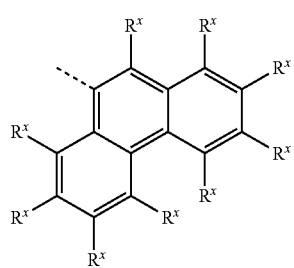
R-73
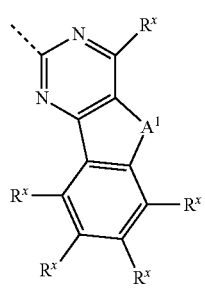
R-78
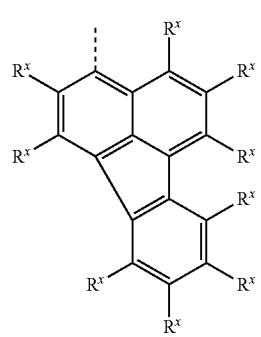
R-74
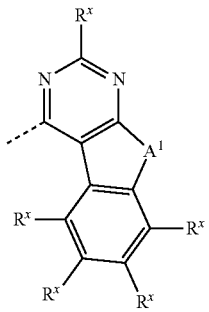
R-79
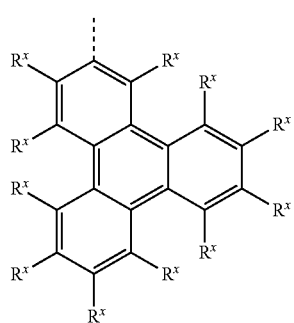
R-75
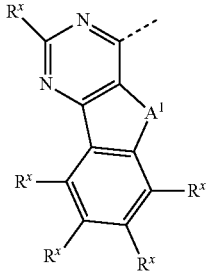
R-80
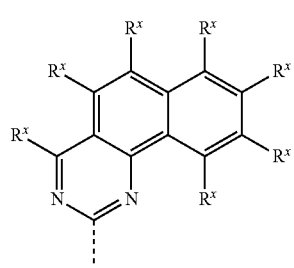
R-76
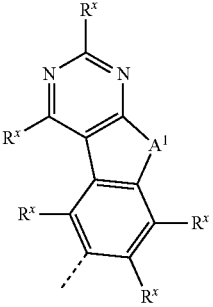
R-81
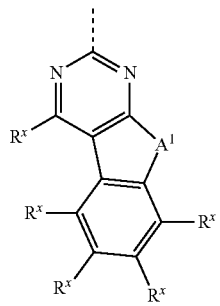
R-77
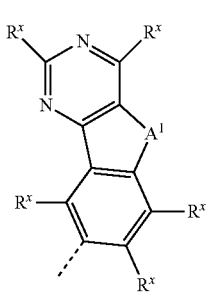
R-82

R-83

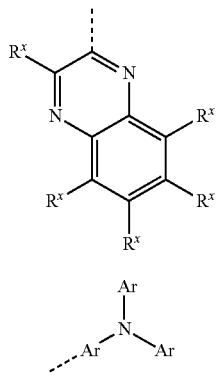

R-84

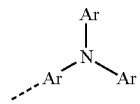

where the dotted bond represents the bond to a carbon atom in the base skeleton in formula (I) and where, in addition:
Ar in the R-1 to R-84 groups is an aromatic ring system which has 6 to 40 aromatic ring atoms and is substituted by one or more $R^x$ radicals or is a heteroaromatic ring system which has 5 to 40 aromatic ring atoms and is substituted by one or more $R^x$ radicals;
A is the same or different at each instance and is selected from $C(R^x)_2$, $NR^x$, S and O;
$A^1$ is the same or different at each instance and is selected from $C(R^x)_2$, $NR^x$, S and O;
m is 0 or 1; where m=0 means that the group in question is absent and the groups binding to the group in question are bonded directly to one another;
n is 0 or 1, where n=0 means that no A group is bonded at this position and $R^x$ radicals are bonded to the corresponding carbon atoms instead;
where $R^x$ is as follows:
when $R^1$ is a group selected from R-1 to R-84, $R^x$ is $R^4$;
when $Ar^2$ is a group selected from R-1 to R-84, $R^x$ is $R^2$;
when $Ar^3$ is a group selected from R-1 to R-84, $R^x$ is $R^3$;
and the variables $R^2$, $R^3$ and $R^4$ are as defined for the compounds of the formula (I).

Preferably, the compounds conform to one of the formulae (IV) to (VII), more preferably to one of the formulae (IV) to (VI), where:
Z is the same or different and is selected from O and S;
X is N or $CAr^3$;
$Ar^1$ is phenyl substituted by one or more $R^1$ radicals;
and $Ar^2$ is

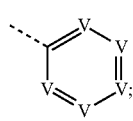

where V is the same or different and is N or $CR^2$, and where:
preferably not more than 3 V are N;
preferably no two or more adjacent V are N; and
more preferably, $Ar^2$ is a phenyl group or a triazine group, each substituted by one or more $R^2$ radicals.

Preferred compounds of the formula (I) are shown in the following table:

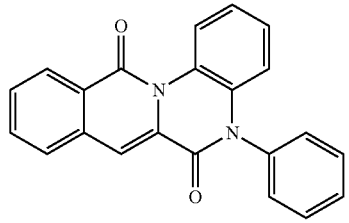 [SMILES: O=c1c2cc3ccccc3c(=O)n2c2ccccc2n1-c1ccccc1]

1

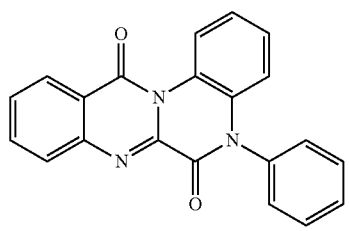

2

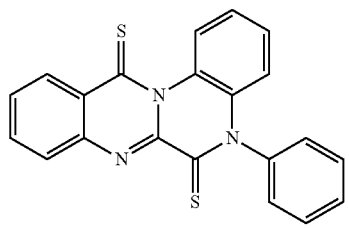 [SMILES: O=c1c2nc3ccccc3c(=O)n2c2ccccc2n1-c1ccccc1]

3

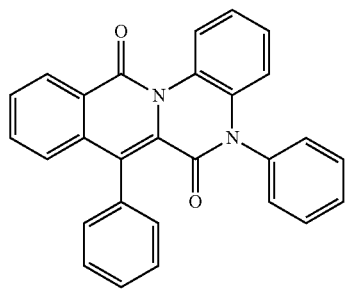 [SMILES: O=c1c2c(-c3ccccc3)c3ccccc3c(=O)n2c2ccccc2n1-c1ccccc1]

4

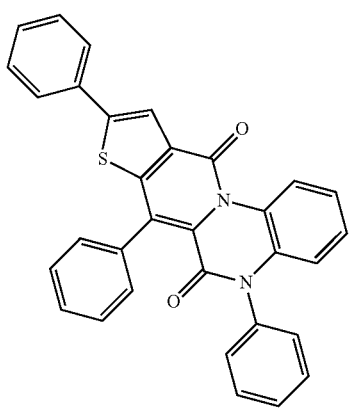 [SMILES: O=c1c2c(-c3ccccc3)c3sc(-c4ccccc4)cc3c(=O)n2c2ccccc2n1-c1ccccc1]

5

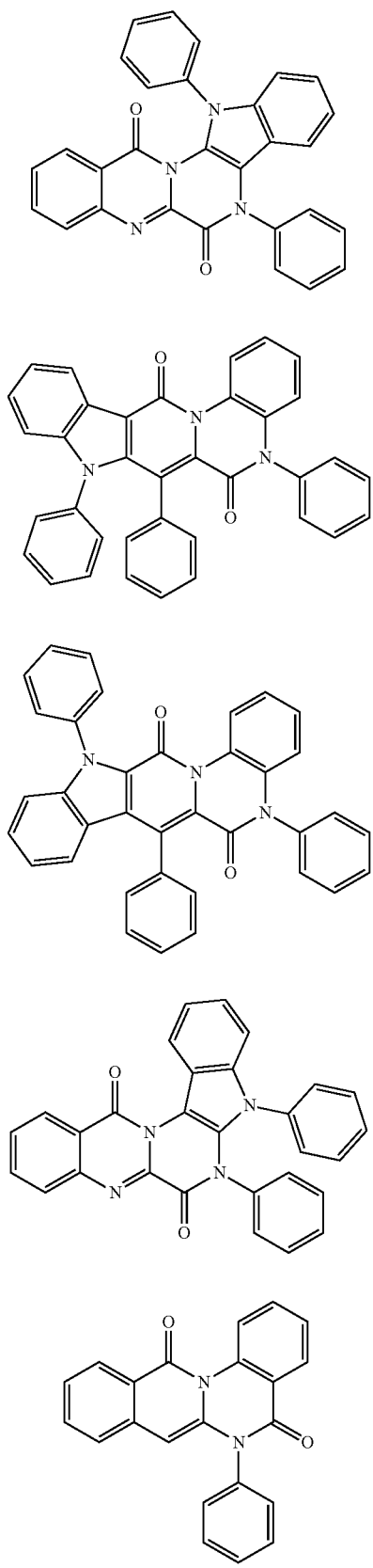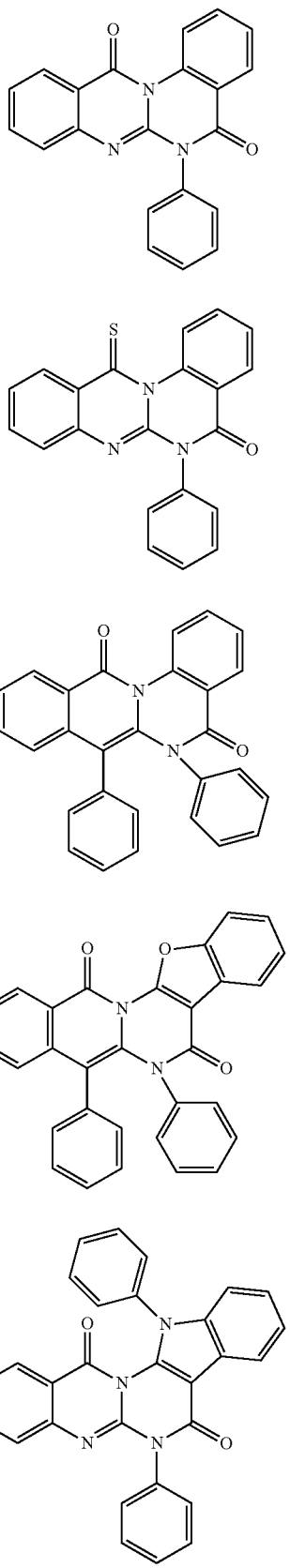

16
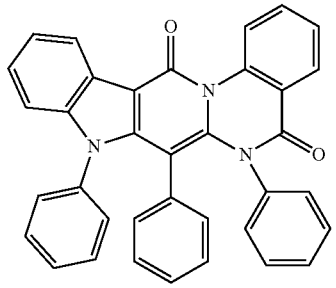 [SMILES: O=c1c2ccccc2n2c(=O)c3c4ccccc4n(-c4ccccc4)c3c(-c3ccccc3)c2n1-c1ccccc1]
17
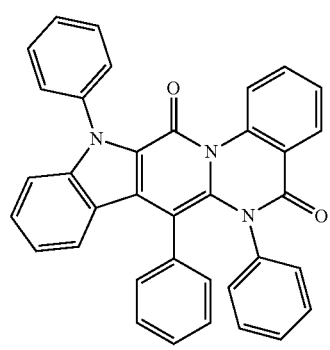 [SMILES: O=c1c2ccccc2n2c(=O)c3c(c(-c4ccccc4)c2n1-c1ccccc1)c1ccccc1n3-c1ccccc1]
18
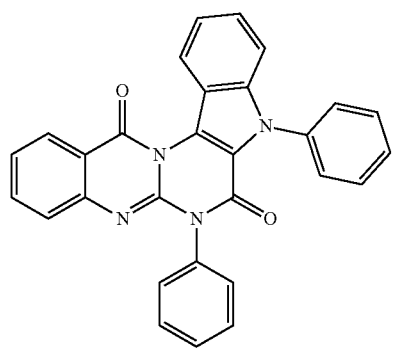 [SMILES: O=c1c2c(c3ccccc3n2-c2ccccc2)n2c(=O)c3ccccc3nc2n1-c1ccccc1]
19
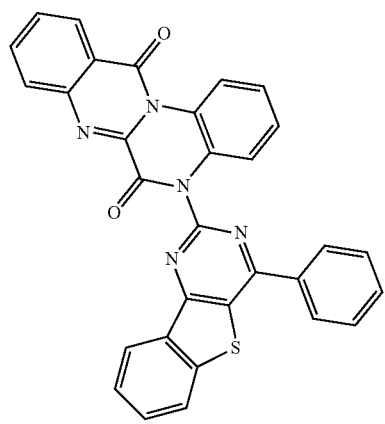 [SMILES: O=c1c2nc3ccccc3c(=O)n2c2ccccc2n1-c1nc(-c2ccccc2)c2sc3ccccc3c2n1]
20
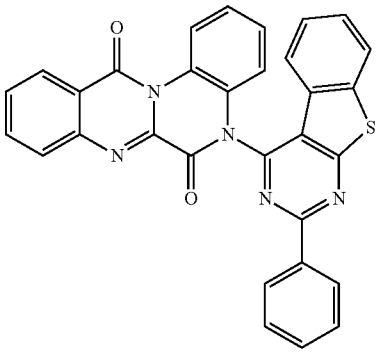 [SMILES: O=c1c2nc3ccccc3c(=O)n2c2ccccc2n1-c1nc(-c2ccccc2)nc2sc3ccccc3c12]
21
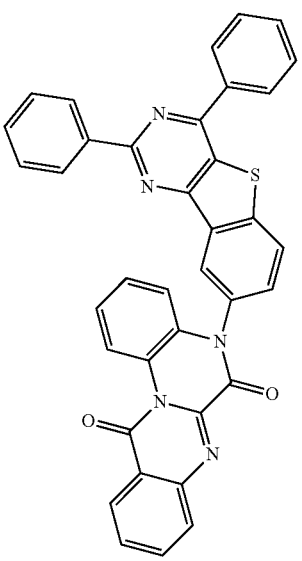 [SMILES: O=c1c2nc3ccccc3c(=O)n2c2ccccc2n1-c1ccc2sc3c(-c4ccccc4)nc(-c4ccccc4)nc3c2c1]
22
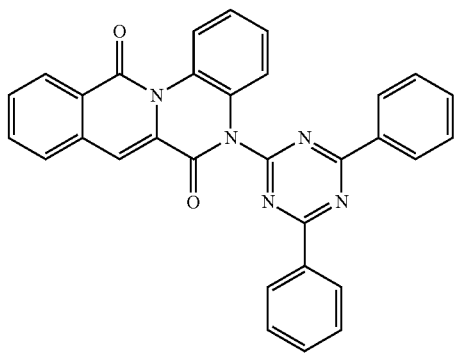 [SMILES: O=c1c2cc3ccccc3c(=O)n2c2ccccc2n1-c1nc(-c2ccccc2)nc(-c2ccccc2)n1]

31
-continued
23
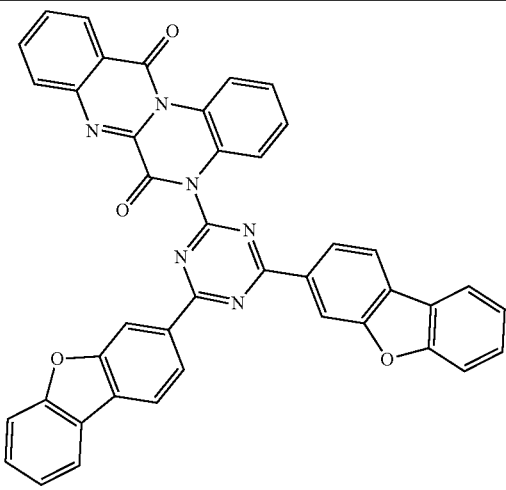
24
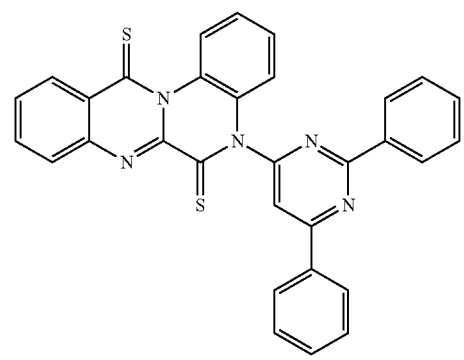 [SMILES: S=c1c2nc3ccccc3c(=S)n2c2ccccc2n1-c1cc(-c2ccccc2)nc(-c2ccccc2)n1]
25
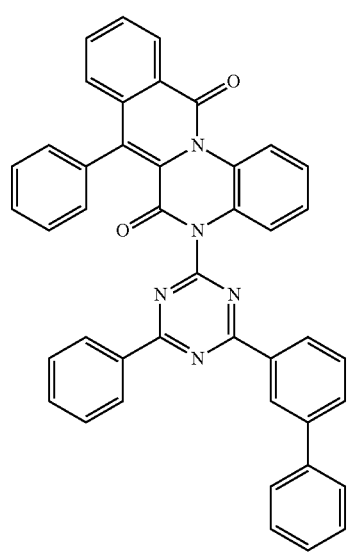 [SMILES: O=c1c2c(-c3ccccc3)c3ccccc3c(=O)n2c2ccccc2n1-c1nc(-c2ccccc2)nc(-c2cccc(-c3ccccc3)c2)n1]
32
-continued
26
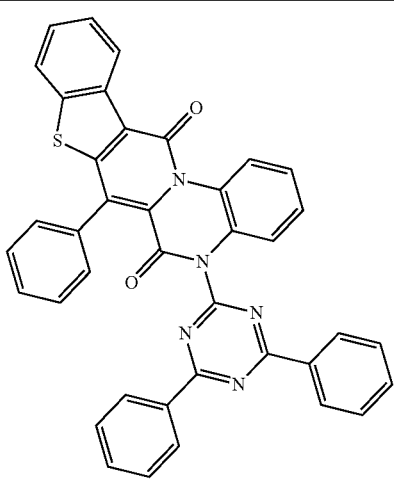
27
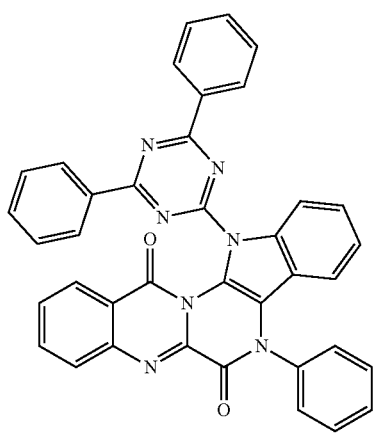 [SMILES: O=c1c2nc3ccccc3c(=O)n2c2c(c3ccccc3n2-c2nc(-c3ccccc3)nc(-c3ccccc3)n2)n1-c1ccccc1]
28
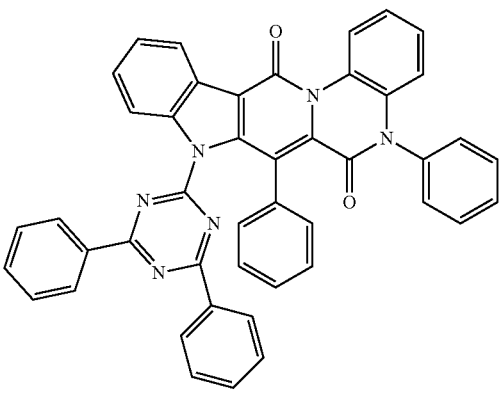 [SMILES: O=c1c2c(-c3ccccc3)c3c(c(=O)n2c2ccccc2n1-c1ccccc1)c1ccccc1n3-c1nc(-c2ccccc2)nc(-c2ccccc2)n1]

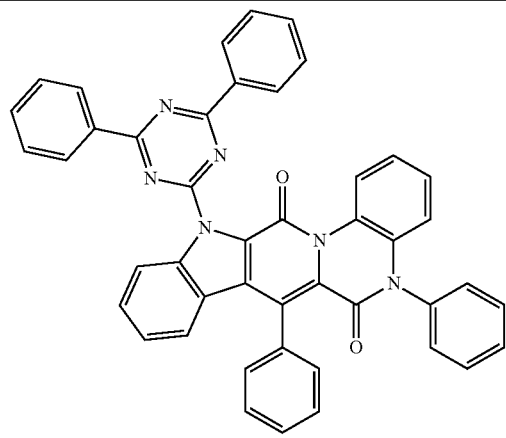
29
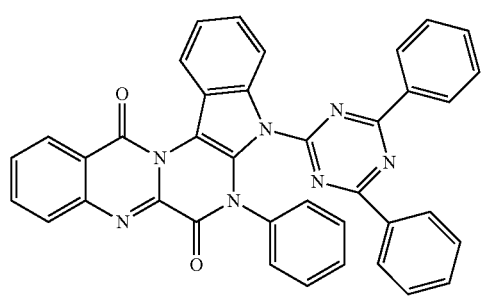 [SMILES: O=c1c2nc3ccccc3c(=O)n2c2c3ccccc3n(-c3nc(-c4ccccc4)nc(-c4ccccc4)n3)c2n1-c1ccccc1]
30
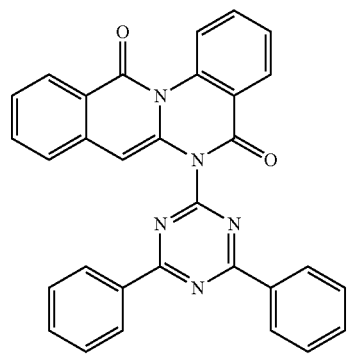 [SMILES: O=c1c2ccccc2n2c(=O)c3ccccc3cc2n1-c1nc(-c2ccccc2)nc(-c2ccccc2)n1]
31
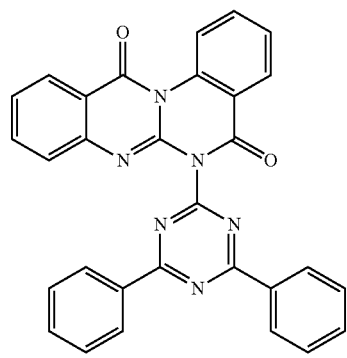
32
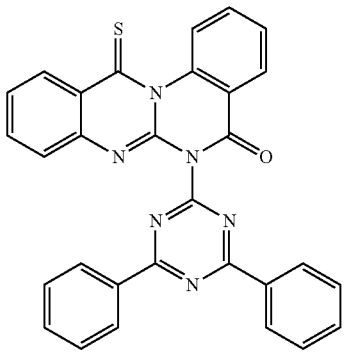 [SMILES: O=c1c2ccccc2n2c(=O)c3ccccc3nc2n1-c1nc(-c2ccccc2)nc(-c2ccccc2)n1]
33
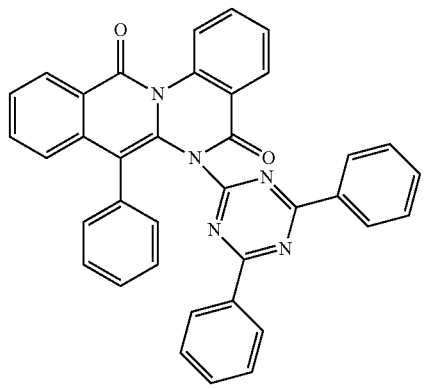 [SMILES: O=c1c2ccccc2n2c(=O)c3ccccc3c(-c3ccccc3)c2n1-c1nc(-c2ccccc2)nc(-c2ccccc2)n1]
34
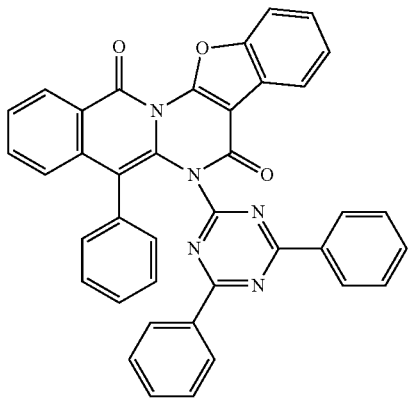 [SMILES: O=c1c2c3ccccc3oc2n2c(=O)c3ccccc3c(-c3ccccc3)c2n1-c1nc(-c2ccccc2)nc(-c2ccccc2)n1]
35
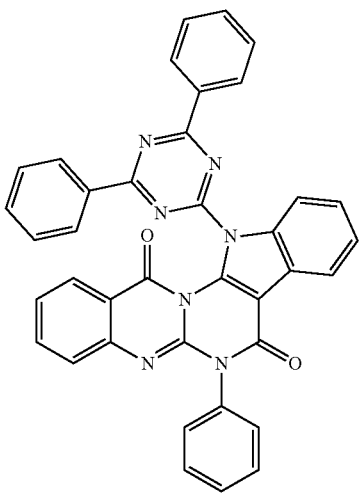 [SMILES: O=c1c2c3ccccc3n(-c3nc(-c4ccccc4)nc(-c4ccccc4)n3)c2n2c(=O)c3ccccc3nc2n1-c1ccccc1]
36

37
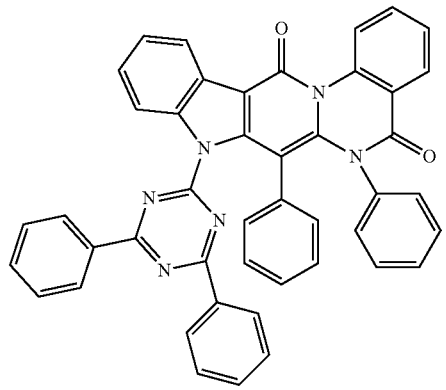 [SMILES: O=c1c2ccccc2n2c(=O)c3c4ccccc4n(-c4nc(-c5ccccc5)nc(-c5ccccc5)n4)c3c(-c3ccccc3)c2n1-c1ccccc1]
38
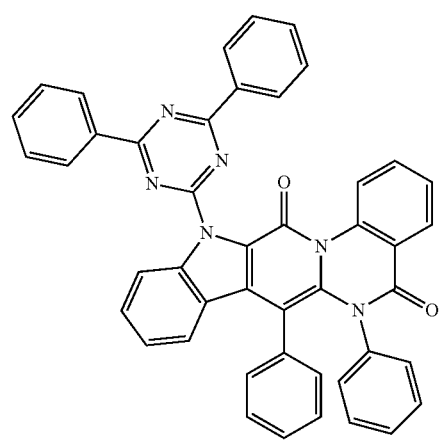 [SMILES: O=c1c2ccccc2n2c(=O)c3c(c(-c4ccccc4)c2n1-c1ccccc1)c1ccccc1n3-c1nc(-c2ccccc2)nc(-c2ccccc2)n1]
39
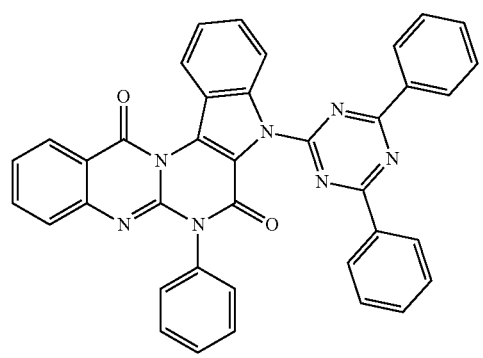 [SMILES: O=c1c2c(c3ccccc3n2-c2nc(-c3ccccc3)nc(-c3ccccc3)n2)n2c(=O)c3ccccc3nc2n1-c1ccccc1]
40
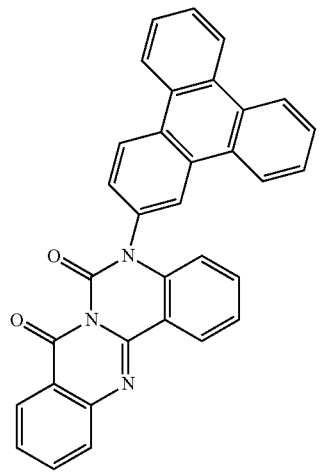 [SMILES: O=c1c2ccccc2nc2c3ccccc3n(-c3ccc4c5ccccc5c5ccccc5c4c3)c(=O)n12]
41
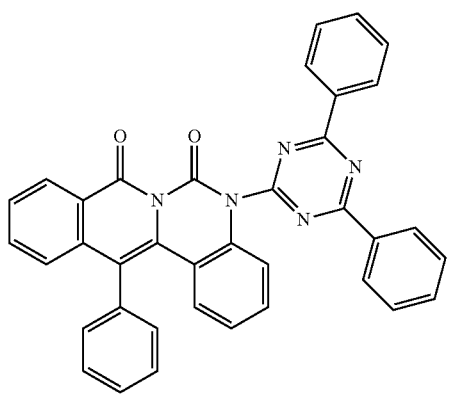 [SMILES: O=c1c2ccccc2c(-c2ccccc2)c2c3ccccc3n(-c3nc(-c4ccccc4)nc(-c4ccccc4)n3)c(=O)n12]
42
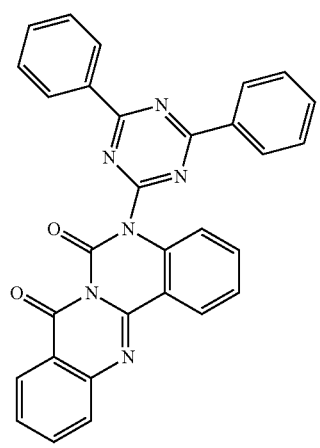 [SMILES: O=c1c2ccccc2nc2c3ccccc3n(-c3nc(-c4ccccc4)nc(-c4ccccc4)n3)c(=O)n12]

43
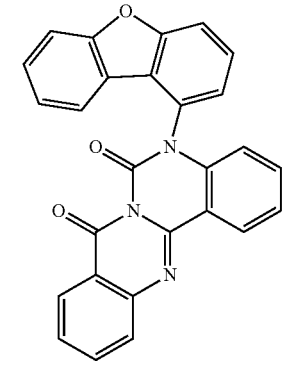 [SMILES: O=c1c2ccccc2nc2c3ccccc3n(-c3cccc4oc5ccccc5c34)c(=O)n12]
44
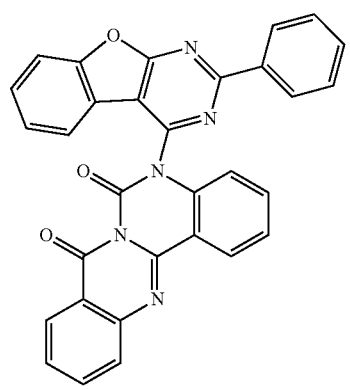 [SMILES: O=c1c2ccccc2nc2c3ccccc3n(-c3nc(-c4ccccc4)nc4oc5ccccc5c34)c(=O)n12]
45
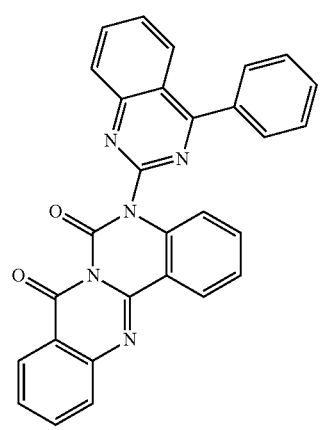 [SMILES: O=c1c2ccccc2nc2c3ccccc3n(-c3nc(-c4ccccc4)c4ccccc4n3)c(=O)n12]
46
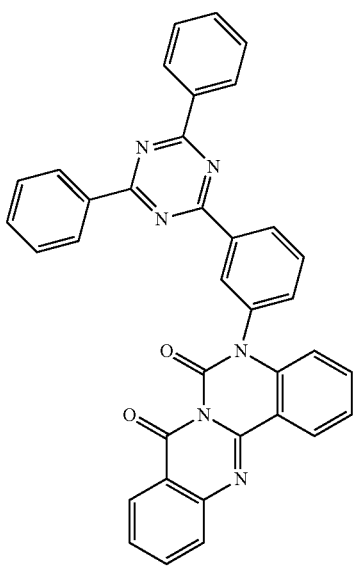 [SMILES: O=c1c2ccccc2nc2c3ccccc3n(-c3cccc(-c4nc(-c5ccccc5)nc(-c5ccccc5)n4)c3)c(=O)n12]
47
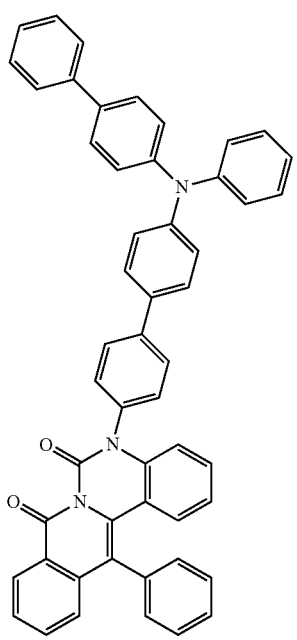 [SMILES: O=c1c2ccccc2c(-c2ccccc2)c2c3ccccc3n(-c3ccc(-c4ccc(N(c5ccccc5)c5ccc(-c6ccccc6)cc5)cc4)cc3)c(=O)n12]

48
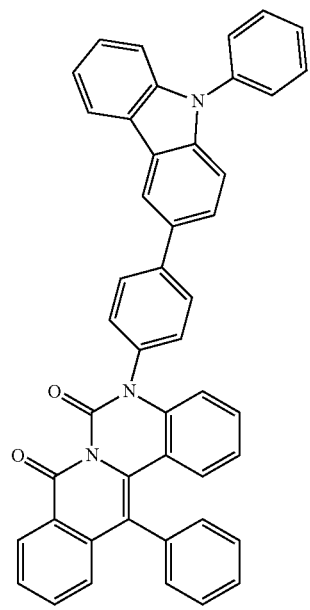 [SMILES: O=c1c2ccccc2c(-c2ccccc2)c2c3ccccc3n(-c3ccc(-c4ccc5c(c4)c4ccccc4n5-c4ccccc4)cc3)c(=O)n12]
49
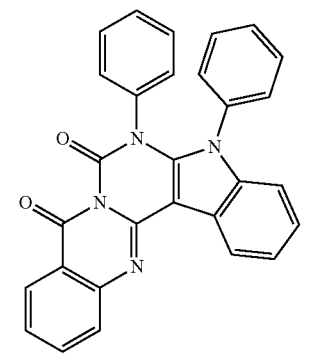 [SMILES: O=c1c2ccccc2nc2c3c4ccccc4n(-c4ccccc4)c3n(-c3ccccc3)c(=O)n12]
50
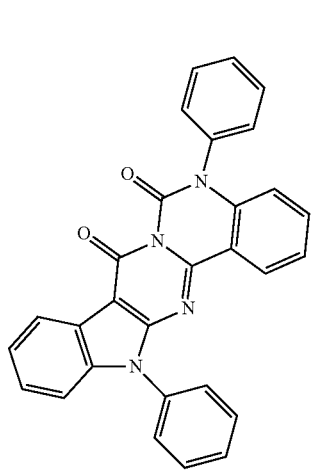 [SMILES: O=c1c2c3ccccc3n(-c3ccccc3)c2nc2c3ccccc3n(-c3ccccc3)c(=O)n12]
51
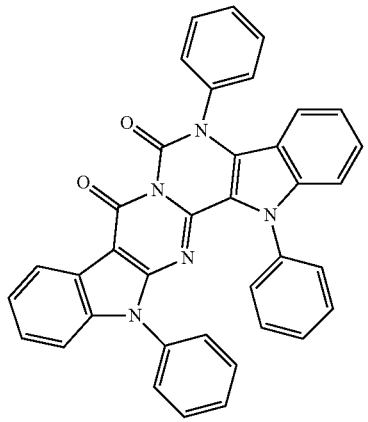 [SMILES: O=c1c2c3ccccc3n(-c3ccccc3)c2nc2c3c(c4ccccc4n3-c3ccccc3)n(-c3ccccc3)c(=O)n12]
52
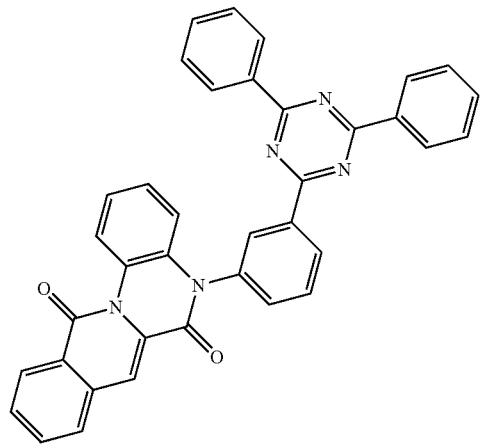 [SMILES: O=c1c2cc3ccccc3c(=O)n2c2ccccc2n1-c1cccc(-c2nc(-c3ccccc3)nc(-c3ccccc3)n2)c1]
53
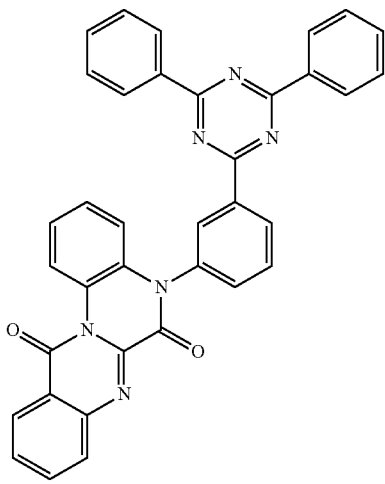 [SMILES: O=c1c2nc3ccccc3c(=O)n2c2ccccc2n1-c1cccc(-c2nc(-c3ccccc3)nc(-c3ccccc3)n2)c1]

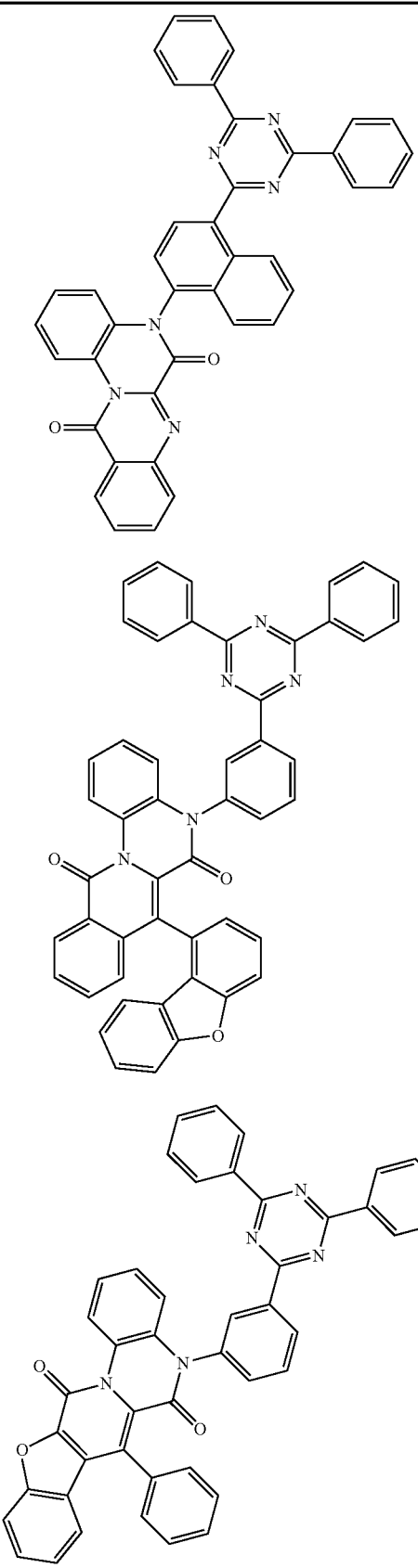
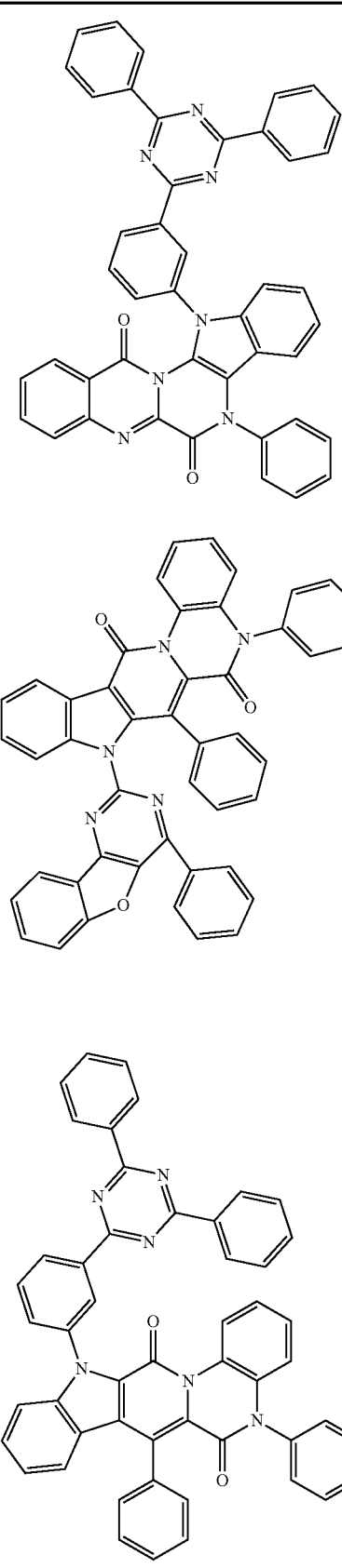

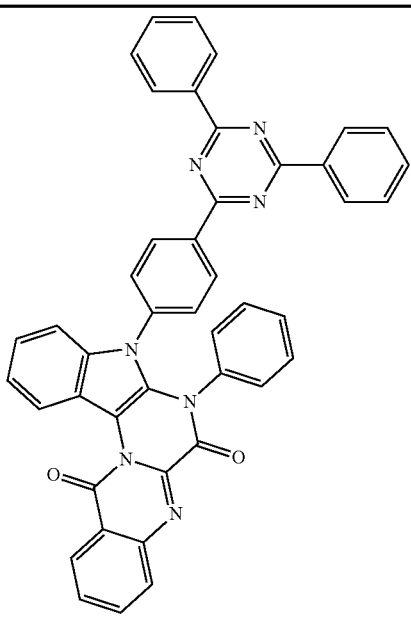
60
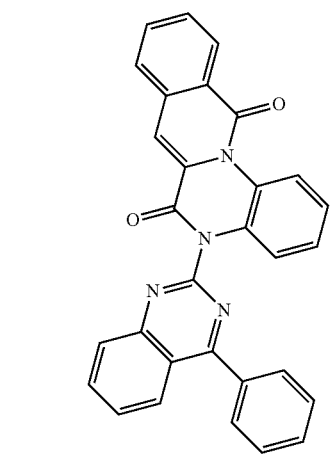 [SMILES: O=c1c2cc3ccccc3c(=O)n2c2ccccc2n1-c1nc(-c2ccccc2)c2ccccc2n1]
61
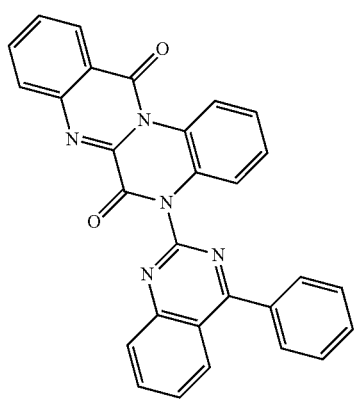 [SMILES: O=c1c2nc3ccccc3c(=O)n2c2ccccc2n1-c1nc(-c2ccccc2)c2ccccc2n1]
62
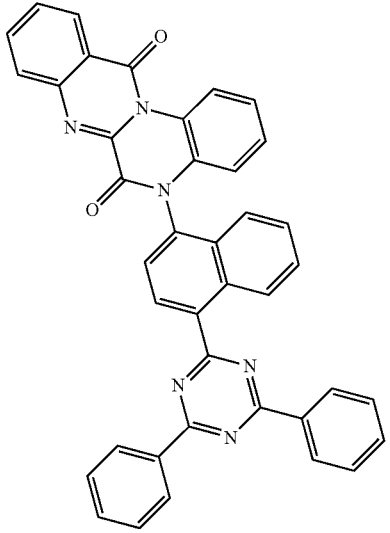 [SMILES: O=c1c2nc3ccccc3c(=O)n2c2ccccc2n1-c1ccc(-c2nc(-c3ccccc3)nc(-c3ccccc3)n2)c2ccccc12]
63
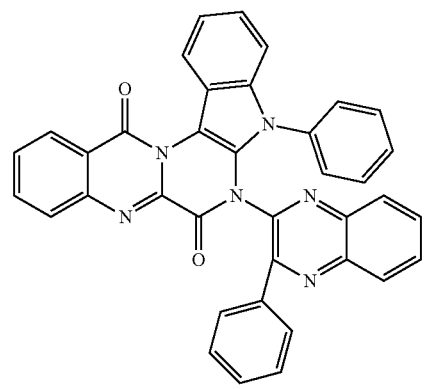 [SMILES: O=c1c2nc3ccccc3c(=O)n2c2c3ccccc3n(-c3ccccc3)c2n1-c1nc2ccccc2nc1-c1ccccc1]
64
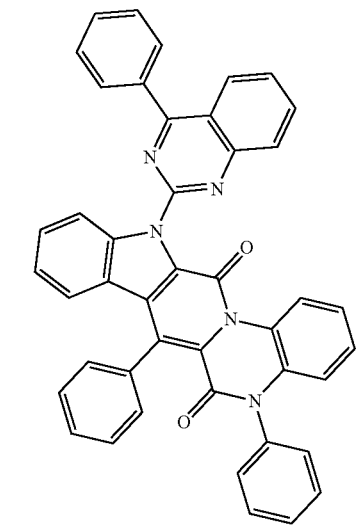 [SMILES: O=c1c2c(-c3ccccc3)c3c4ccccc4n(-c4nc(-c5ccccc5)c5ccccc5n4)c3c(=O)n2c2ccccc2n1-c1ccccc1]
65

-continued
66
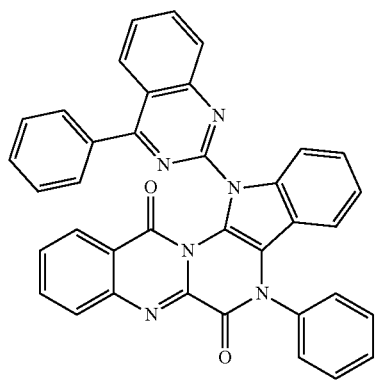 [SMILES: O=c1c2nc3ccccc3c(=O)n2c2c(c3ccccc3n2-c2nc(-c3ccccc3)c3ccccc3n2)n1-c1ccccc1]
67
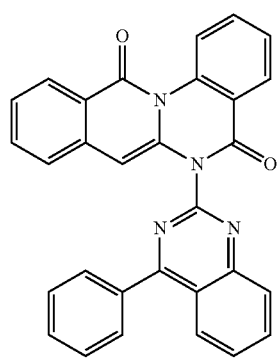 [SMILES: O=c1c2ccccc2n2c(=O)c3ccccc3cc2n1-c1nc(-c2ccccc2)c2ccccc2n1]
68
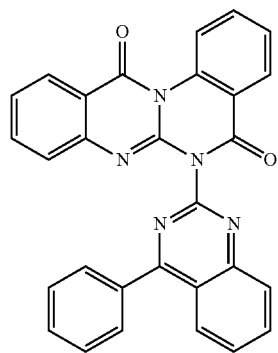 [SMILES: O=c1c2ccccc2n2c(=O)c3ccccc3nc2n1-c1nc(-c2ccccc2)c2ccccc2n1]
69
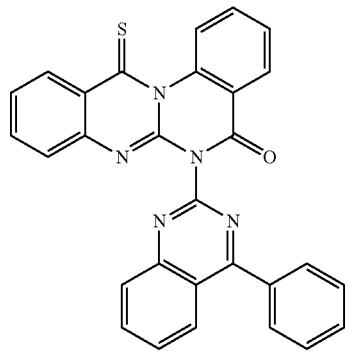 [SMILES: O=c1c2ccccc2n2c(=S)c3ccccc3nc2n1-c1nc(-c2ccccc2)c2ccccc2n1]
-continued
70
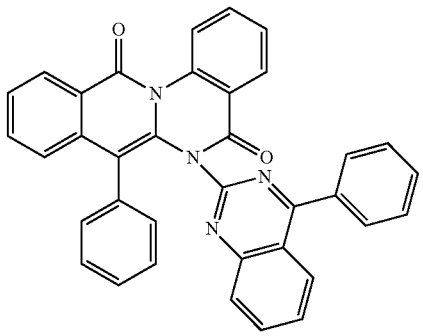 [SMILES: O=c1c2ccccc2n2c(=O)c3ccccc3c(-c3ccccc3)c2n1-c1nc(-c2ccccc2)c2ccccc2n1]
71
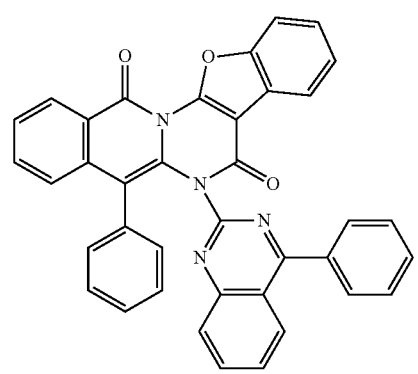 [SMILES: O=c1c2c3ccccc3oc2n2c(=O)c3ccccc3c(-c3ccccc3)c2n1-c1nc(-c2ccccc2)c2ccccc2n1]
72
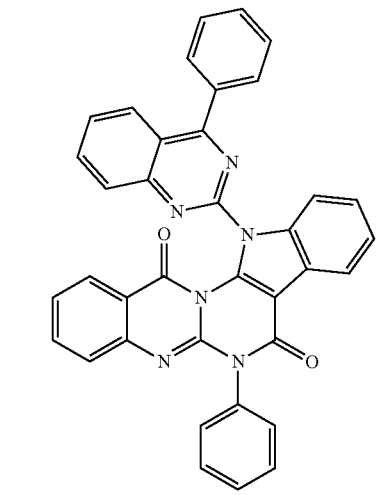 [SMILES: O=c1c2c3ccccc3n(-c3nc(-c4ccccc4)c4ccccc4n3)c2n2c(=O)c3ccccc3nc2n1-c1ccccc1]
73
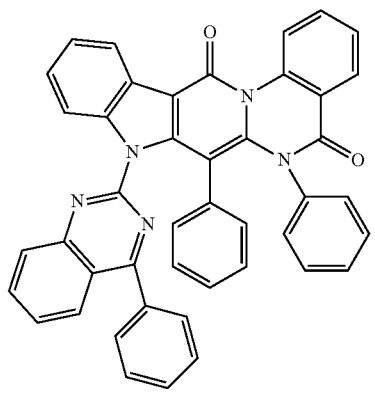 [SMILES: O=c1c2ccccc2n2c(=O)c3c4ccccc4n(-c4nc(-c5ccccc5)c5ccccc5n4)c3c(-c3ccccc3)c2n1-c1ccccc1]

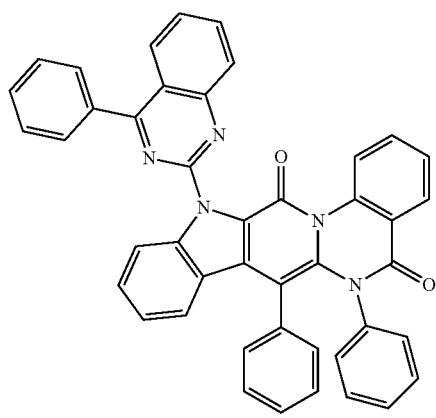 [SMILES: O=c1c2ccccc2n2c(=O)c3c(c(-c4ccccc4)c2n1-c1ccccc1)c1ccccc1n3-c1nc(-c2ccccc2)c2ccccc2n1]
74
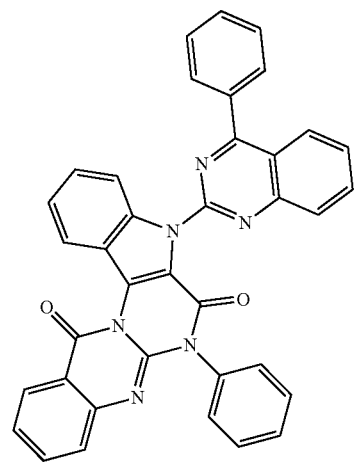 [SMILES: O=c1c2c(c3ccccc3n2-c2nc(-c3ccccc3)c3ccccc3n2)n2c(=O)c3ccccc3nc2n1-c1ccccc1]
75
76
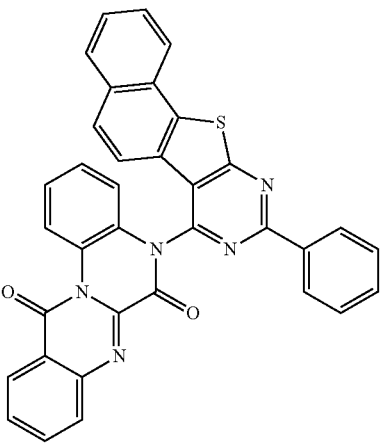 [SMILES: O=c1c2nc3ccccc3c(=O)n2c2ccccc2n1-c1nc(-c2ccccc2)nc2sc3c4ccccc4ccc3c12]
77
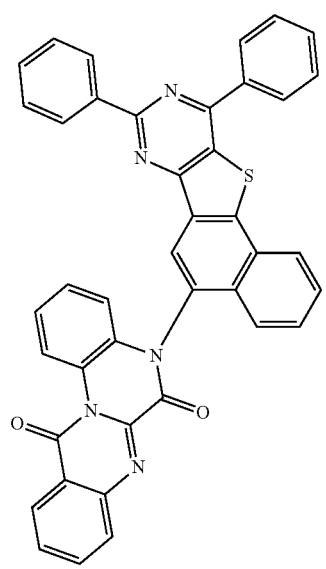 [SMILES: O=c1c2nc3ccccc3c(=O)n2c2ccccc2n1-c1cc2c3nc(-c4ccccc4)nc(-c4ccccc4)c3sc2c2ccccc12]
78
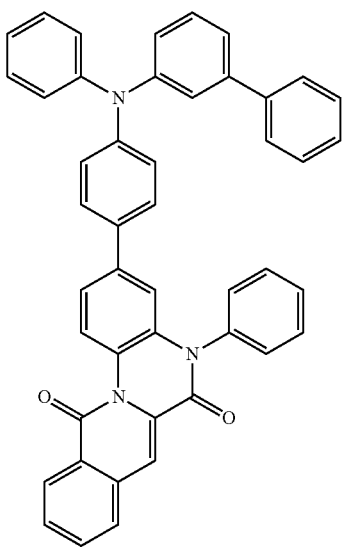 [SMILES: O=c1c2cc3ccccc3c(=O)n2c2ccc(-c3ccc(N(c4ccccc4)c4cccc(-c5ccccc5)c4)cc3)cc2n1-c1ccccc1]
79

| 80 | 82 |
|---|---|
| 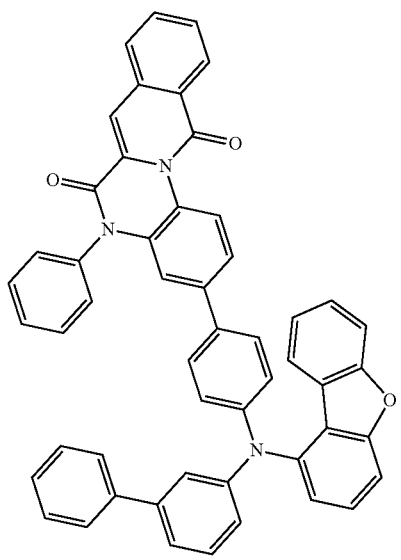 [SMILES: O=c1c2cc3ccccc3c(=O)n2c2ccc(-c3ccc(N(c4cccc(-c5ccccc5)c4)c4cccc5oc6ccccc6c45)cc3)cc2n1-c1ccccc1] | 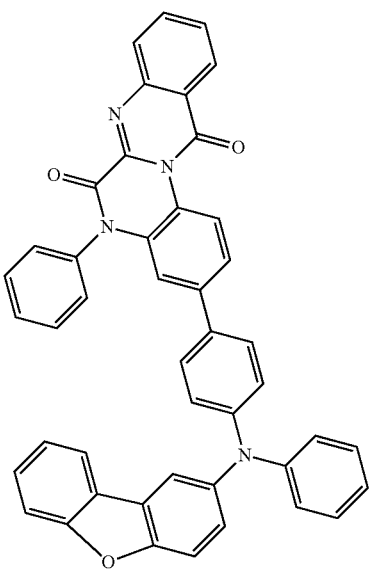 |
| 81 | 83 |
|---|---|
| 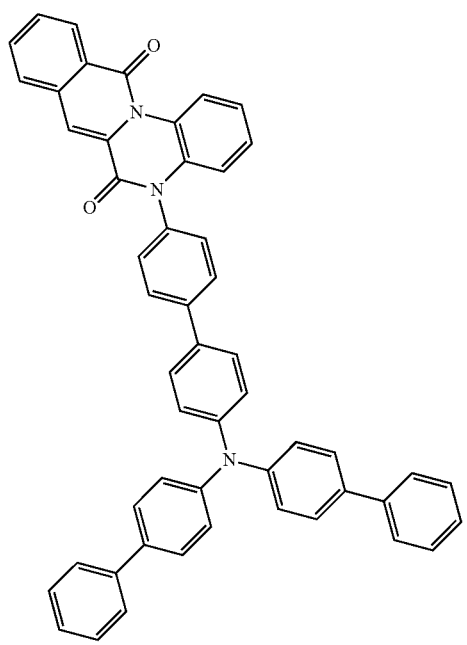 [SMILES: O=c1c2cc3ccccc3c(=O)n2c2ccccc2n1-c1ccc(-c2ccc(N(c3ccc(-c4ccccc4)cc3)c3ccc(-c4ccccc4)cc3)cc2)cc1] | 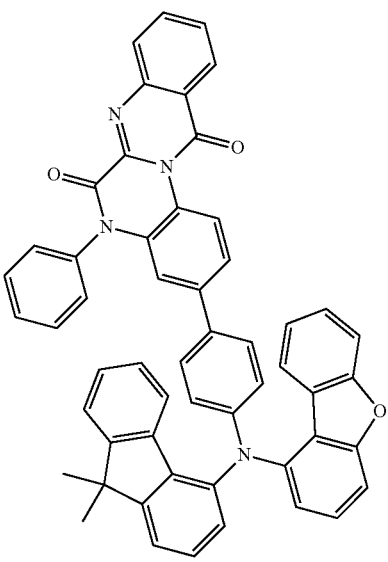 [SMILES: CC1(C)c2ccccc2-c2c(N(c3ccc(-c4ccc5c(c4)n(-c4ccccc4)c(=O)c4nc6ccccc6c(=O)n45)cc3)c3cccc4oc5ccccc5c34)cccc21] |

| 51 -continued | 52 -continued |
|---|---|
| 84 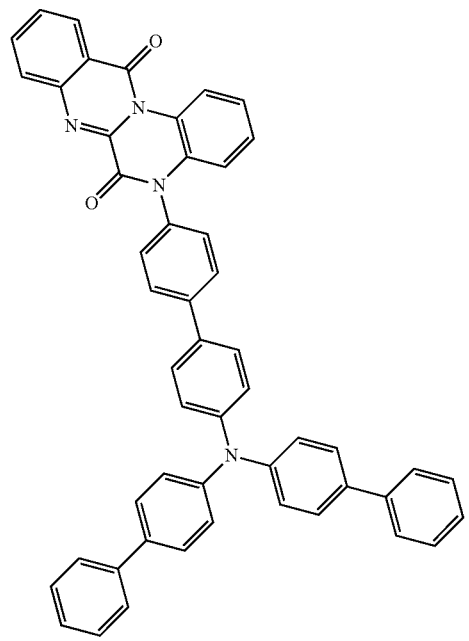 [SMILES: O=c1c2nc3ccccc3c(=O)n2c2ccccc2n1-c1ccc(-c2ccc(N(c3ccc(-c4ccccc4)cc3)c3ccc(-c4ccccc4)cc3)cc2)cc1] | 86 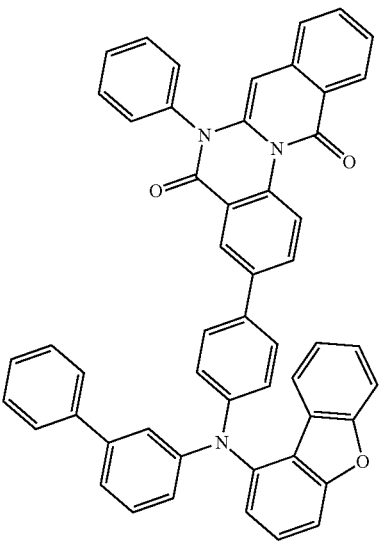 |
| 85 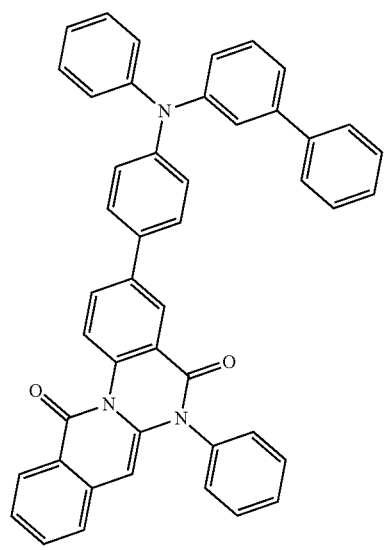 [SMILES: O=c1c2cc(-c3ccc(N(c4ccccc4)c4cccc(-c5ccccc5)c4)cc3)ccc2n2c(=O)c3ccccc3cc2n1-c1ccccc1] | 87 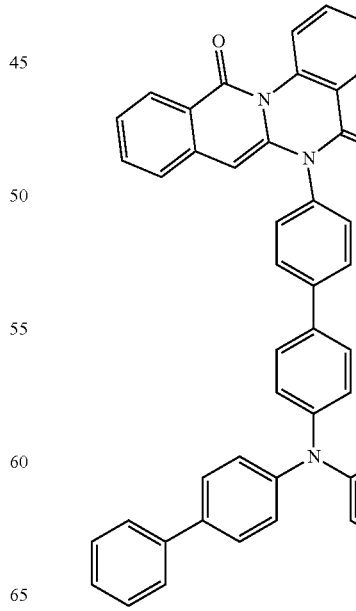 |

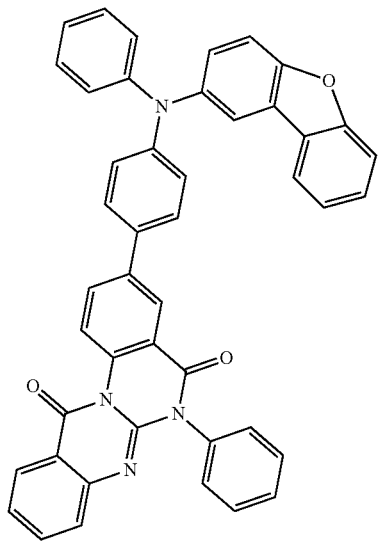 [SMILES: O=c1c2cc(-c3ccc(N(c4ccccc4)c4ccc5oc6ccccc6c5c4)cc3)ccc2n2c(=O)c3ccccc3nc2n1-c1ccccc1]
88
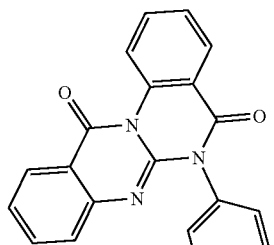
89
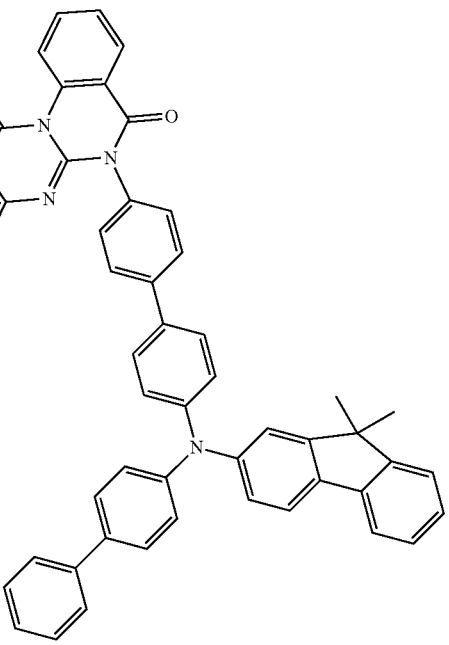
90
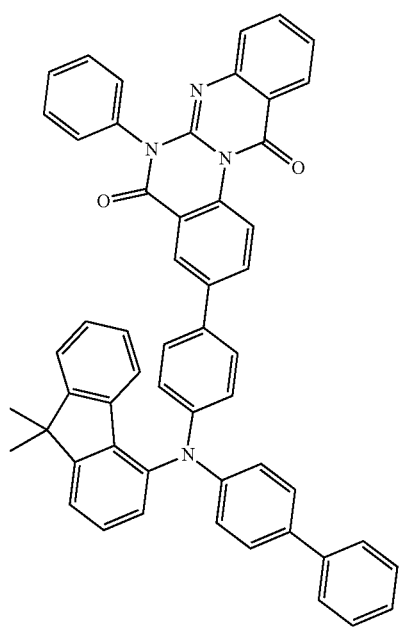 [SMILES: CC1(C)c2ccccc2-c2c(N(c3ccc(-c4ccccc4)cc3)c3ccc(-c4ccc5c(c4)c(=O)n(-c4ccccc4)c4nc6ccccc6c(=O)n54)cc3)cccc21]
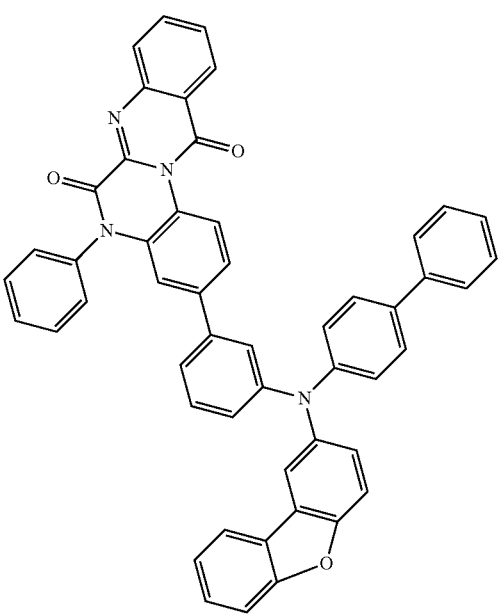 [SMILES: O=c1c2nc3ccccc3c(=O)n2c2ccc(-c3cccc(N(c4ccc(-c5ccccc5)cc4)c4ccc5oc6ccccc6c5c4)c3)cc2n1-c1ccccc1]
91

| 55 -continued | 56 -continued |
|---|---|
| 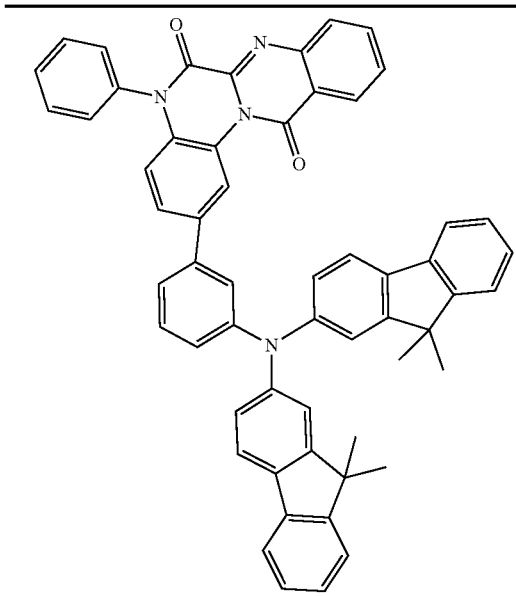 92 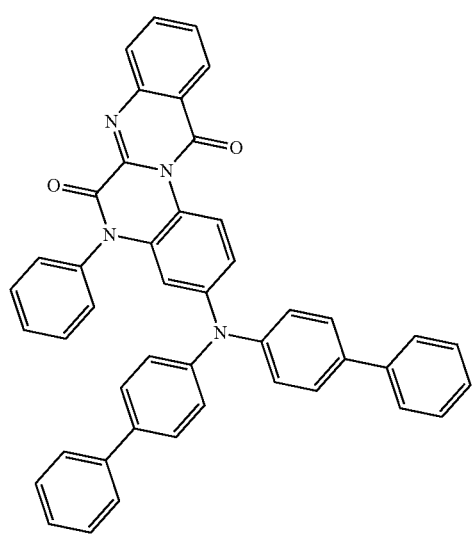 [SMILES: O=c1c2nc3ccccc3c(=O)n2c2ccc(N(c3ccc(-c4ccccc4)cc3)c3ccc(-c4ccccc4)cc3)cc2n1-c1ccccc1] 93 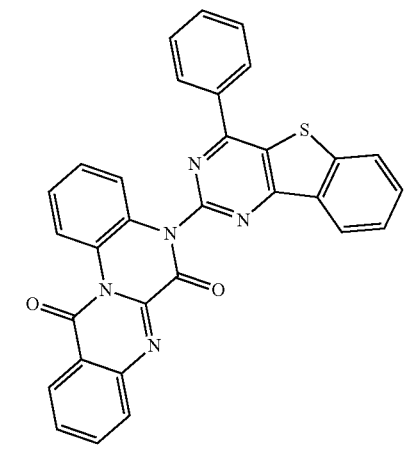 [SMILES: O=c1c2nc3ccccc3c(=O)n2c2ccccc2n1-c1nc(-c2ccccc2)c2sc3ccccc3c2n1] 94 | 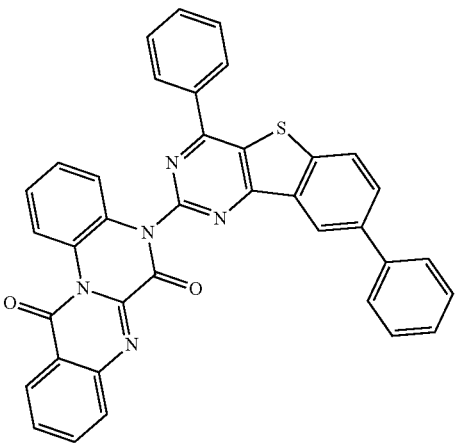 [SMILES: O=c1c2nc3ccccc3c(=O)n2c2ccccc2n1-c1nc(-c2ccccc2)c2sc3ccc(-c4ccccc4)cc3c2n1] 95 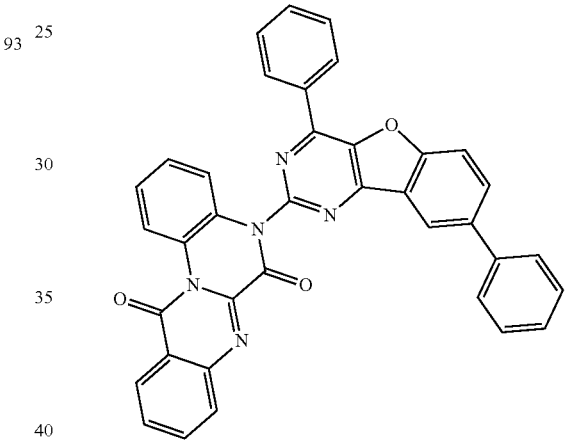 96 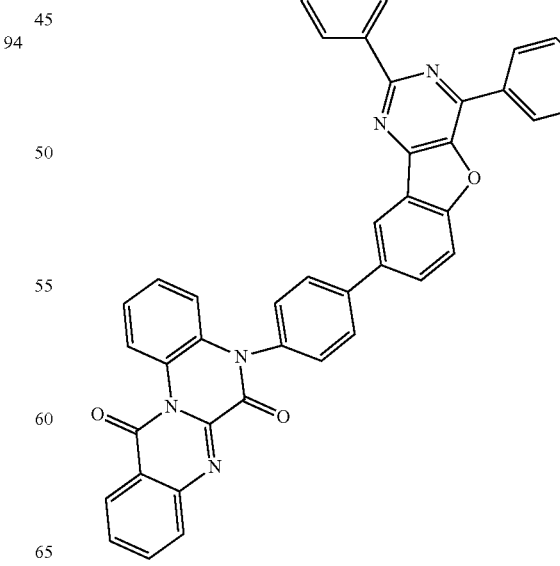 97 |

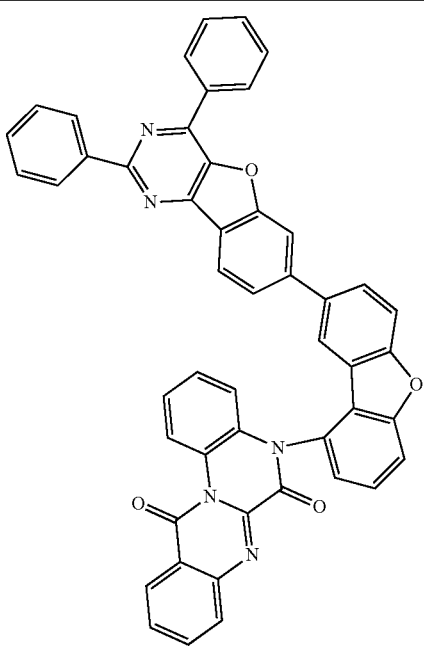

98

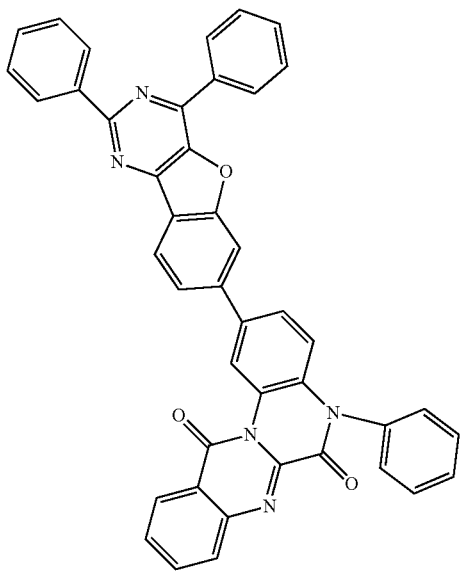 [SMILES: O=c1c2nc3ccccc3c(=O)n2c2cc(-c3ccc4c(c3)oc3c(-c5ccccc5)nc(-c5ccccc5)nc34)ccc2n1-c1ccccc1]

99

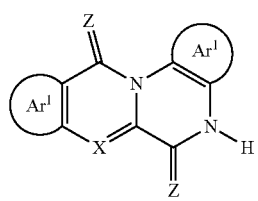

Formula (IV-Int)

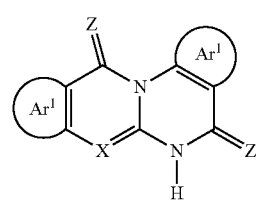

Formula (V-Int)

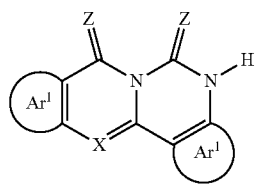

Formula (VI-Int)

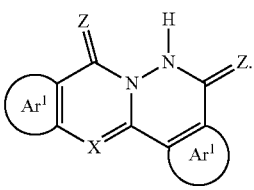

Formula (VII-Int)

Illustrative syntheses of the base skeletons of the formulae (IV-Int) to (VII-Int) are shown below:

Scheme 1 shows the synthesis of the base skeleton of the formula (V-Int).

Scheme 1

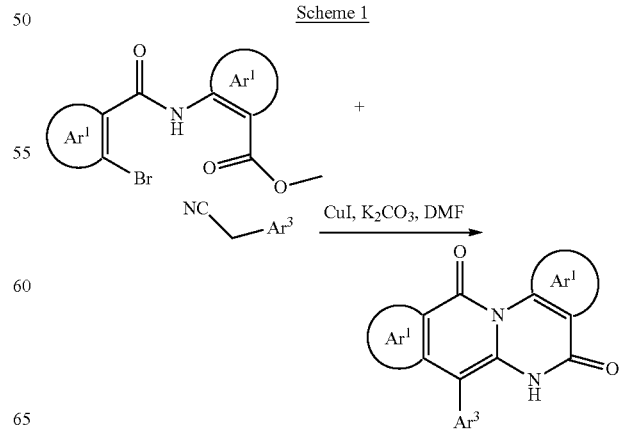

The compounds of the formula (I) can be prepared by means of known synthesis steps from organic chemistry, for example bromination, Suzuki coupling and Hartwig-Buchwald coupling. Some preferred synthesis methods are shown below by way of example. These can be modified by the person skilled in the art within the scope of their common knowledge and should not be interpreted in a limiting manner.

In a preferred process for preparing the compounds of the formula (I), in a first step, the base skeleton is prepared, which conforms to one of the formulae (IV-Int) to (VII-Int):

Scheme 2 shows the synthesis of the base skeleton of the formula (VI-Int).

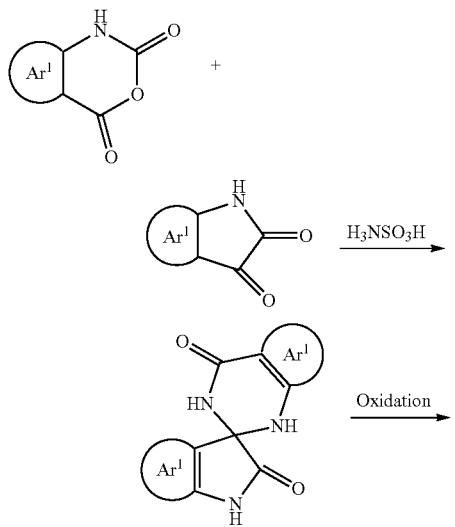

After the synthesis of the main structure of one of the formulae (IV-Int) to (VII-Int), an aromatic system is bonded to the free nitrogen atom of the intermediate of formula (IV-Int) to (VII-Int) in an organometallic coupling reaction, preferably an Ullmann reaction or a Buchwald reaction.

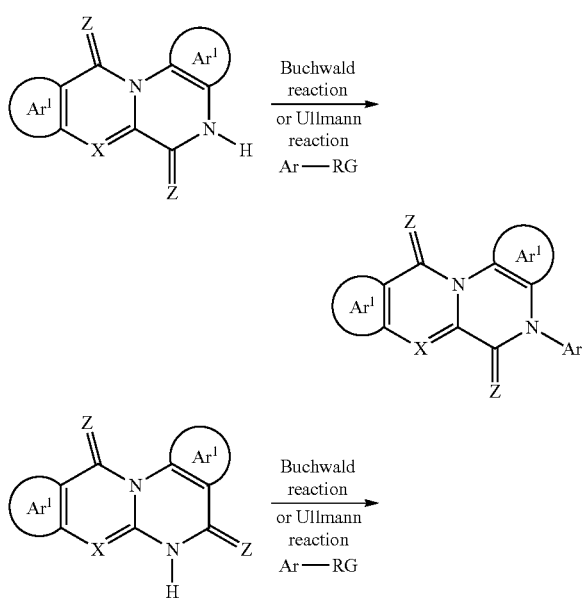

Ar in the abovementioned schemes is an optionally substituted aromatic or heteroaromatic system. RG is a reactive group, preferably halogen.

In a further optional step (scheme 4), the compound of the formula (I) obtained in the abovementioned scheme may be halogenated on one of the rings and then bound to an aromatic or heteroaromatic system in this position in a Suzuki reaction:

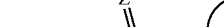

-continued

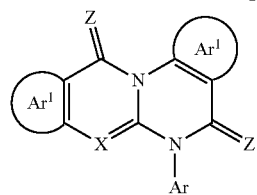

1) Halogenation
2) Suzuki reation
   Ar-RG

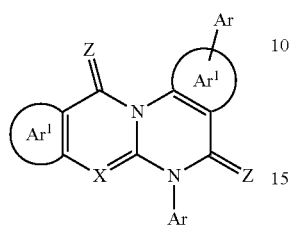

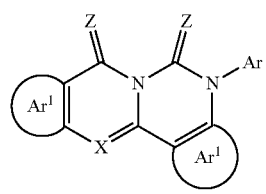

1) Halogenation
2) Suzuki reation
   Ar-RG

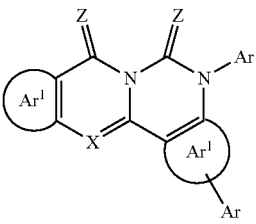

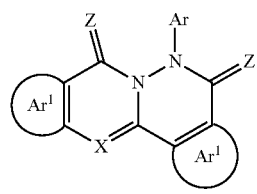

1) Halogenation
2) Suzuki reation
   Ar-RG

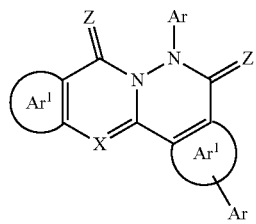

Ar in the abovementioned schemes is an optionally substituted aromatic or heteroaromatic system. RG is a reactive group, preferably halogen.

The present application thus provides a process for preparing a compound of formula (I), characterized in that an intermediate of one of the formulae (IV-Int) to (VII-Int) is first prepared, preferably by a ring closure reaction, and in that, in an Ullmann reaction or a Buchwald reaction, an aromatic or heteroaromatic system is then introduced in the position of the $Ar^2$ group in the formula (I). In a preferred embodiment, a halogenation reaction, preferably a bromination reaction, is then conducted on one of the $Ar^1$ rings, which introduces a halogen substituent, specifically a bromine substituent, in one of the $Ar^1$ rings, and then a Suzuki reaction is conducted, in which an aromatic system is introduced in the position of the halogen substituent, specifically the bromine substituent.

Scheme 5 below, finally, shows a process for synthesizing a compound of the formula (I) in one step:

Scheme 5

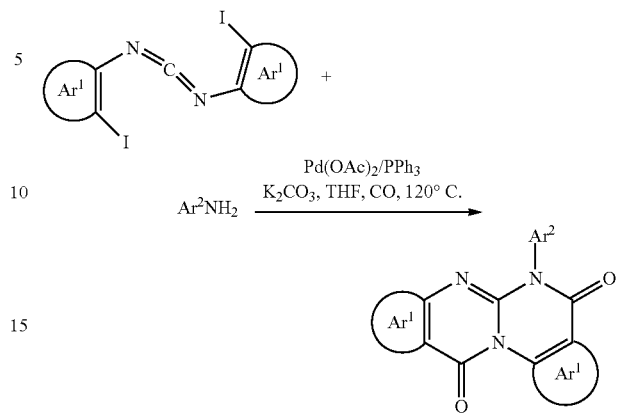

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation comprising a compound of a formula (I)

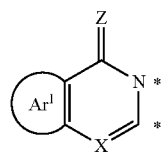

where a unit of formula (II) or formula (III) is bonded at the bonding sites labeled * in the ring, in each case via the bonds labeled *,

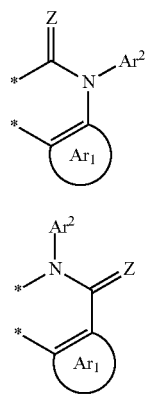

Formula (II)

Formula (III)

and where the variables that occur are as follows:

X is N or $CAr^3$;

Z is the same or different at each instance and is selected from O and S;

$Ar^1$ is the same or different at each instance and is selected from fused-on aromatic ring systems having 6 to 40 aromatic ring atoms, and fused-on heteroaromatic ring systems having 5 to 40 aromatic ring atoms, where the aromatic ring systems and heteroaromatic ring systems are each substituted by $R^1$ radicals;

$Ar^2$ is selected from branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where the groups mentioned are each substituted by one or more $R^2$ radicals;

$Ar^3$ is selected from H, D, F, Cl, Br, I, $C(=O)R^3$, CN, $Si(R^3)_3$, $N(R^3)_2$, $P(=O)(R^3)_2$, $OR^3$, $S(=O)R^3$, $S(=O)_2R^3$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where the alkyl, alkoxy, alkenyl and alkynyl groups mentioned and the aromatic ring systems and heteroaromatic ring systems mentioned are each substituted by $R^3$ radicals; and where one or more $CH_2$ groups in the alkyl, alkoxy, alkenyl and alkynyl groups mentioned may be replaced by $-R^3C=CR^3-$, $-C\equiv C-$, $Si(R^3)_2$, $C=O$, $C=NR^3$, $-C(=O)O-$, $-C(=O)NR^3-$, $NR^3$, $P(=O)(R^3)$, $-O-$, $-S-$, SO or $SO_2$, $R^1$ is the same or different at each instance and is selected from H, D, F, Cl, Br, I, $C(=O)R^4$, CN, $Si(R^4)_3$, $N(R^4)_2$, $P(=O)(R^4)_2$, $OR^4$, $S(=O)R^4$, $S(=O)_2R^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ radicals may be joined to one another and may form a ring; where the alkyl, alkoxy, alkenyl and alkynyl groups mentioned and the aromatic ring systems and heteroaromatic ring systems mentioned are each substituted by $R^4$ radicals; and where one or more $CH_2$ groups in the alkyl, alkoxy, alkenyl and alkynyl groups mentioned may be replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, SO or $SO_2$, $R^2$ is the same or different at each instance and is selected from H, D, F, Cl, Br, I, $C(=O)R^4$, CN, $Si(R^4)_3$, $N(R^4)_2$, $P(=O)(R^4)_2$, $OR^4$, $S(=O)R^4$, $S(=O)_2R^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^2$ radicals may be joined to one another and may form a ring; where the alkyl, alkoxy, alkenyl and alkynyl groups mentioned and the aromatic ring systems and heteroaromatic ring systems mentioned are each substituted by $R^4$ radicals; and where one or more $CH_2$ groups in the alkyl, alkoxy, alkenyl and alkynyl groups mentioned may be replaced by $-R^4C=CR^4-$, $-C\equiv C-$, $Si(R^4)_2$, $C=O$, $C=NR^4$, $-O(=O)O-$, $-C(=O)NR^4-$, $NR^4$, $P(=O)(R^4)$, $-O-$, $-S-$, SO or $SO_2$;

$R^3$ is the same or different at each instance and is selected from H, D, F, Cl, Br, I, $C(=O)R^4$, CN, $Si(R^4)_3$, $N(R^4)_2$, $P(=O)(R^4)_2$, $OR^4$, $S(=O)R^4$, $S(=O)_2R^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^3$ radicals may be joined to one another and may form a ring; where the alkyl, alkoxy, alkenyl and alkynyl groups mentioned and the aromatic ring systems and heteroaromatic ring systems mentioned are each substituted by $R^4$ radicals; and where one or more $CH_2$ groups in the alkyl, alkoxy, alkenyl and alkynyl groups mentioned may be replaced by $-R^4C=CR^4-$, $-C\equiv C-$, $Si(R^4)_2$, $C=O$, $C=NR^4$, $-C(=O)O-$, $-C(=O)NR^4-$, $NR^4$, $P(=O)(R^4)$, $-O-$, $-S-$, SO or $SO_2$, $R^4$ is the same or different at each instance and is selected from H, D, F, Cl, Br, I, $C(=O)R^5$, CN, $Si(R^5)_3$, $N(R^5)_2$, $P(=O)(R^5)_2$, $OR^5$, $S(=O)R^5$, $S(=O)_2R^5$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^4$ radicals may be joined to one another and may form a ring; where the alkyl, alkoxy, alkenyl and alkynyl groups mentioned and the aromatic ring systems and heteroaromatic ring systems mentioned are each substituted by $R^5$ radicals; and where one or more $CH_2$ groups in the alkyl, alkoxy, alkenyl and alkynyl groups mentioned may be replaced by $-R^5C=CR^5-$, $-C\equiv C-$, $Si(R^5)_2$, $C=O$, $C=NR^5$, $-O(=O)O-$, $-C(=O)NR^5-$, $NR^5$, $P(=O)(R^5)$, $-O-$, $-S-$, SO or $SO_2$;

$R^5$ is the same or different at each instance and is selected from H, D, F, Cl, Br, I, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more R⁵ radicals may be joined to one another and may form a ring; and where the alkyl, alkoxy, alkenyl and alkynyl groups, aromatic ring systems and heteroaromatic ring systems mentioned may be substituted by one or more radicals selected from F and ON; and at least one further compound.

The further compound may, for example, be a solvent, especially one of the abovementioned solvents or a mixture of these solvents. The further compound may alternatively be at least one further organic or inorganic compound which is likewise used in the electronic device, for example an emitting compound and/or a further matrix material. Suitable emitting compounds and further matrix materials are listed at the back in connection with the organic electroluminescent device. This further compound may also be polymeric.

The compounds of the invention are suitable for use in an electronic device, especially in an organic electroluminescent device. The present invention therefore further provides for the use of an inventive compound of the formula (I) as defined above in connection with the formulation according to the application in an electronic device, especially in an organic electroluminescent device.

The present invention still further provides an electronic device comprising at least one compound of the formula (I)

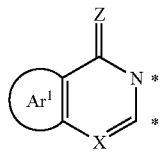

where a unit of formula (II) or formula (III) is bonded at the bonding sites labeled * in the ring, in each case via the bonds labeled *, Formula (II)

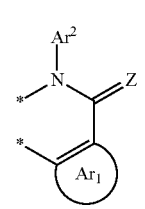

Formula (III)

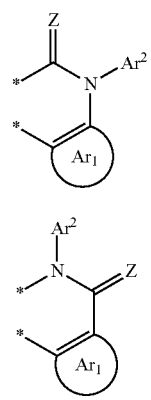

and where the variables that occur are as follows:

X is N or CAr³;

Z is the same or different at each instance and is selected from O and S;

Ar¹ is the same or different at each instance and is selected from fused-on aromatic ring systems having 6 to 40 aromatic ring atoms, and fused-on heteroaromatic ring systems having 5 to 40 aromatic ring atoms, where the aromatic ring systems and heteroaromatic ring systems are each substituted by $R^1$ radicals;

Ar² is selected from branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where the groups mentioned are each substituted by one or more $R^2$ radicals;

Ar³ is selected from H, D, F, Cl, Br, I, C(=O)R³, CN, Si(R³)₃, N(R³)₂, P(=O)(R³)₂, OR³, S(=O)R³, S(=O)₂R³, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where the alkyl, alkoxy, alkenyl and alkynyl groups mentioned and the aromatic ring systems and heteroaromatic ring systems mentioned are each substituted by R³ radicals; and where one or more CH₂ groups in the alkyl, alkoxy, alkenyl and alkynyl groups mentioned may be replaced by —R³C=CR³—, —C≡C—, Si(R³)₂, C=O, C=NR³, —C(=O)O—, —C(=O)NR³—, NR³, P(=O)(R³), —O—, —S—, SO or SO₂;

R¹ is the same or different at each instance and is selected from H, D, F, Cl, Br, I, C(=O)R⁴, CN, Si(R⁴)₃, N(R⁴)₂, P(=O)(R⁴)₂, OR⁴, S(=O)R⁴, S(=O)₂R⁴, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R¹ radicals may be joined to one another and may form a ring; where the alkyl, alkoxy, alkenyl and alkynyl groups mentioned and the aromatic ring systems and heteroaromatic ring systems mentioned are each substituted by R⁴ radicals; and where one or more CH₂ groups in the alkyl, alkoxy, alkenyl and alkynyl groups mentioned may be replaced by —R⁴C=CR⁴—, —C≡C—, Si(R⁴)₂, C=O, C=NR⁴, —C(=O)O—, —C(=O)NR⁴—, NR⁴, P(=O)(R⁴), —O—, —S—, SO or SO₂;

R² is the same or different at each instance and is selected from H, D, F, Cl, Br, I, C(=O)R⁴, CN, Si(R⁴)₃, N(R⁴)₂, P(=O)(R⁴)₂, OR⁴, S(=O)R⁴, S(=O)₂R⁴, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R² radicals may be joined to one another and may form a ring; where the alkyl, alkoxy, alkenyl and alkynyl groups mentioned and the aromatic ring systems and heteroaromatic ring systems mentioned are each substituted by R⁴ radicals; and where one or more CH₂ groups in the alkyl, alkoxy, alkenyl and alkynyl groups mentioned may be replaced by —R⁴C=CR⁴—, —C≡C—, Si(R⁴)₂, C=O, C=NR⁴, —C(=O)O—, —C(=O)NR⁴—, NR⁴, P(=O)(R⁴), —O—, —S—, SO or SO₂;

R³ is the same or different at each instance and is selected from H, D, F, Cl, Br, I, C(=O)R⁴, CN, Si(R⁴)₃, N(R⁴)₂, P(=O)(R⁴)₂, OR⁴, S(=O)R⁴, S(=O)₂R⁴, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^3$ radicals may be joined to one another and may form a ring; where the alkyl, alkoxy, alkenyl and alkynyl groups mentioned and the aromatic ring systems and heteroaromatic ring systems mentioned are each substituted by $R^4$ radicals; and where one or more $CH_2$ groups in the alkyl, alkoxy, alkenyl and alkynyl groups mentioned may be replaced by —$R^4C=CR^4$—, —$C\equiv C$—, $Si(R^4)_2$, $C=O$, $C=NR^4$, —$C(=O)O$—, —$C(=O)NR^4$—, $NR^4$, $P(=O)(R^4)$, —O—, —S—, SO or $SO_2$;

$R^4$ is the same or different at each instance and is selected from H, D, F, Cl, Br, I, $C(=O)R^5$, CN, $Si(R^5)_3$, $N(R^5)_2$, $P(=O)(R^5)_2$, $OR^5$, $S(=O)R^5$, $S(=O)_2R^5$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^4$ radicals may be joined to one another and may form a ring; where the alkyl, alkoxy, alkenyl and alkynyl groups mentioned and the aromatic ring systems and heteroaromatic ring systems mentioned are each substituted by $R^5$ radicals; and where one or more $CH_2$ groups in the alkyl, alkoxy, alkenyl and alkynyl groups mentioned may be replaced by —$R^5C=CR^5$—, —$C\equiv C$—, $Si(R^5)_2$, $C=O$, $C=NR^5$, —$O(=O)O$—, —$C(=O)NR^5$—, $NR^5$, $P(=O)(R^5)$, —O—, —S—, SO or $SO_2$;

$R^5$ is the same or different at each instance and is selected from H, D, F, Cl, Br, I, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^5$ radicals may be joined to one another and may form a ring; and where the alkyl, alkoxy, alkenyl and alkynyl groups, aromatic ring systems and heteroaromatic ring systems mentioned may be substituted by one or more radicals selected from F and CN.

An electronic device in the context of the present invention is a device comprising at least one layer comprising at least one organic compound. This component may also comprise inorganic materials or else layers formed entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitized organic solar cells (DSSCs), organic optical detectors, organic photoreceptors, organic field-quench devices (O-FQDs), light-emitting electrochemical cells (LECs), organic laser diodes (O-lasers) and organic plasmon emitting devices, but preferably organic electroluminescent devices (OLEDs), more preferably phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission. The organic electroluminescent device of the invention may also be a tandem OLED, especially for white-emitting OLEDs.

The compound of the invention according to the above-detailed embodiments may be used in different layers, according to the exact structure. Preference is given to an organic electroluminescent device comprising a compound of formula (I) or the above-recited preferred embodiments in an emitting layer as matrix material for one or more phosphorescent emitters or for emitters that exhibit TADF (thermally activated delayed fluorescence), especially for phosphorescent emitters. In this case, the organic electroluminescent device may contain an emitting layer, or it may contain a plurality of emitting layers, where at least one emitting layer contains at least one compound of the invention as matrix material. In addition, the compound of the invention can also be used in an electron transport layer and/or in a hole blocker layer and/or in a hole transport layer and/or in an exciton blocker layer.

When the compound of the invention is used as matrix material for a phosphorescent compound in an emitting layer, it is preferably used in combination with one or more phosphorescent materials (triplet emitters). Phosphorescence in the context of this invention is understood to mean luminescence from an excited state having higher spin multiplicity, i.e. a spin state >1, especially from an excited triplet state. In the context of this application, all luminescent complexes with transition metals or lanthanides, especially all iridium, platinum and copper complexes, shall be regarded as phosphorescent compounds.

The mixture of the compound of the invention and the emitting compound contains between 99% and 1% by volume, preferably between 98% and 10% by volume, more preferably between 97% and 60% by volume and especially between 95% and 80% by volume of the compound of the invention, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

A further preferred embodiment of the present invention is the use of the compound of the invention as matrix material for a phosphorescent emitter in combination with a further matrix material. Suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/

288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, triphenylene derivatives, for example according to WO 2012/048781, or dibenzofuran derivatives, for example according to WO 2015/169412, WO 2016/015810, WO 2016/023608, WO 2017/148564 or WO 2017/148565. It is likewise possible for a further phosphorescent emitter having shorter-wavelength emission than the actual emitter to be present as co-host in the mixture, or a compound not involved in charge transport to a significant extent, if at all, as described, for example, in WO 2010/108579.

In a preferred embodiment of the invention, the materials are used in combination with a further matrix material. Preferred co-matrix materials, especially when the compound of the invention is substituted by an electron-deficient heteroaromatic ring system, are selected from the group of the biscarbazoles, the bridged carbazoles, the triarylamines, the dibenzofuranyl-carbazole derivatives or dibenzofuranyl-amine derivatives and the carbazoleamines.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the emitters described above can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439, WO 2018/011186 and WO 2018/041769, WO 2019/020538, WO 2018/178001 and as yet unpublished patent applications EP 17206950.2 and EP 18156388.3. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Examples of phosphorescent dopants are adduced below.

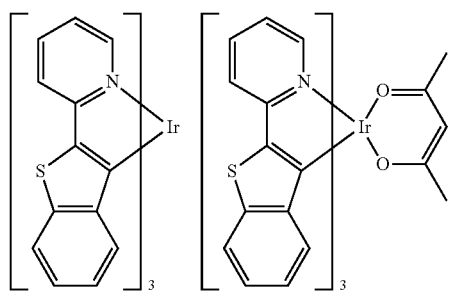

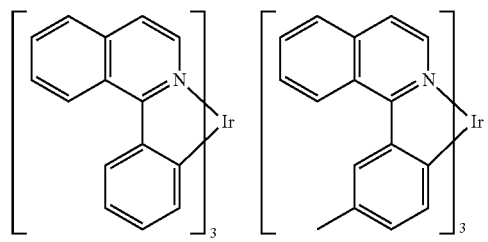

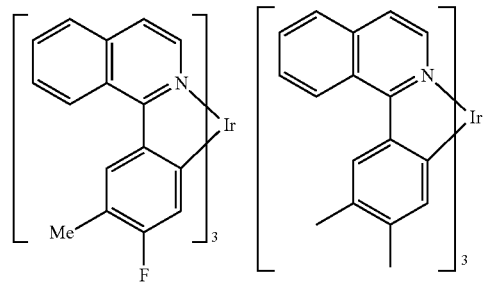

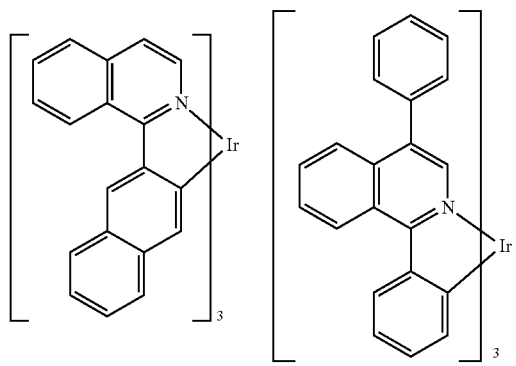

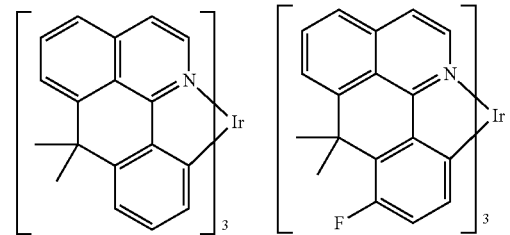

71
-continued
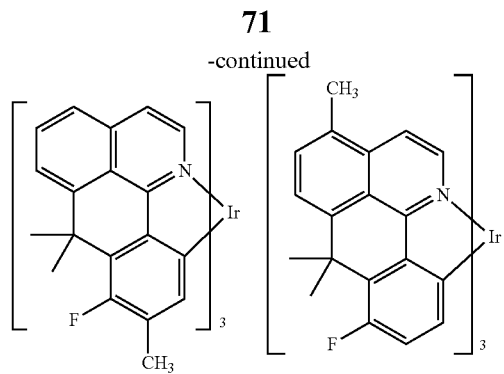
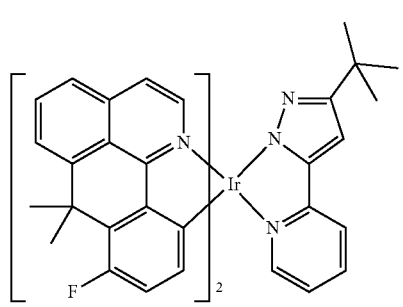
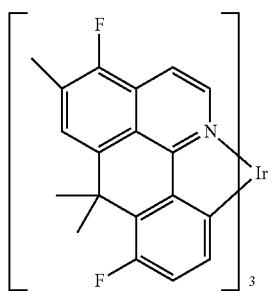
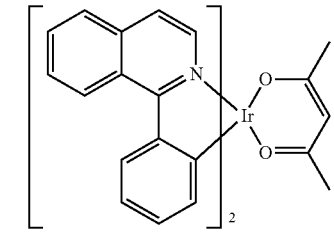
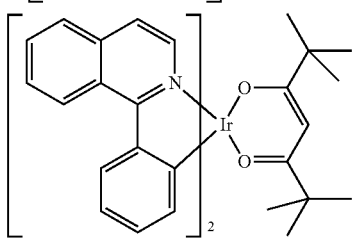
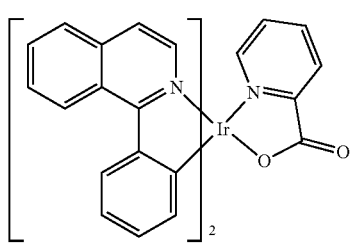
72
-continued
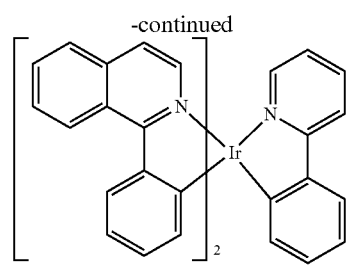
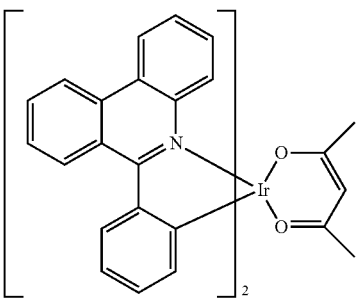
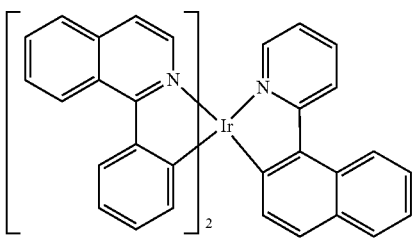
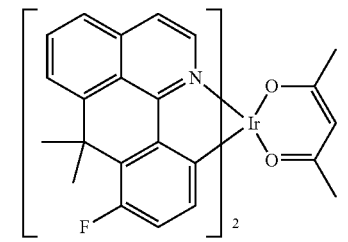
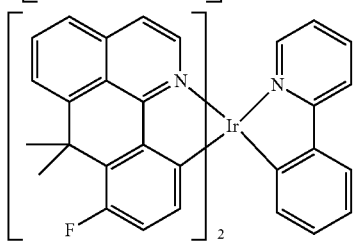
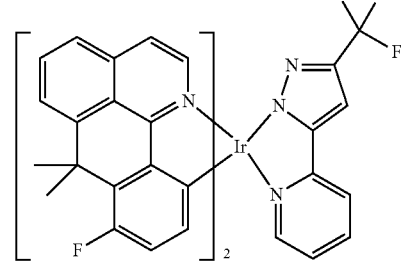

73
-continued
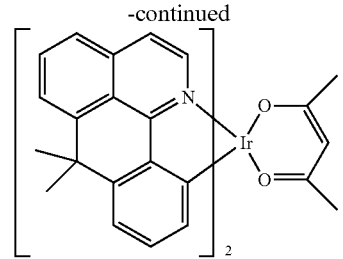
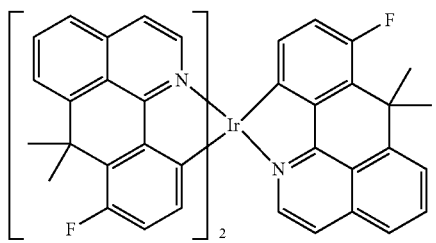
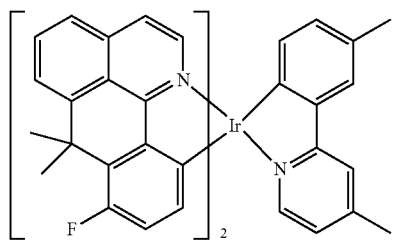
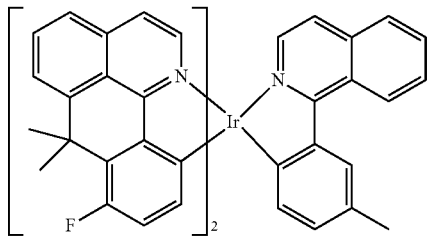
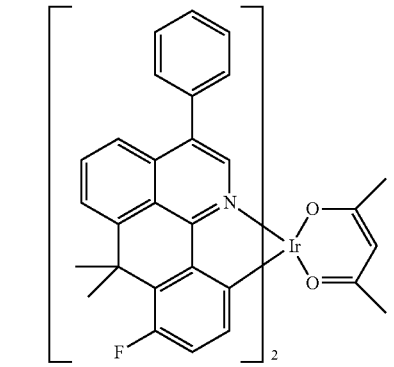
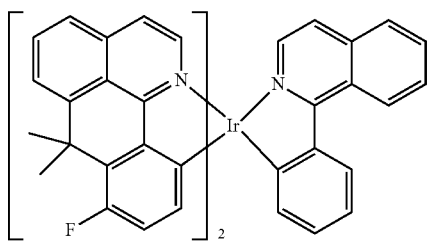
74
-continued
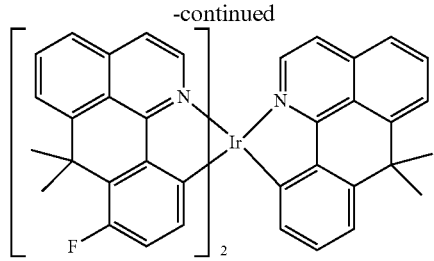
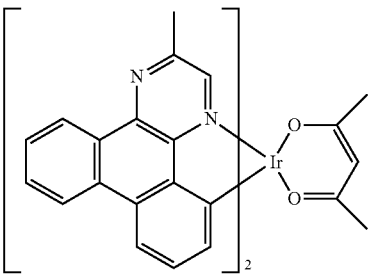
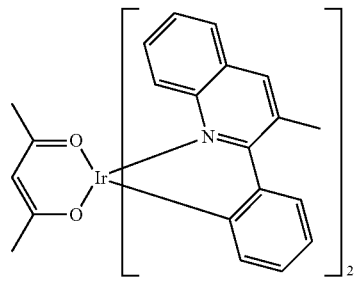
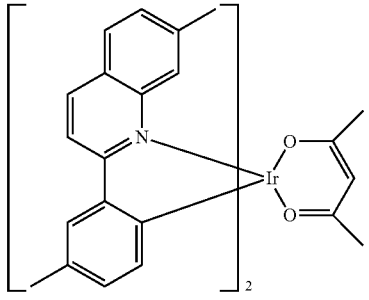
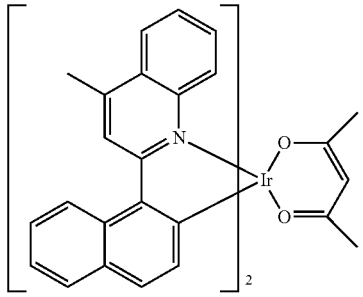
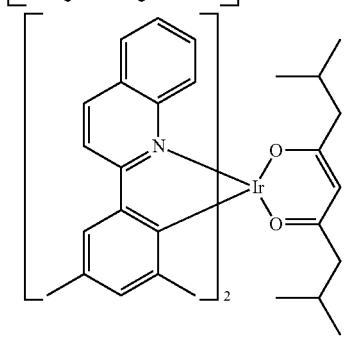

-continued
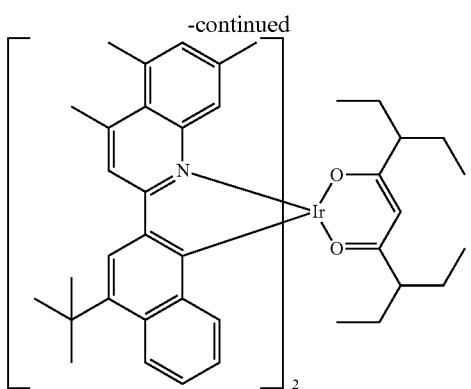
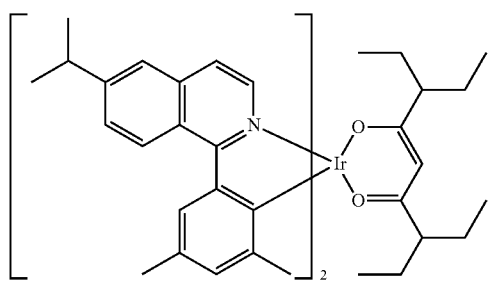
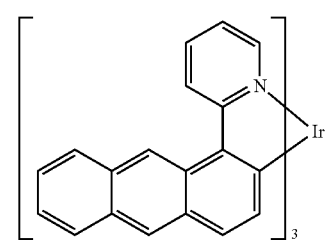
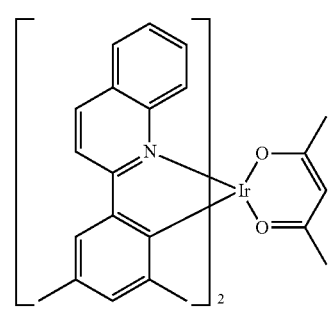
-continued
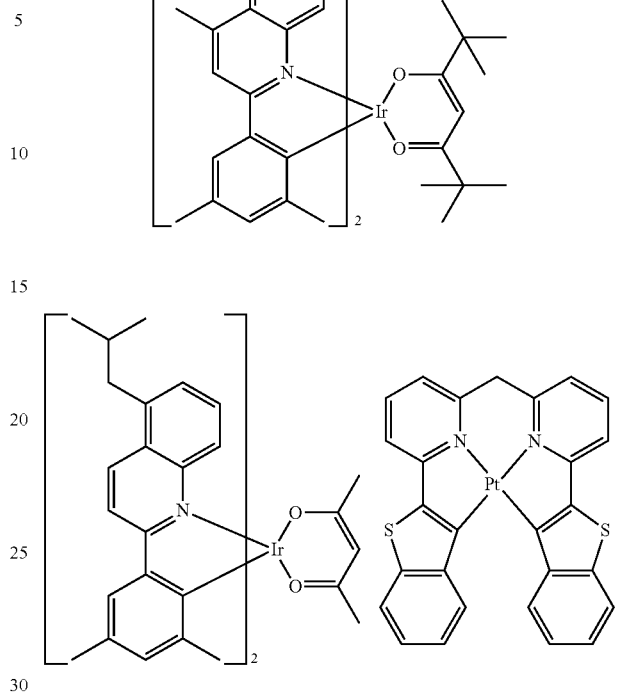
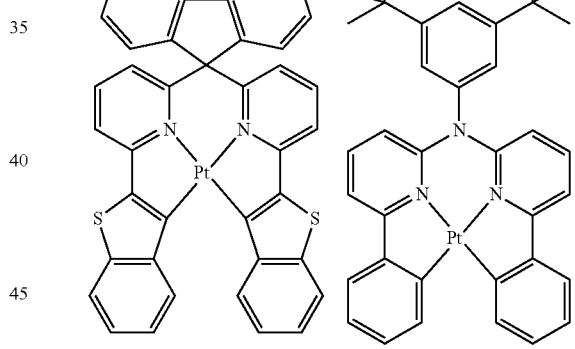
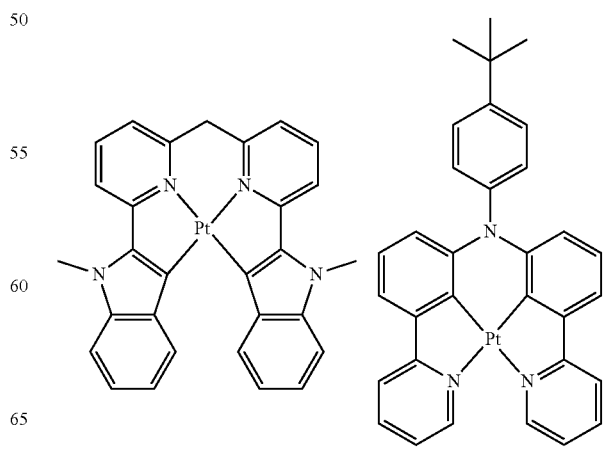

-continued
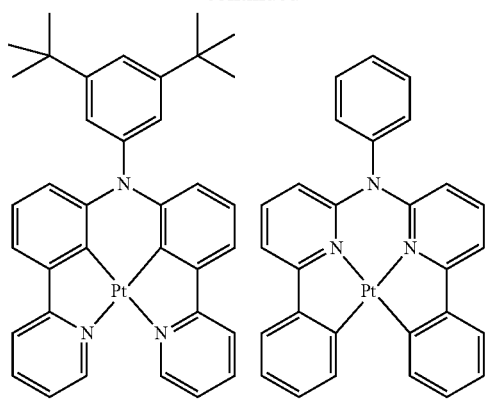
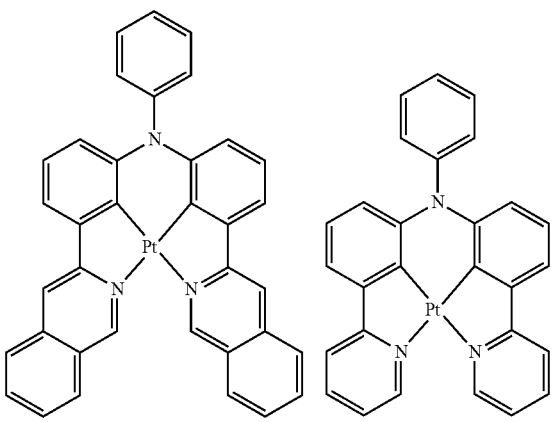
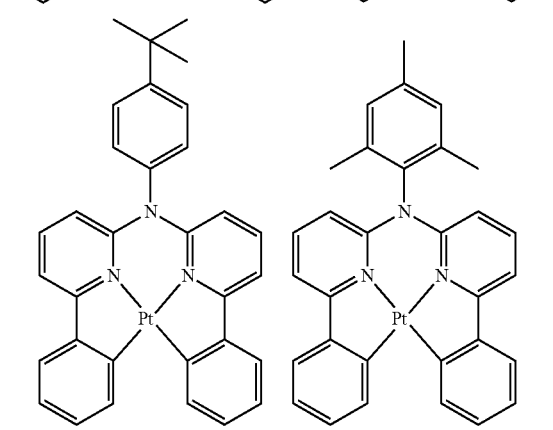
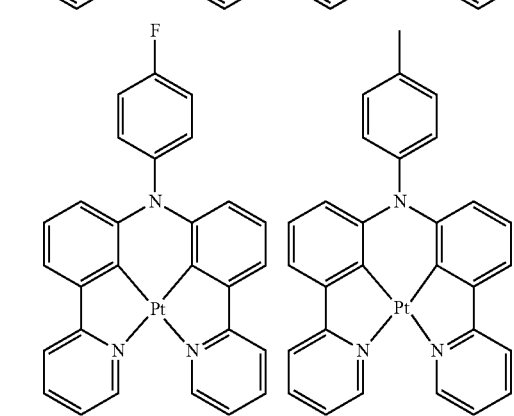
-continued
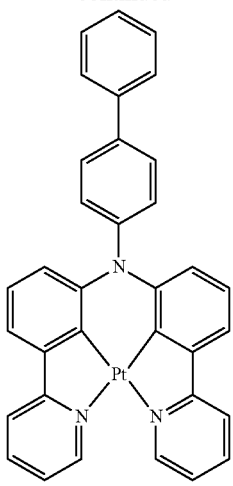
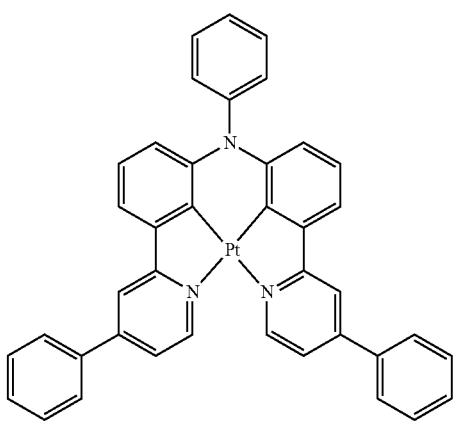
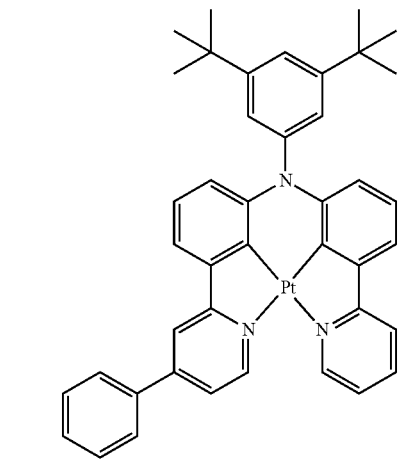

-continued
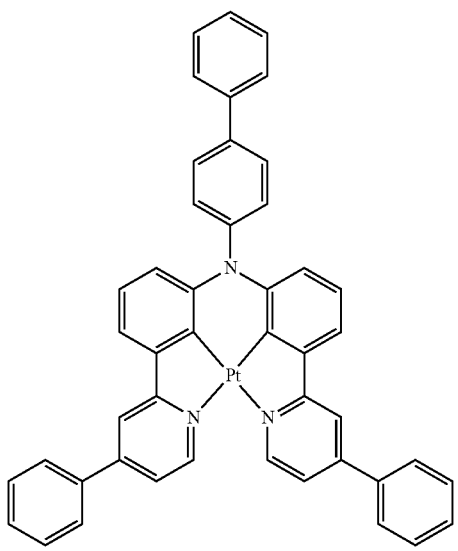
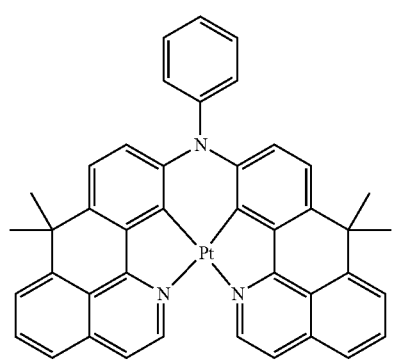
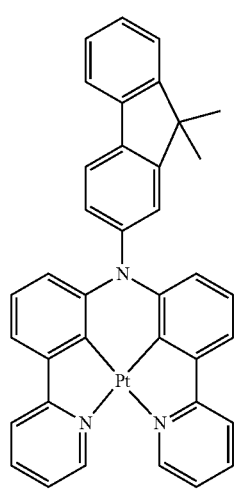
-continued
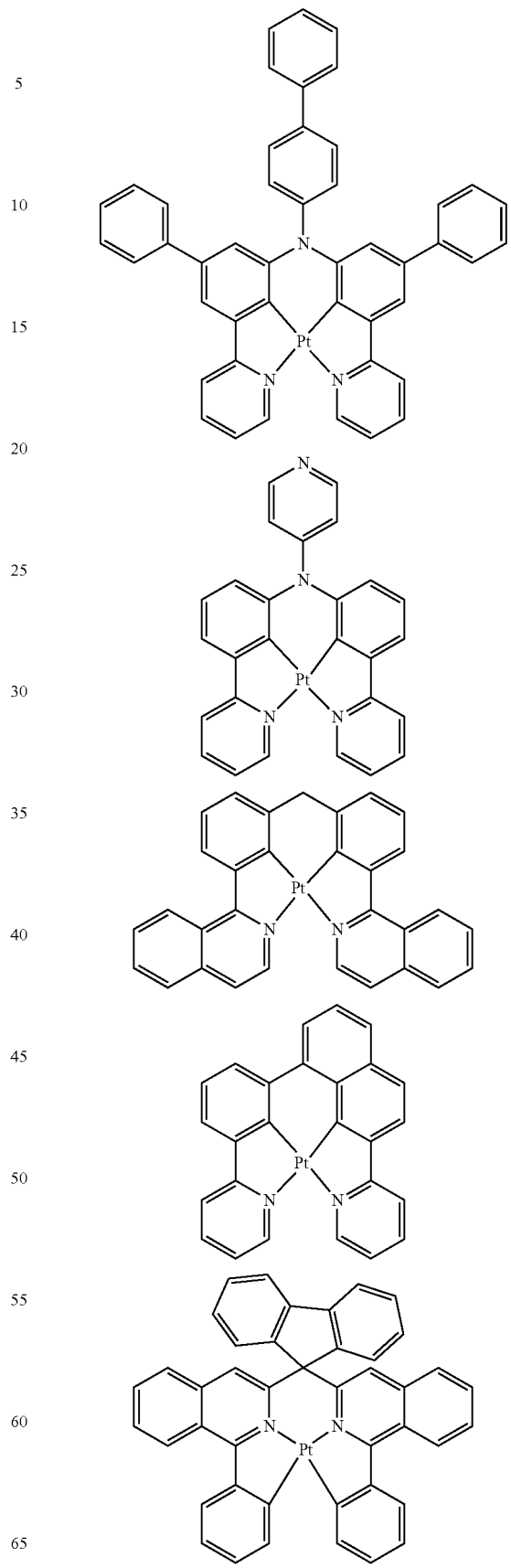

-continued
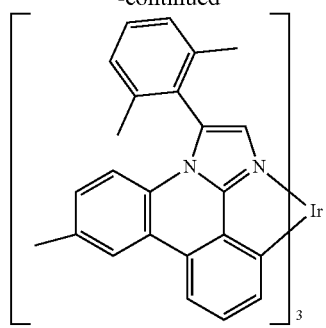
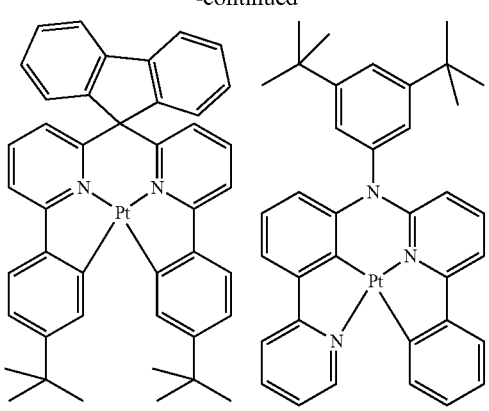
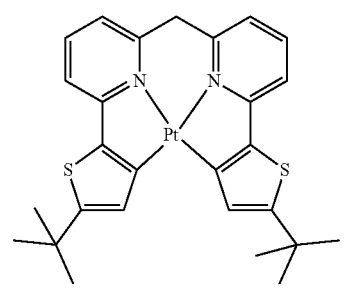
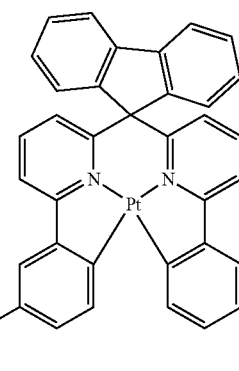
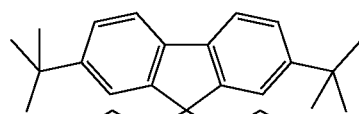
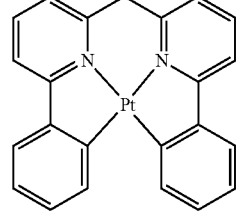
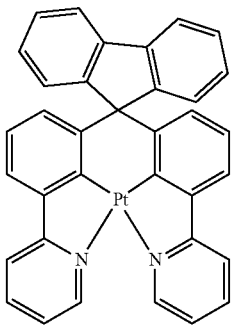
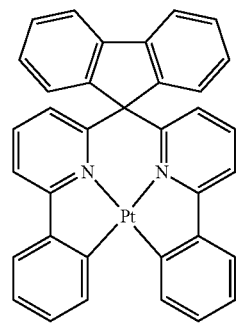
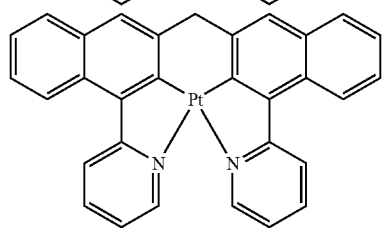
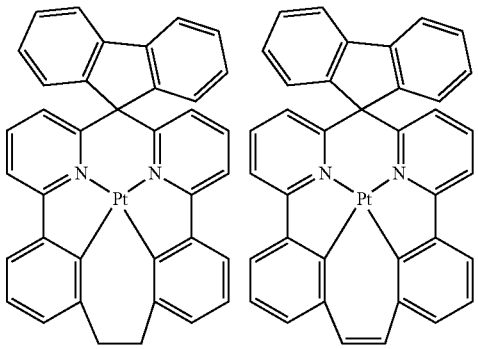

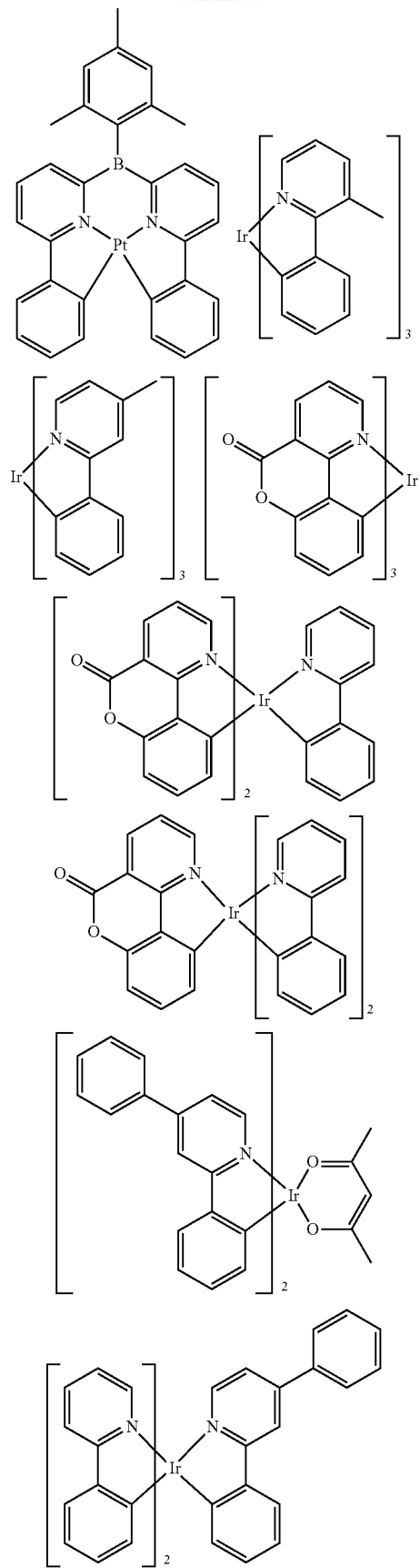
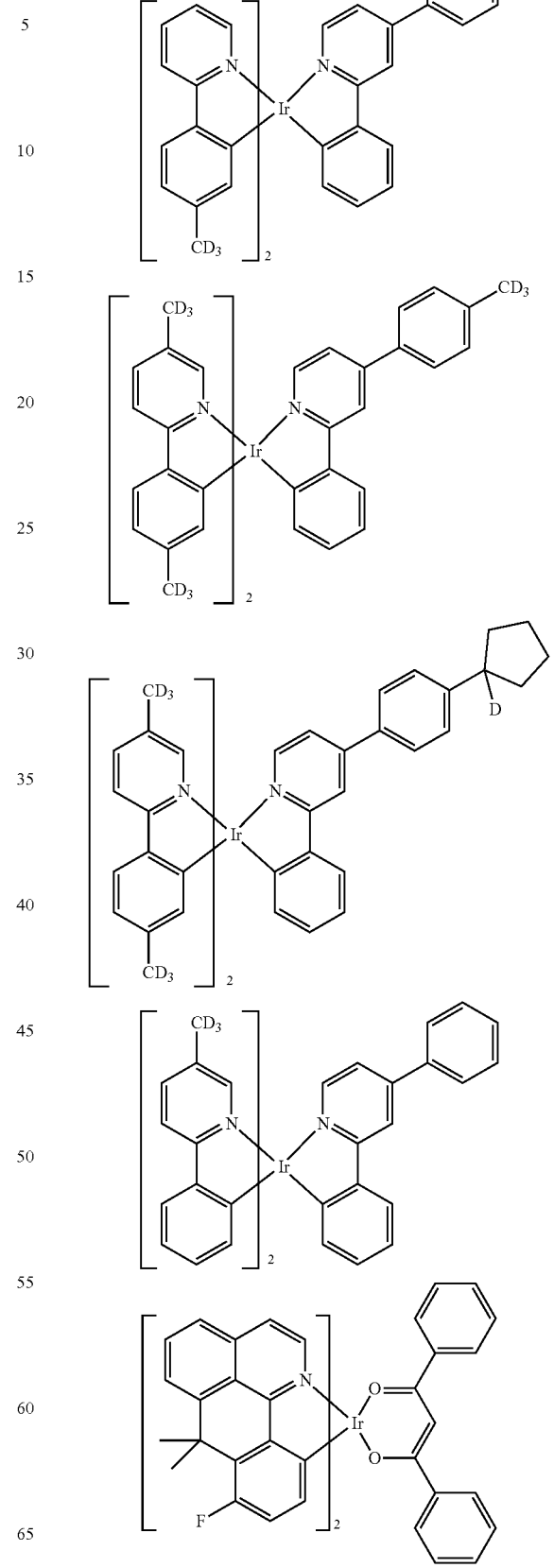

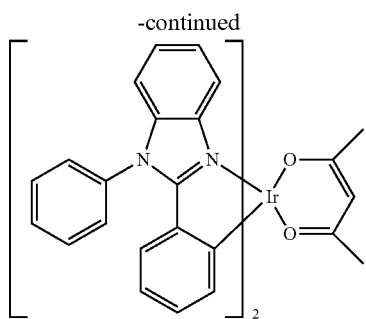
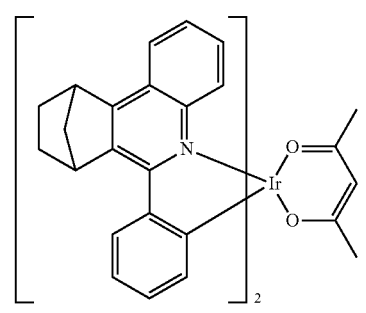
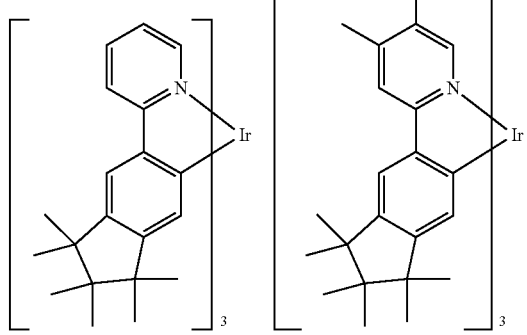
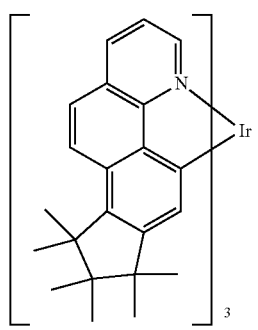
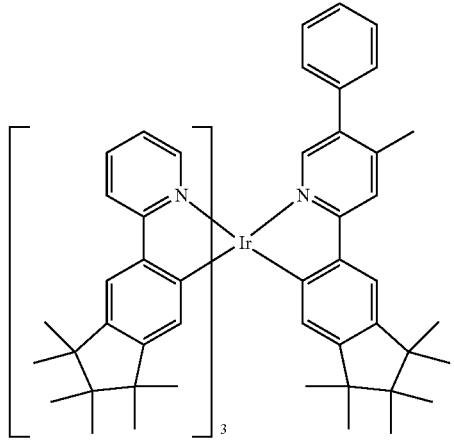
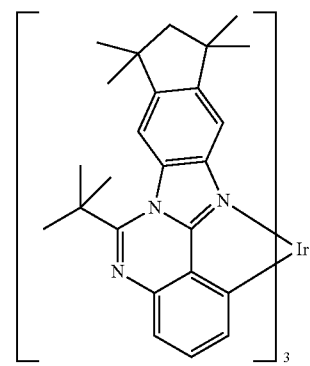
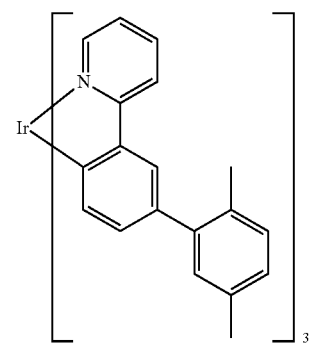

87
-continued
88
-continued
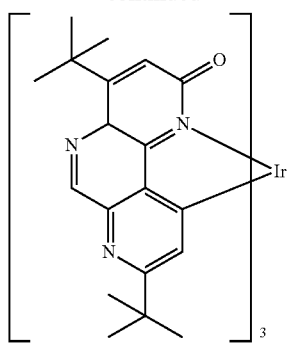
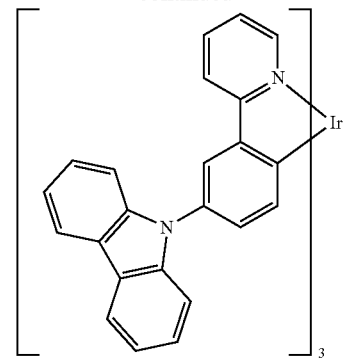
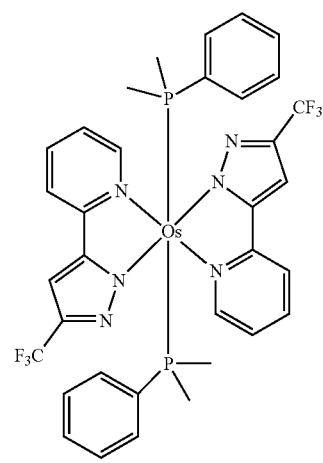
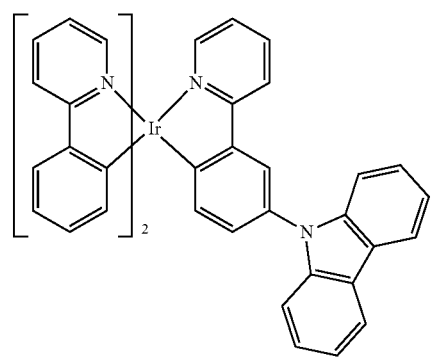
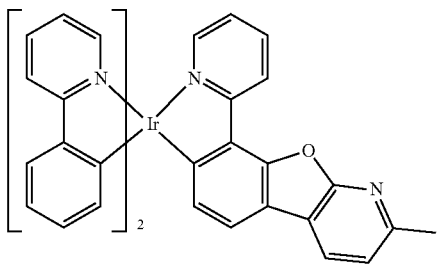
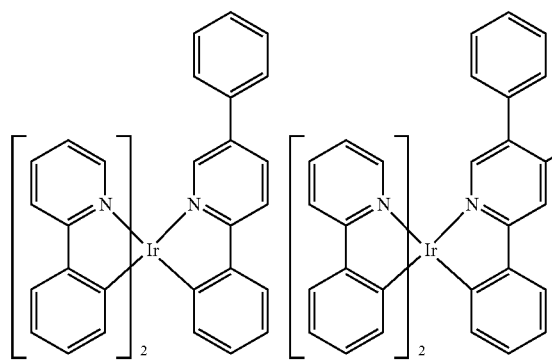
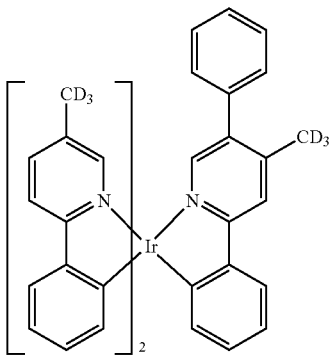
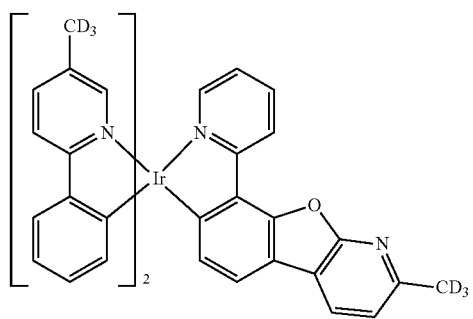

89
-continued
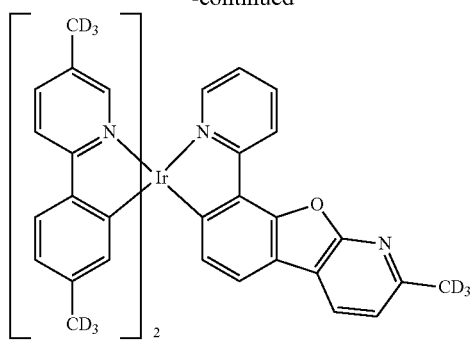
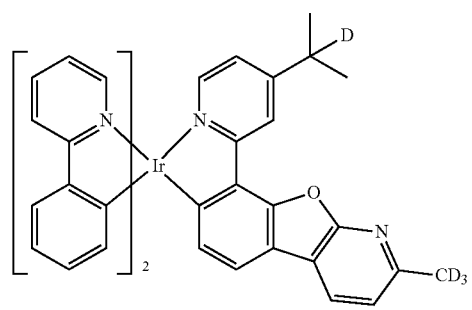
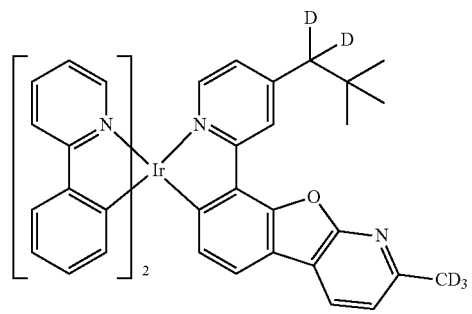
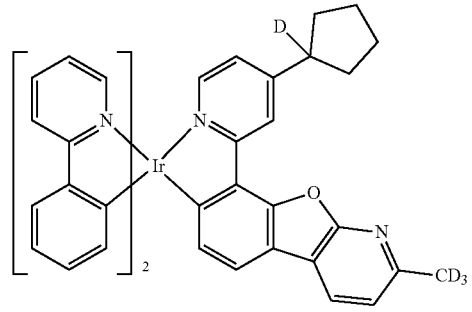
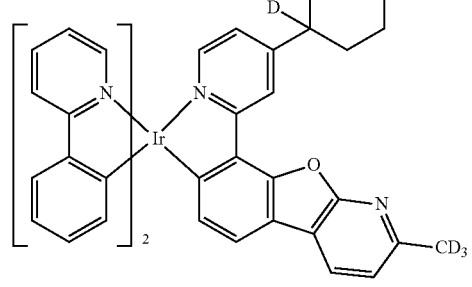
90
-continued
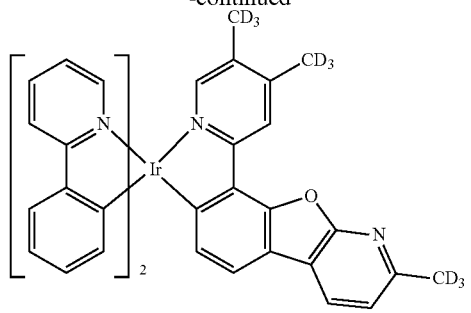
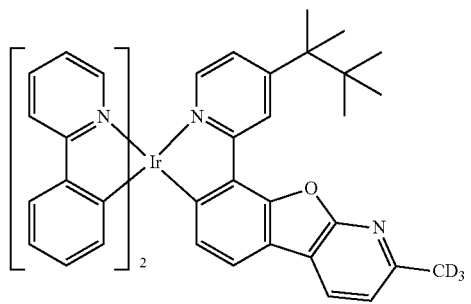
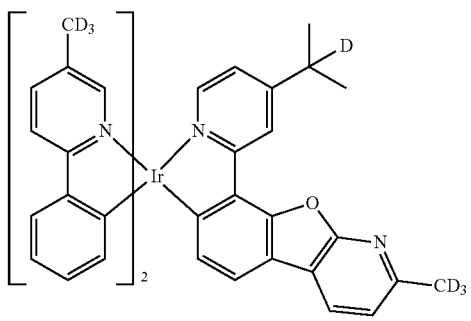
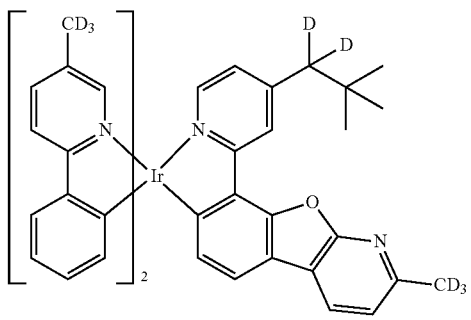
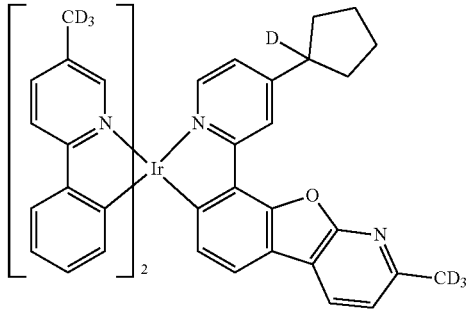

91
-continued
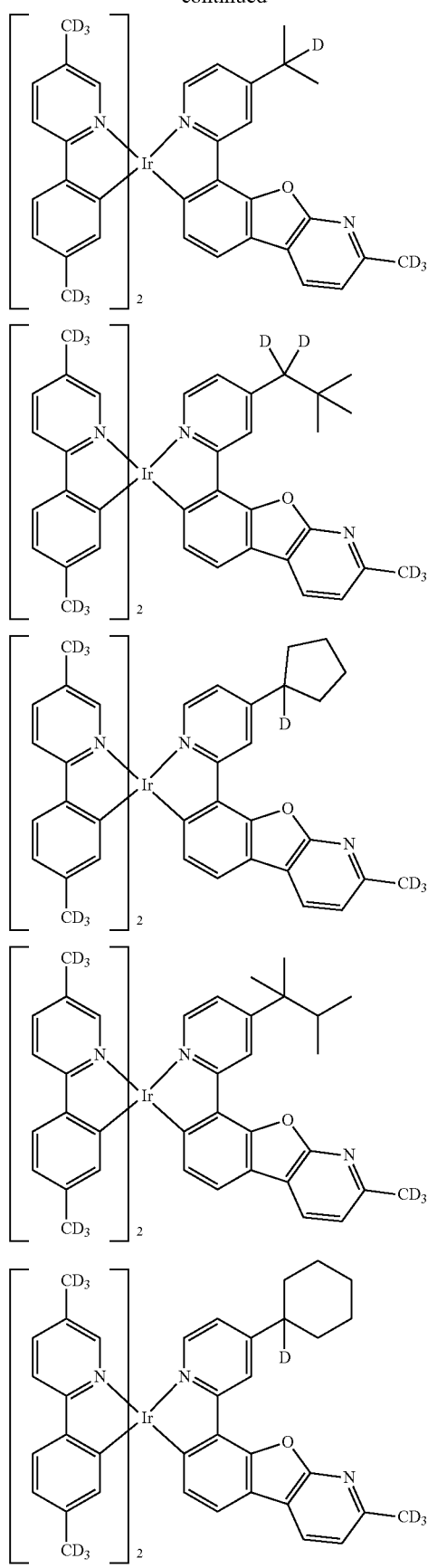
92
-continued
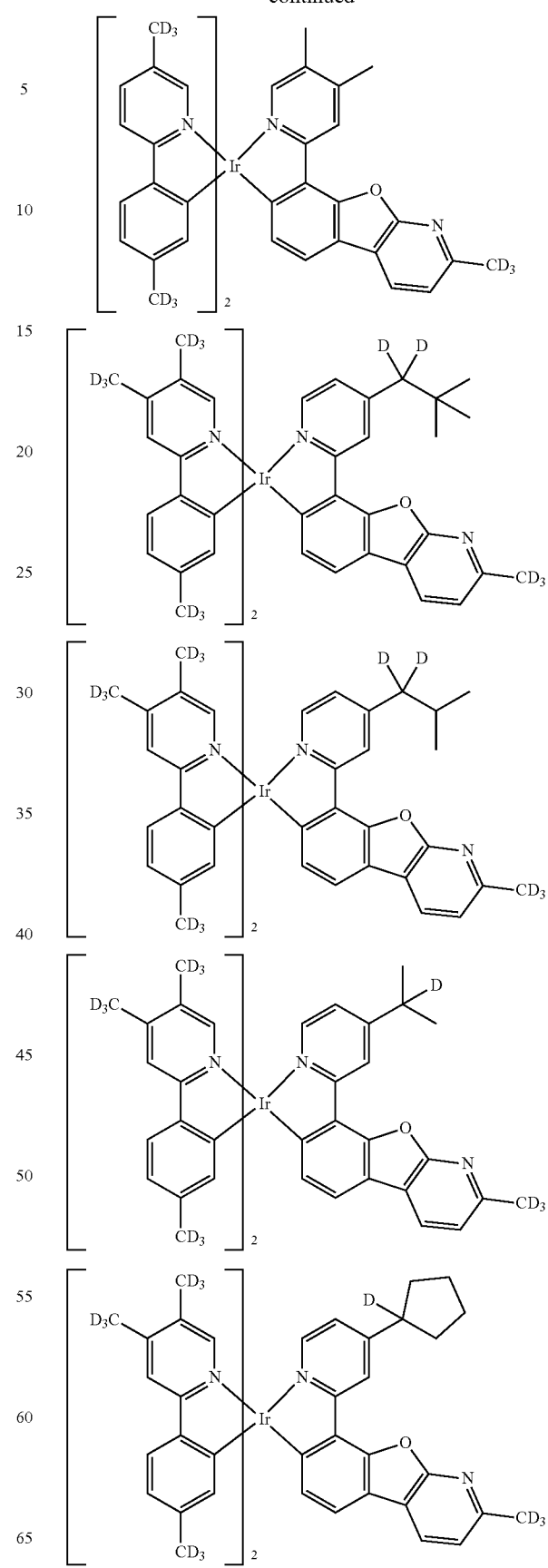

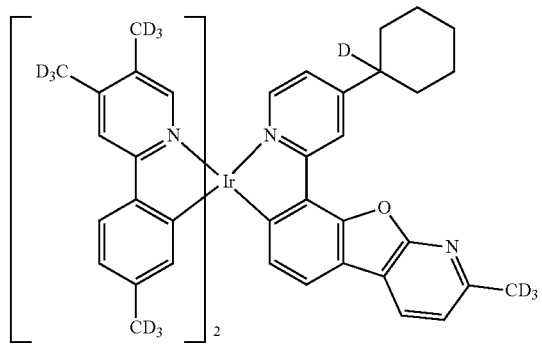
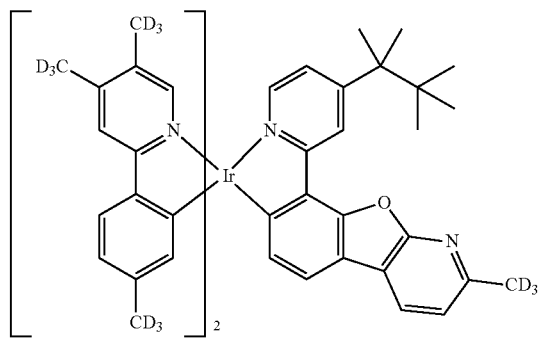
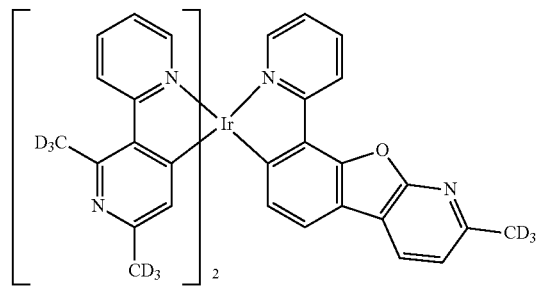
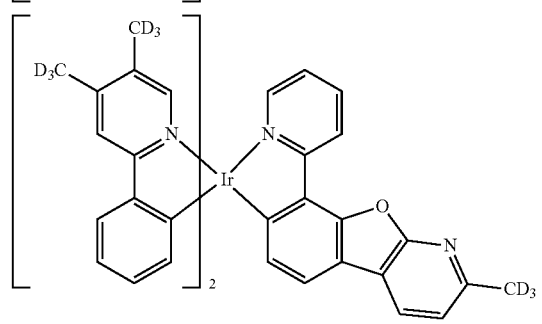
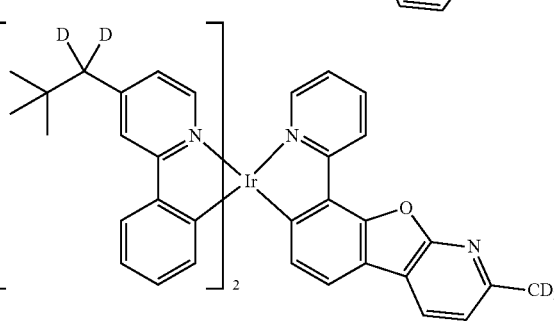
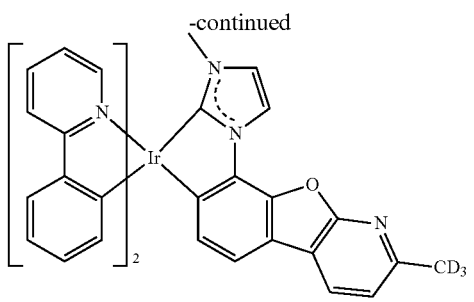
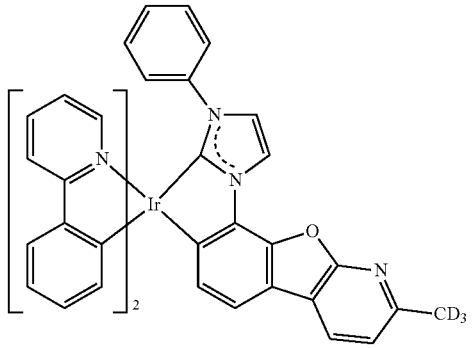
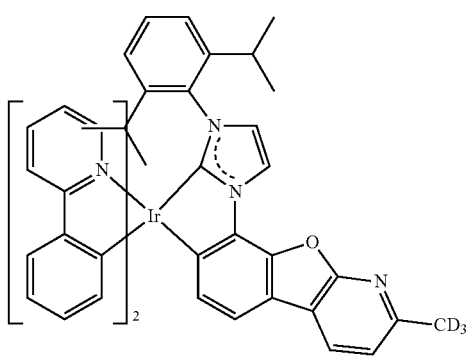
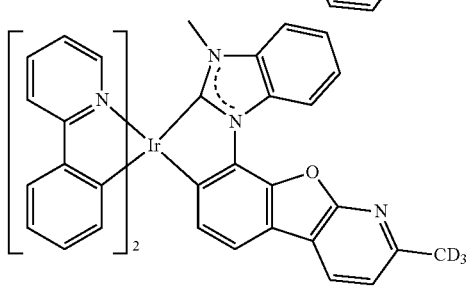
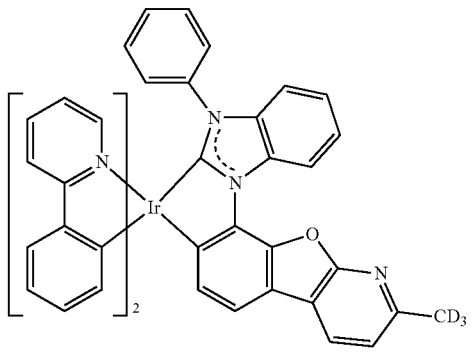

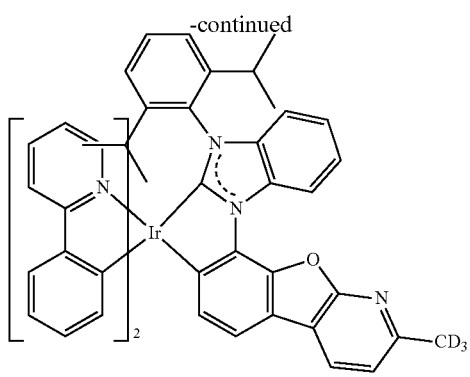
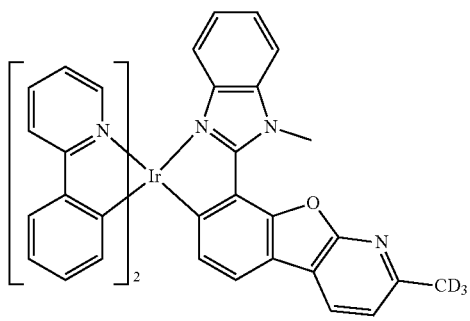
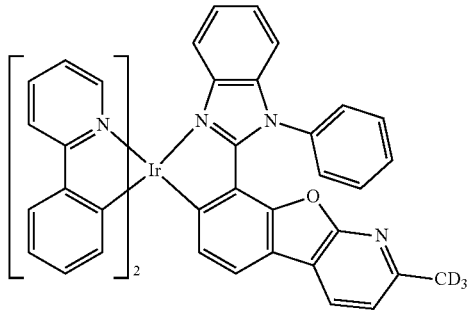
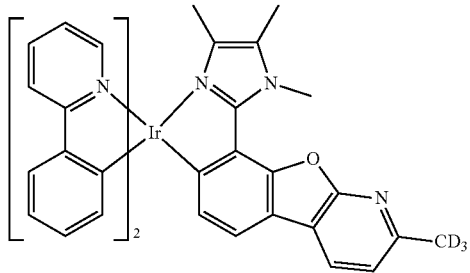
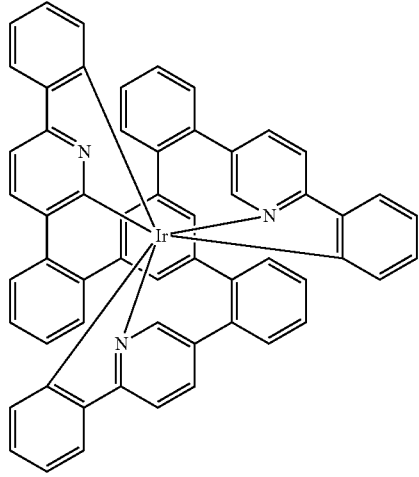
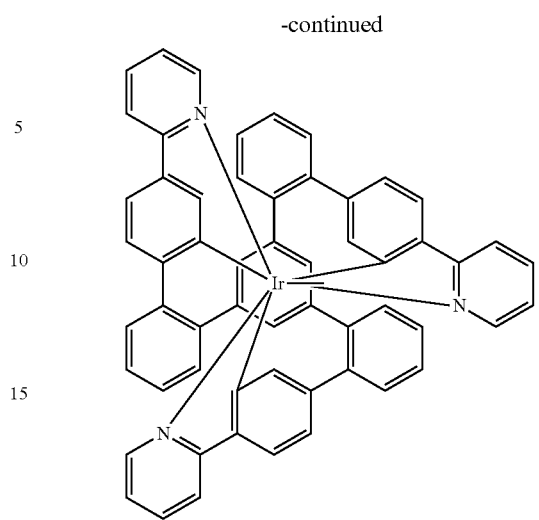
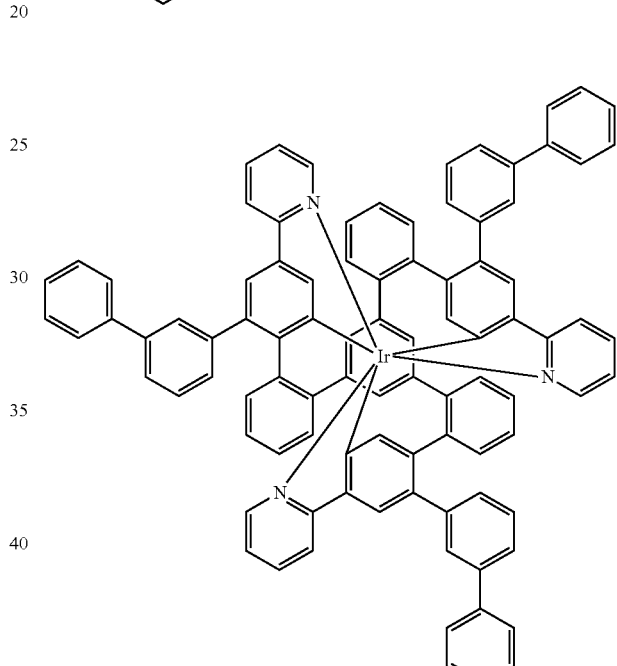
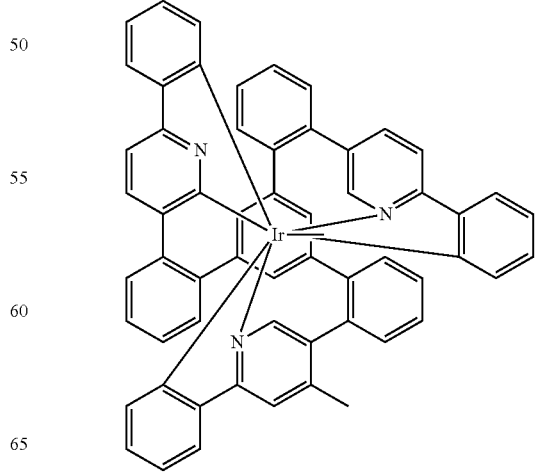

97
-continued
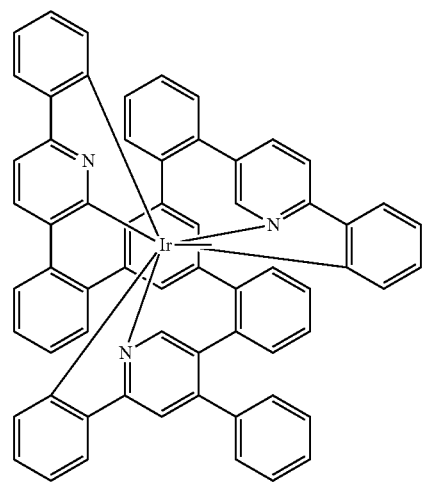
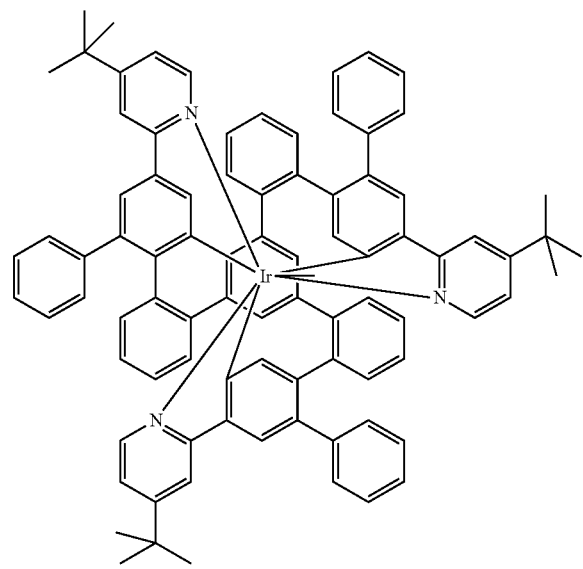
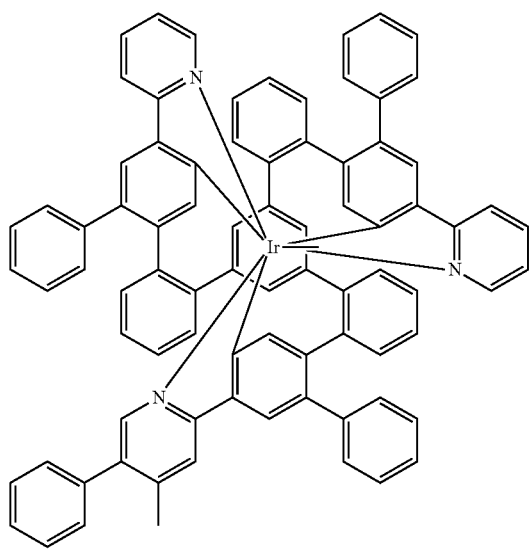
98
-continued
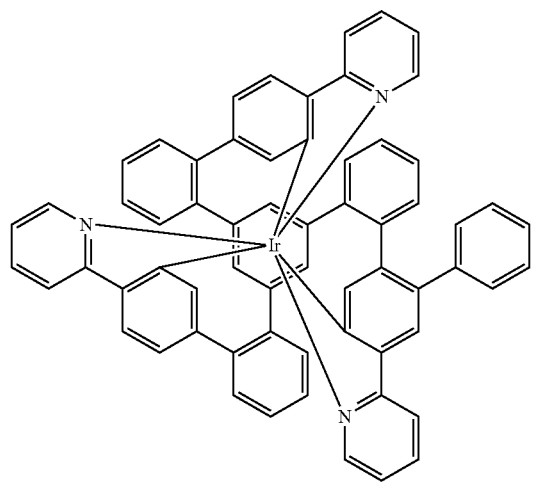
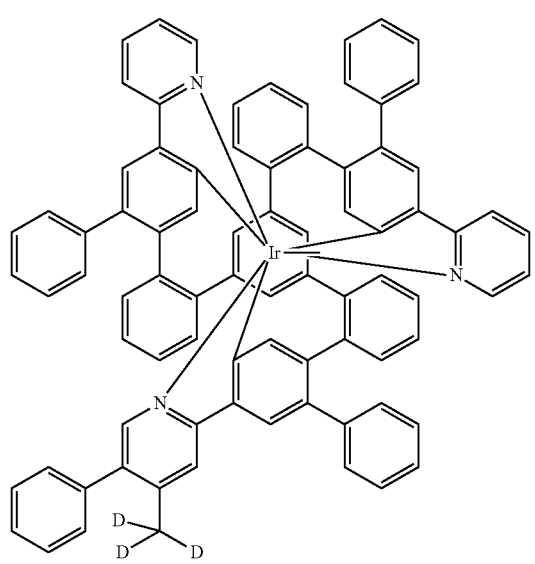
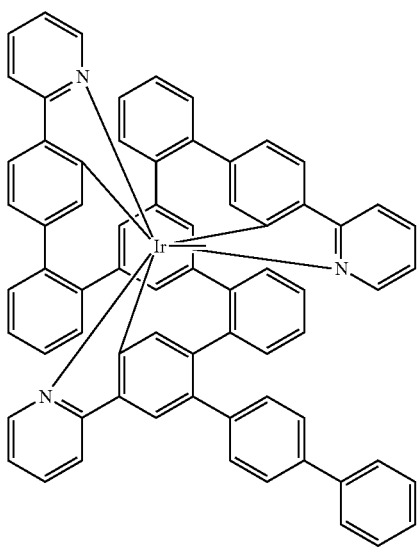

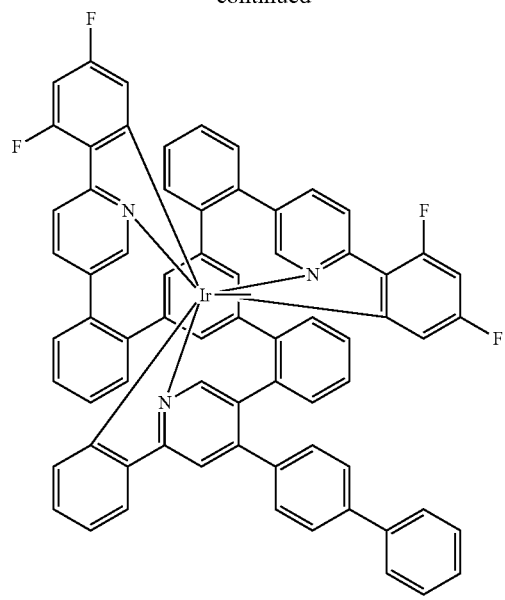
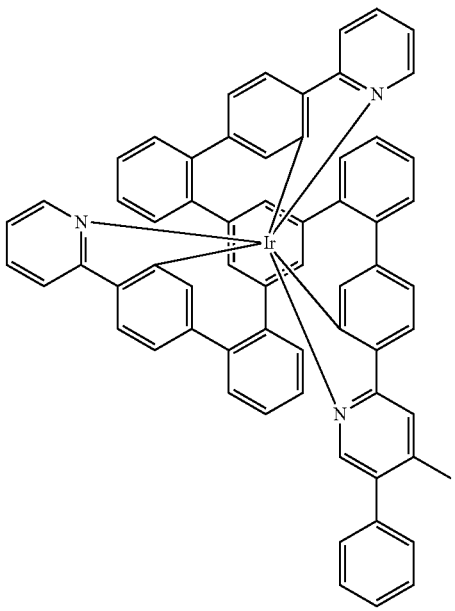
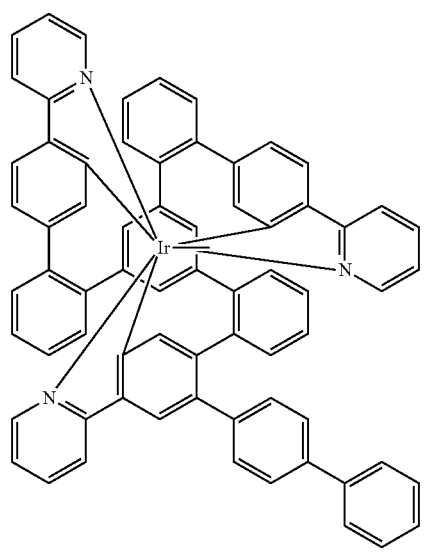
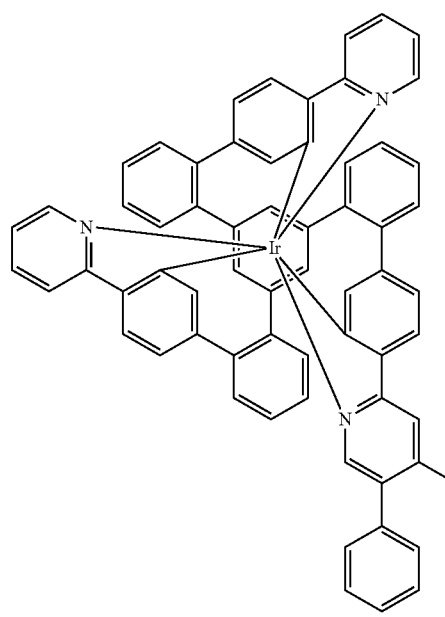
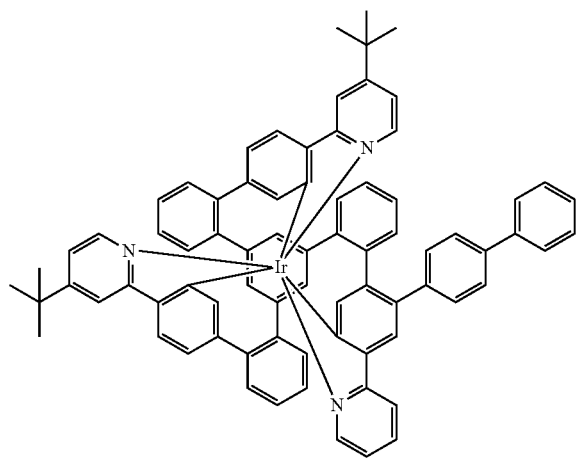
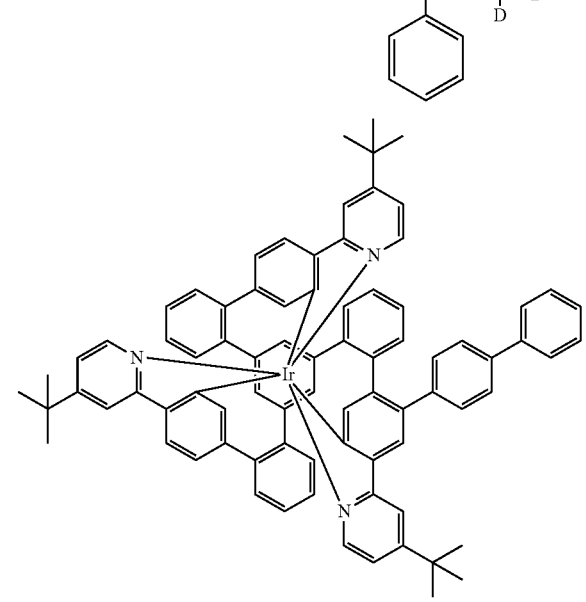

101
-continued
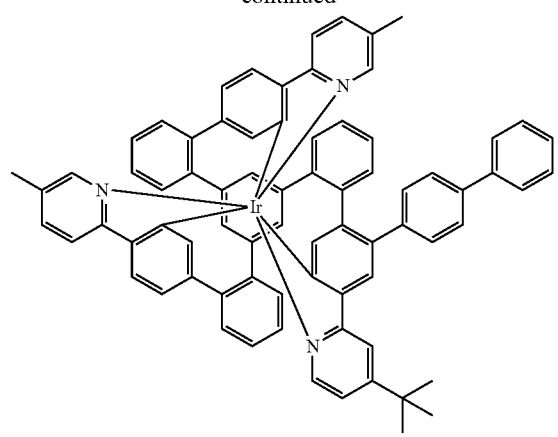
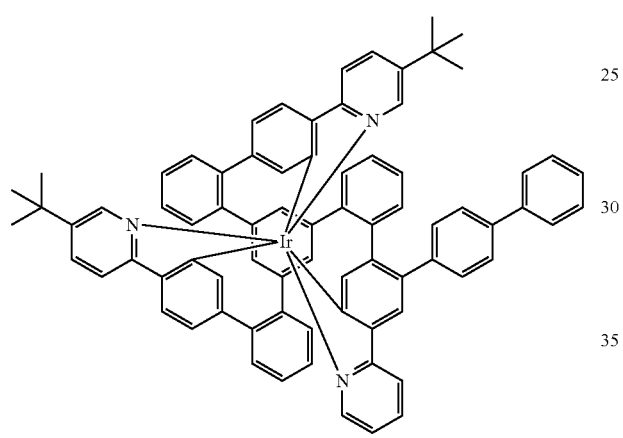
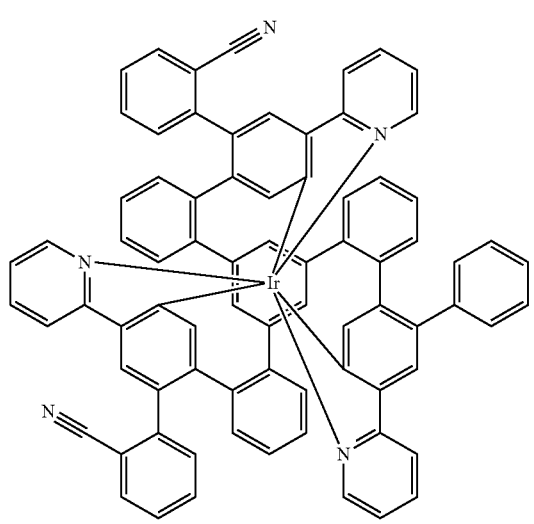
102
-continued
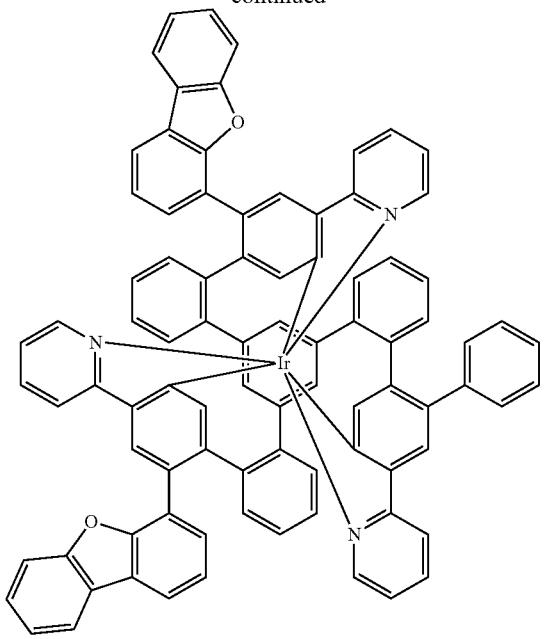
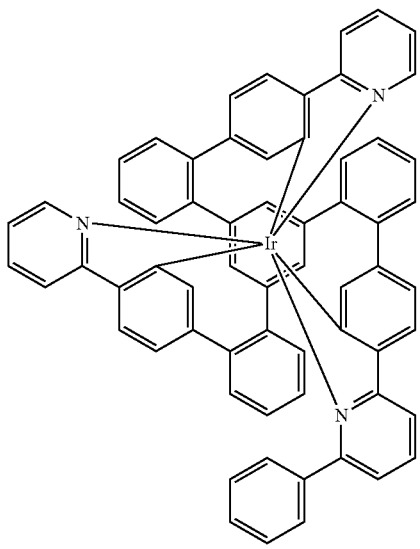
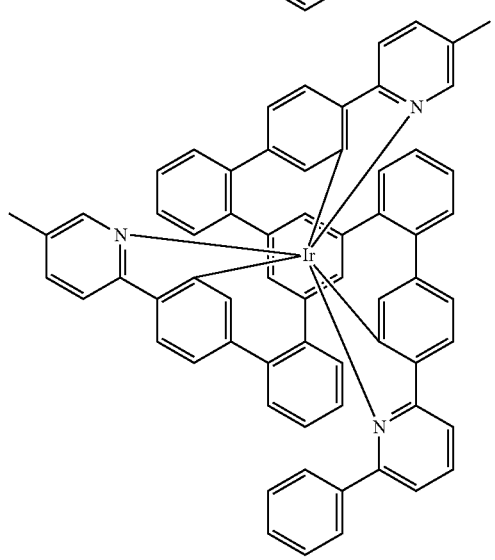

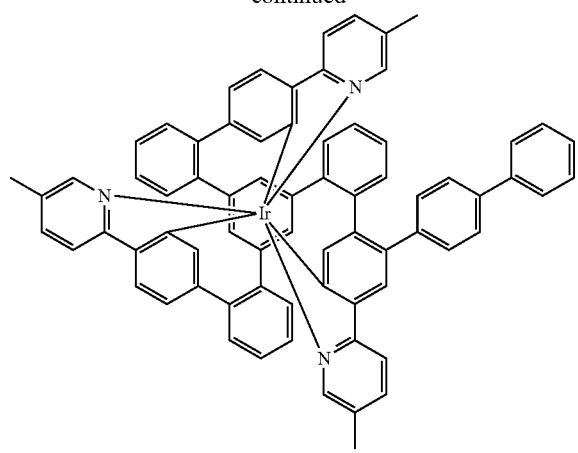
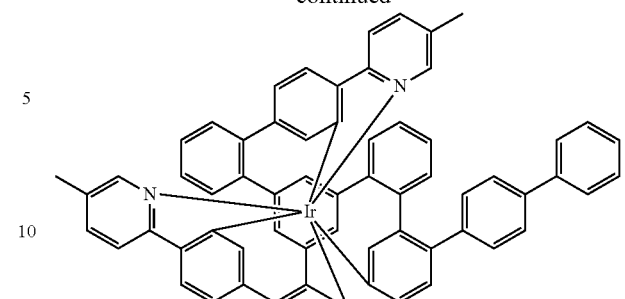
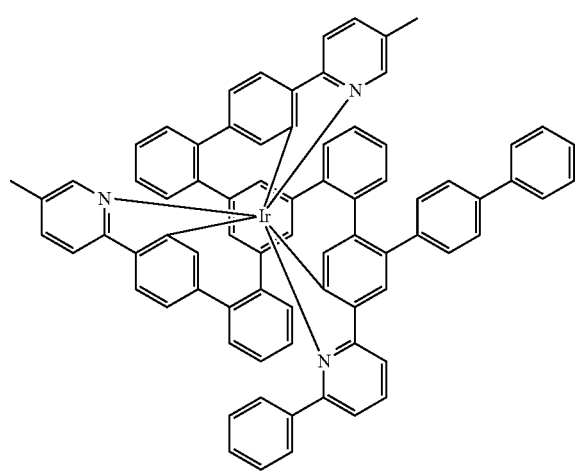
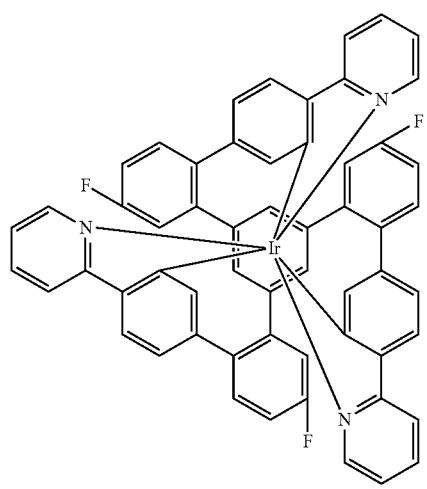
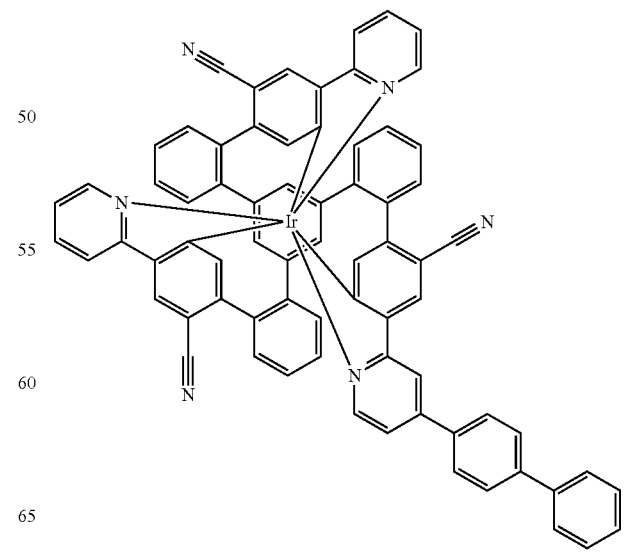

105
-continued
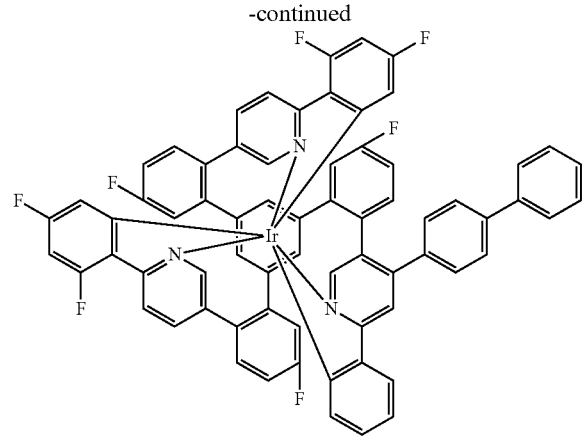
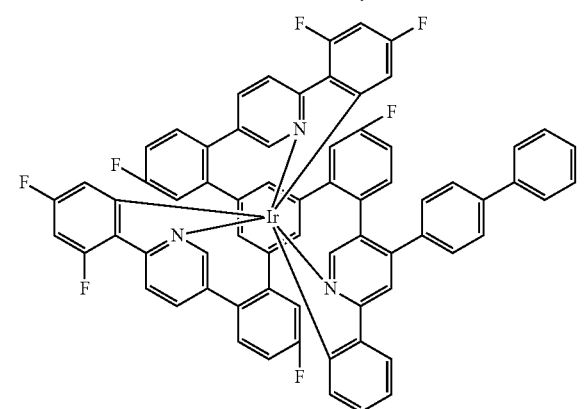
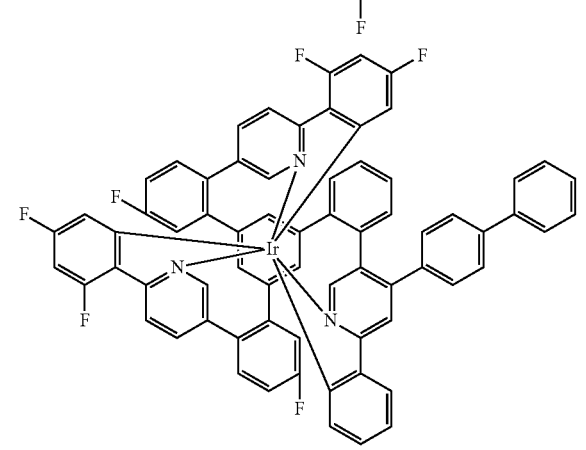
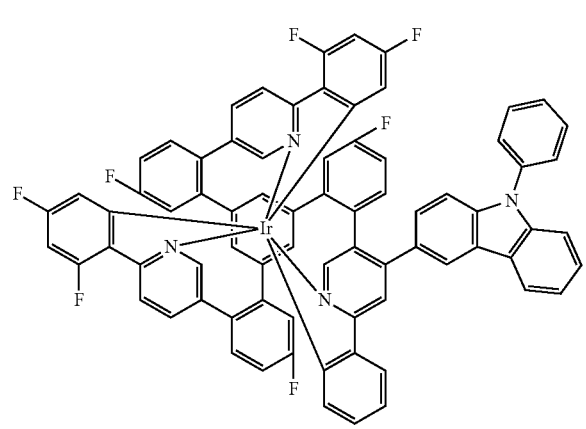
106
-continued
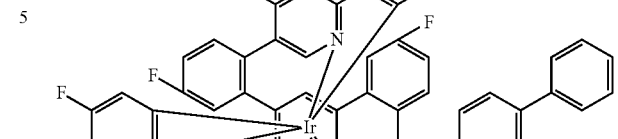
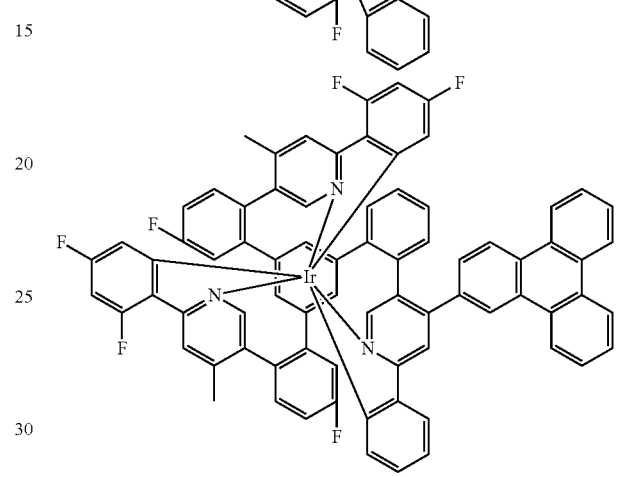
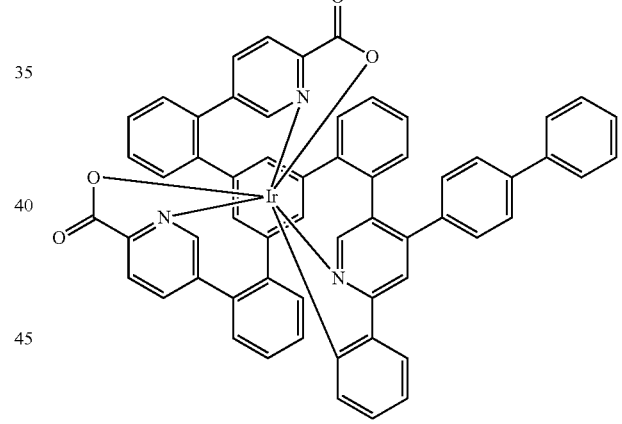
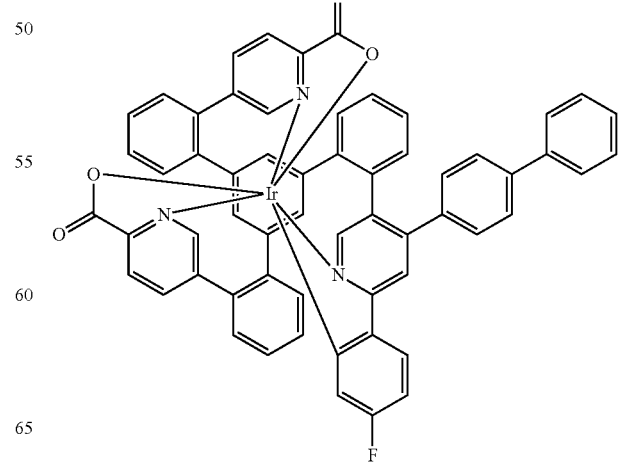

107
-continued
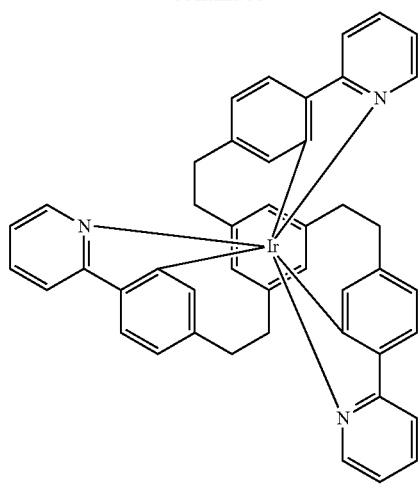
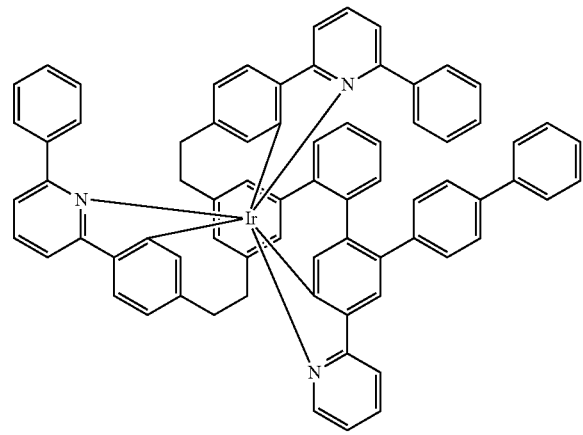
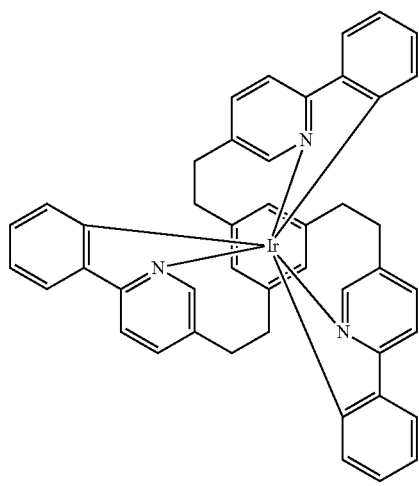
108
-continued
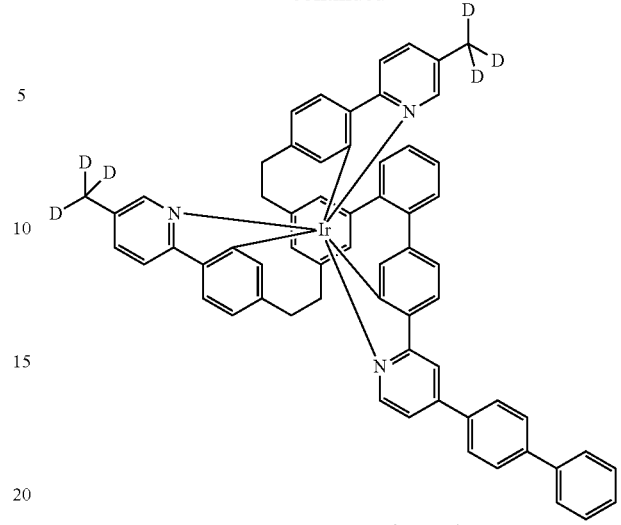
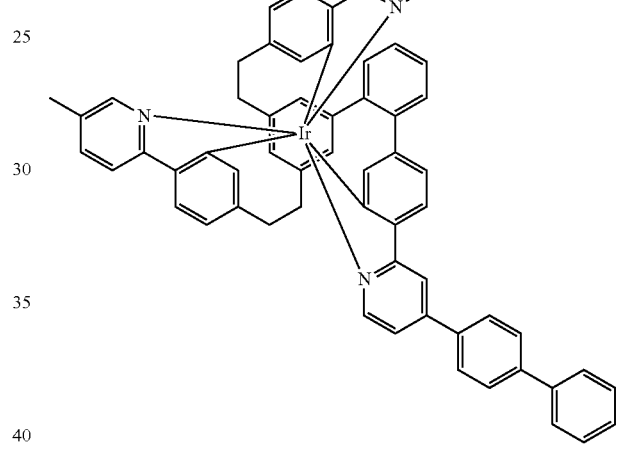
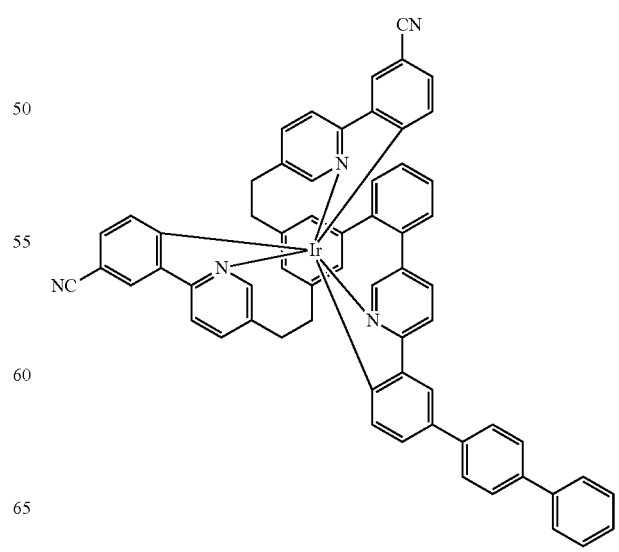

109
-continued
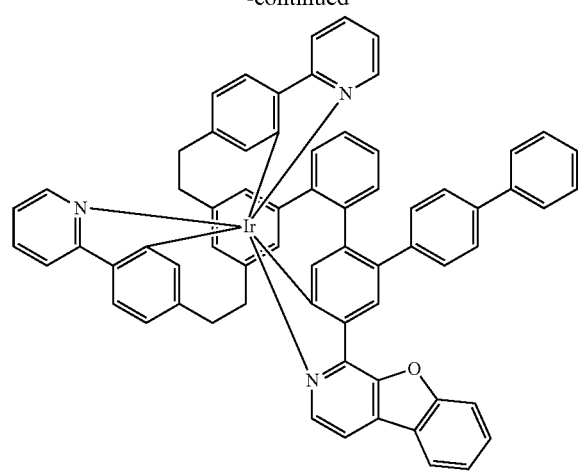
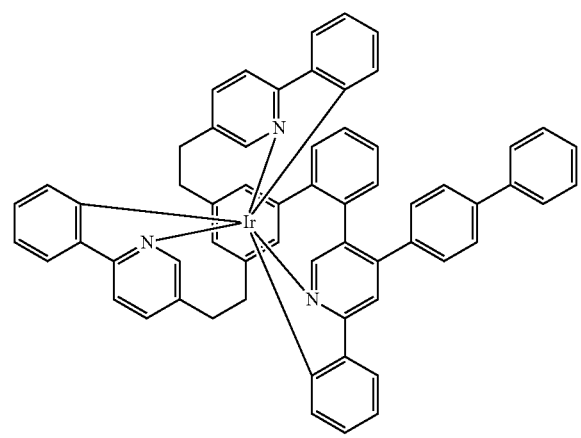
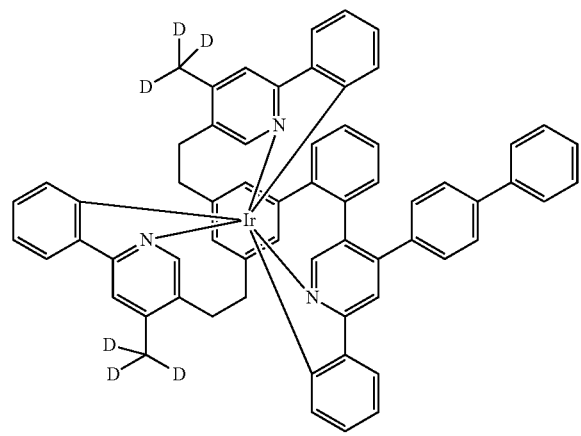
110
-continued
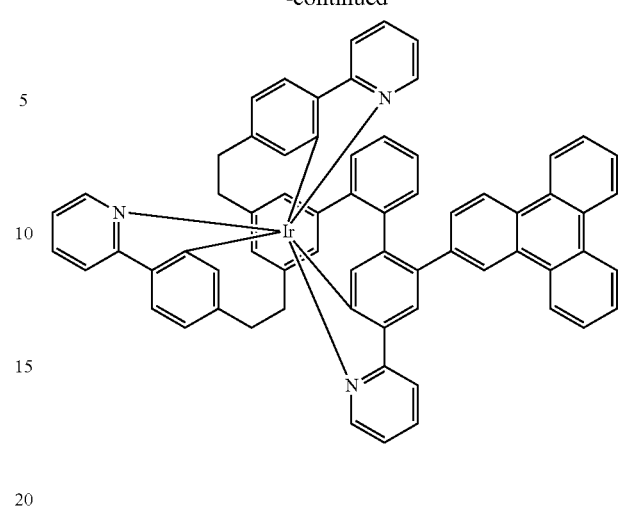
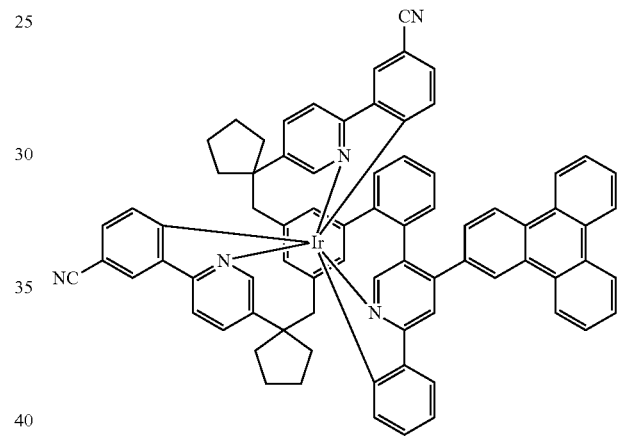
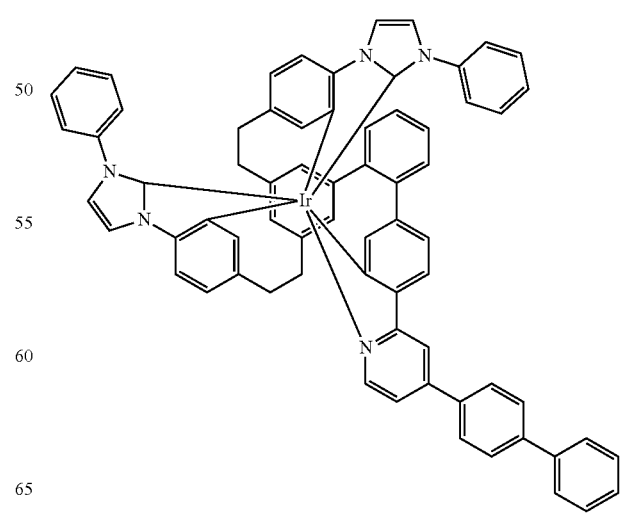

111
-continued
112
-continued
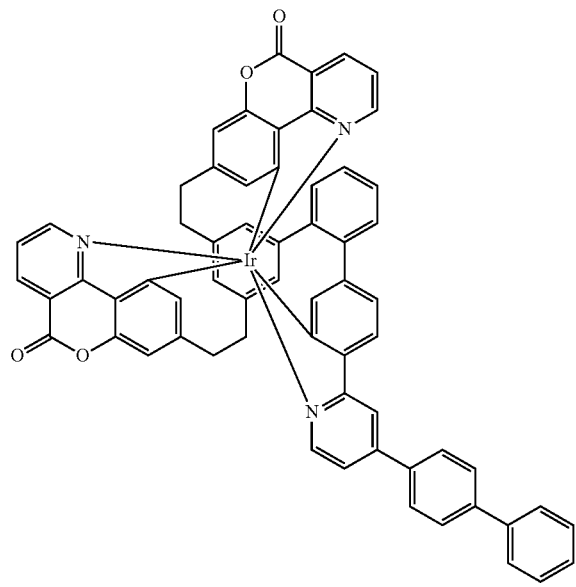
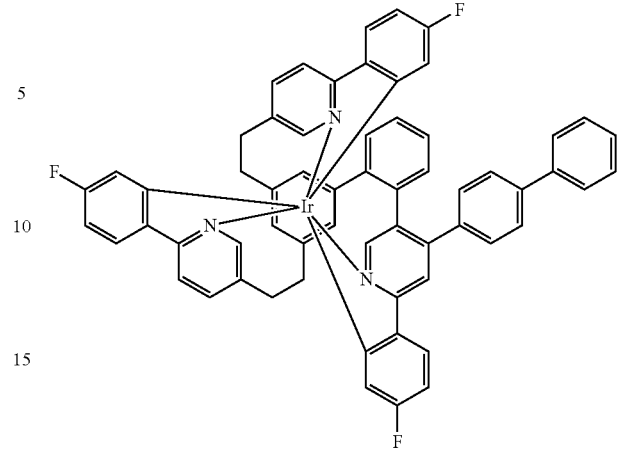
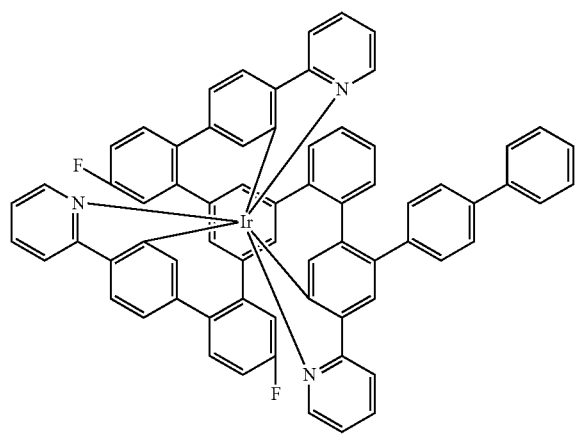
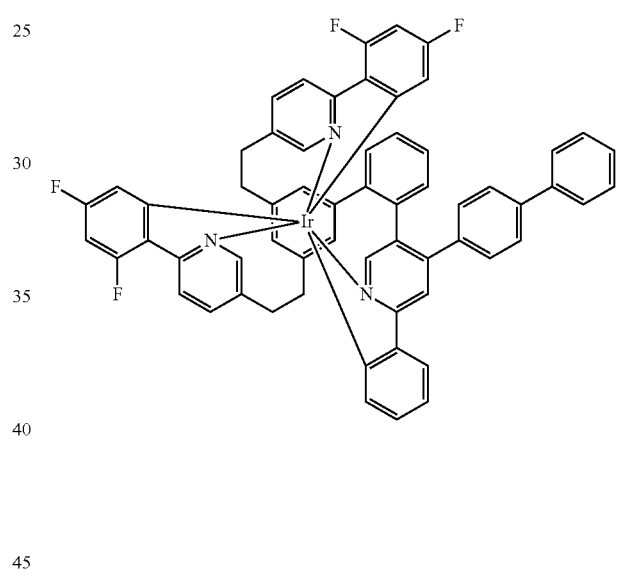
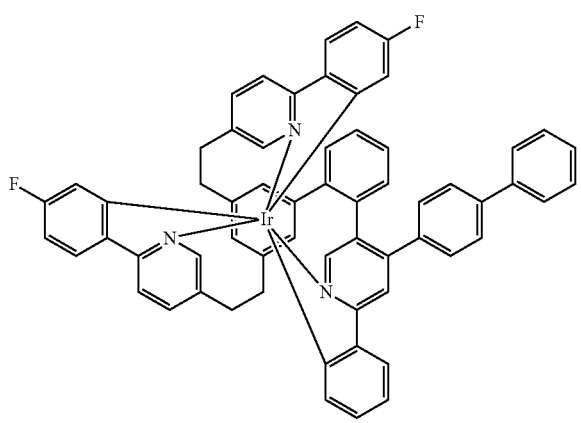
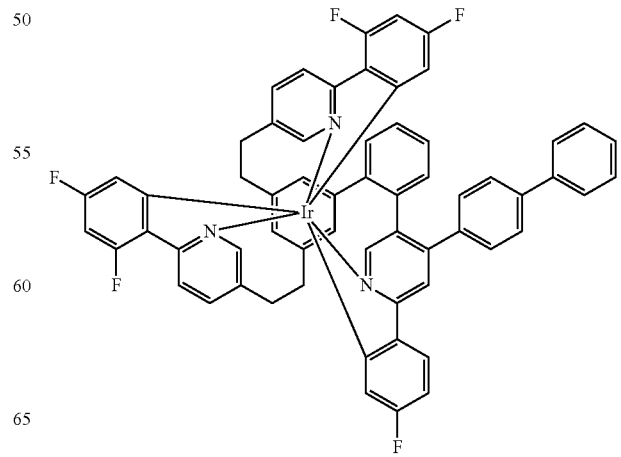

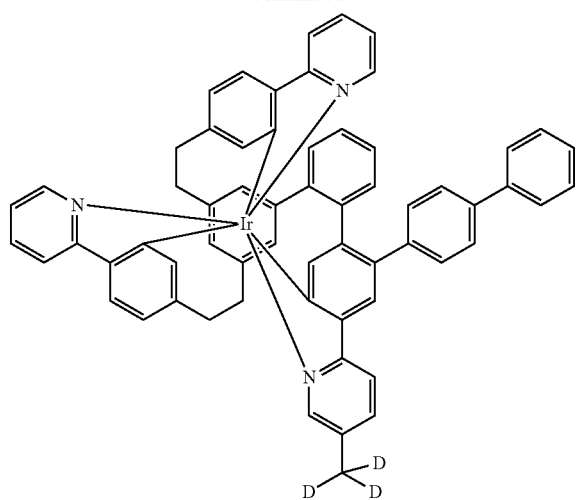
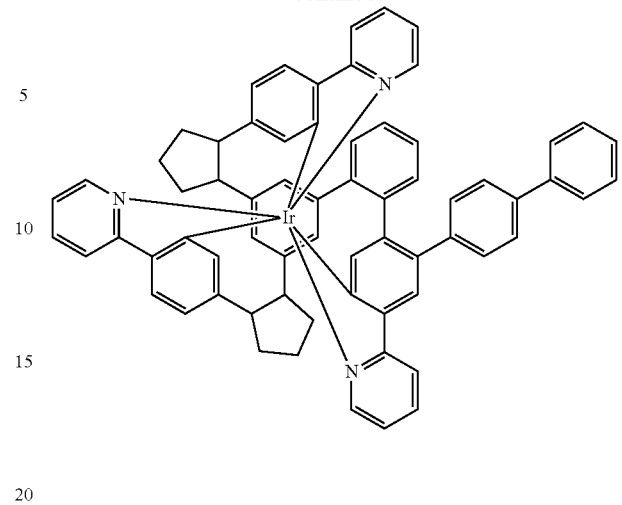
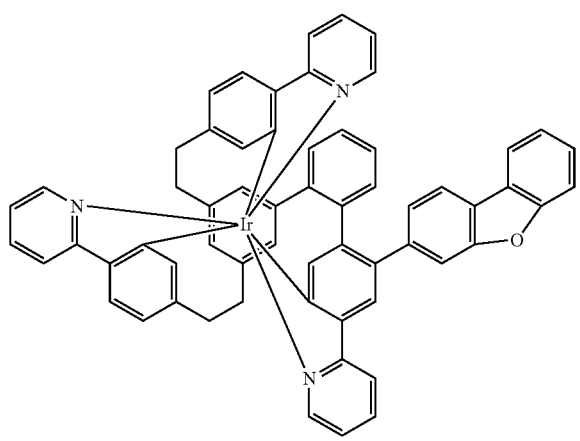
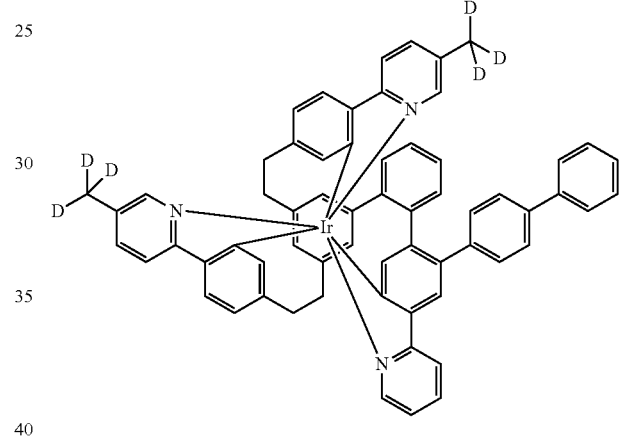
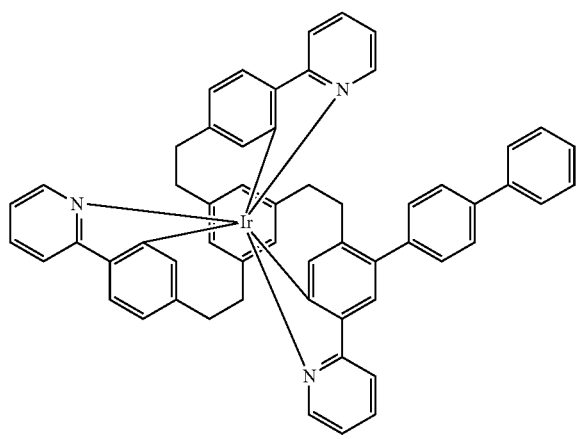
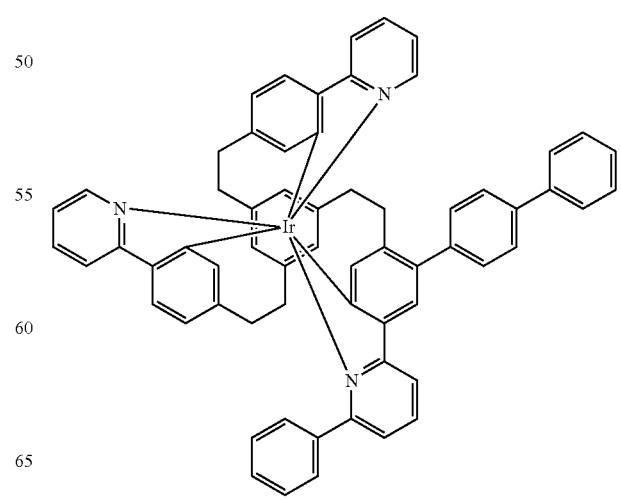

115
-continued
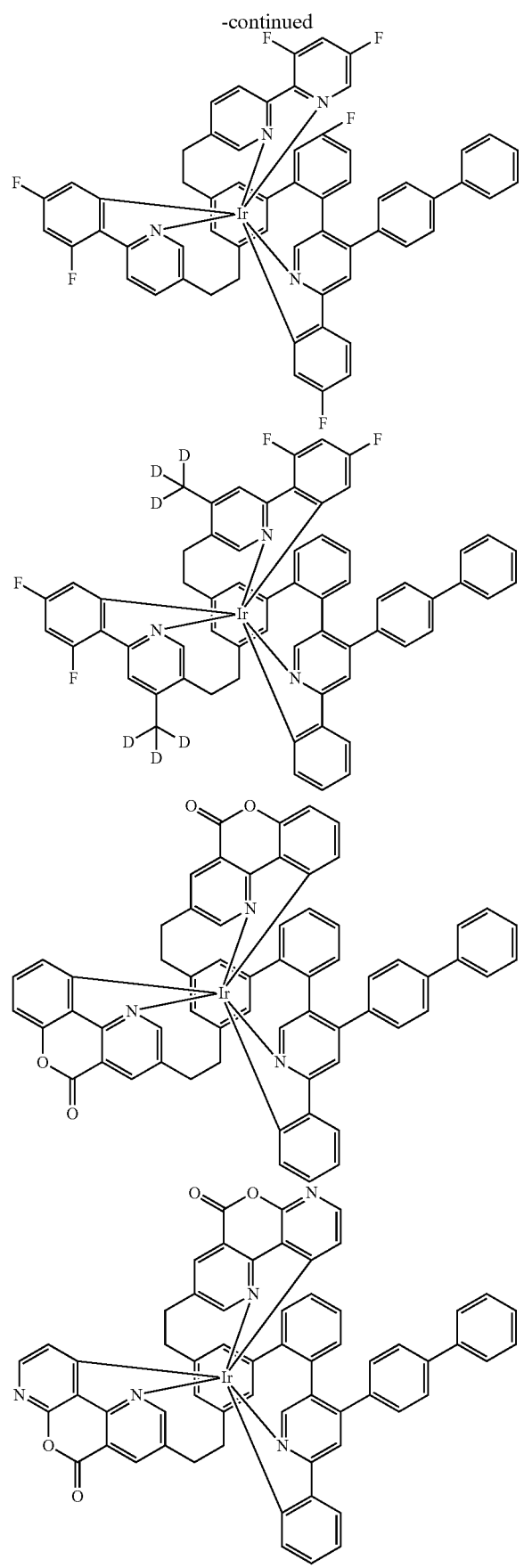
116
-continued
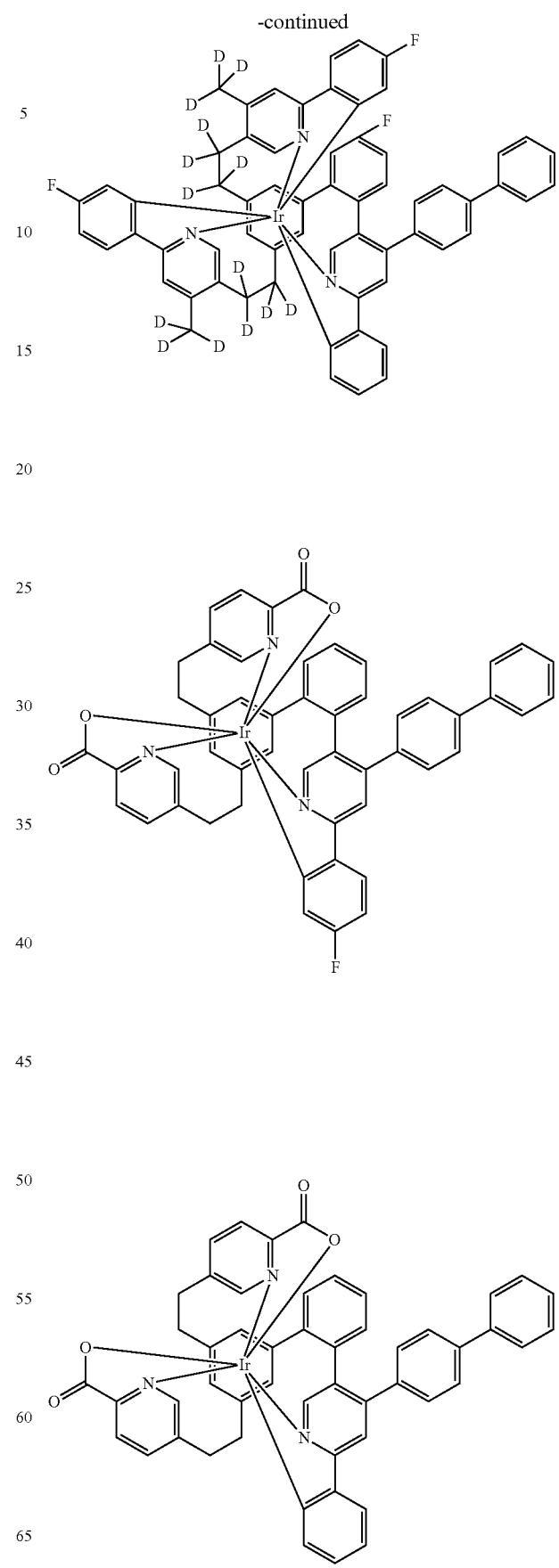

117
-continued
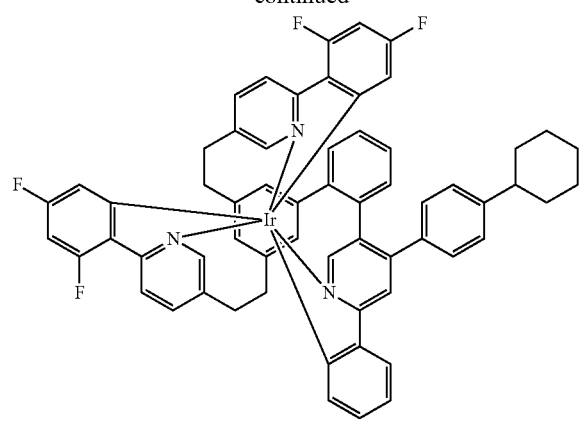
118
-continued
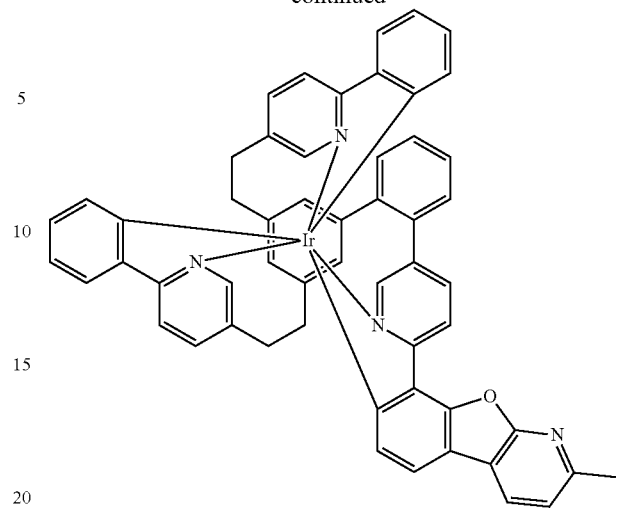
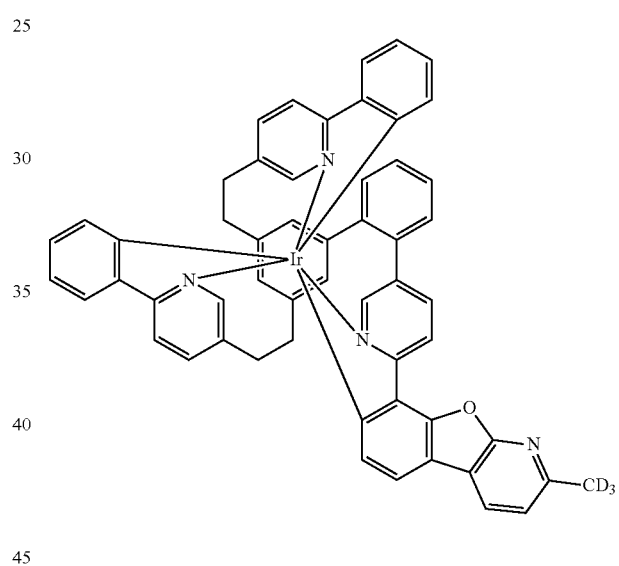
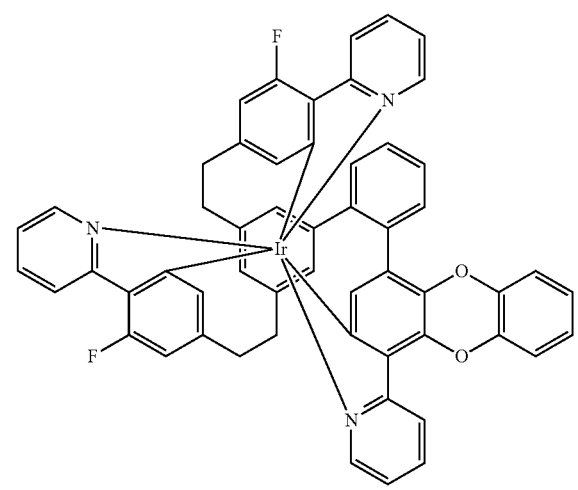
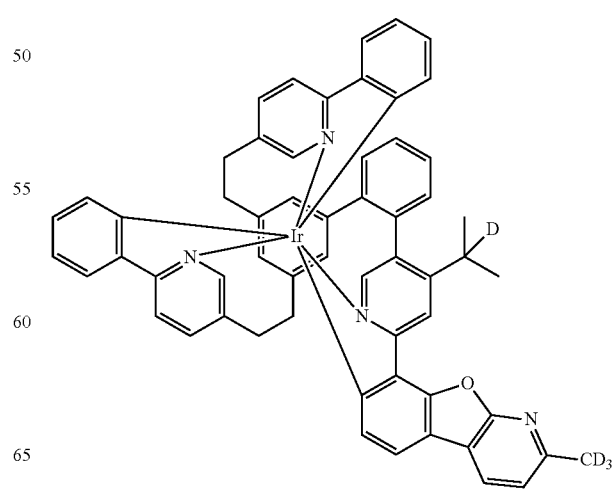

119
-continued
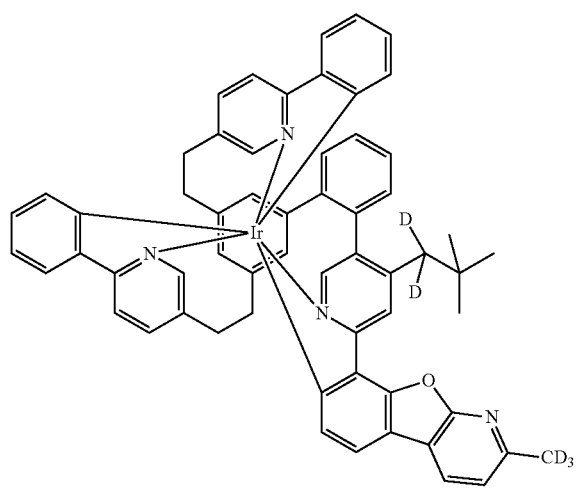
120
-continued
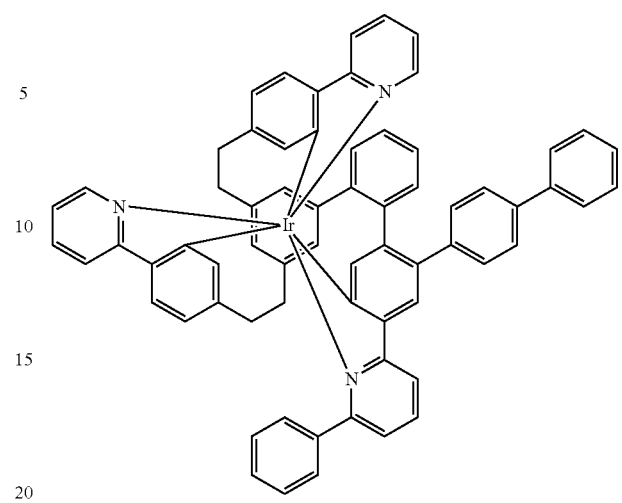
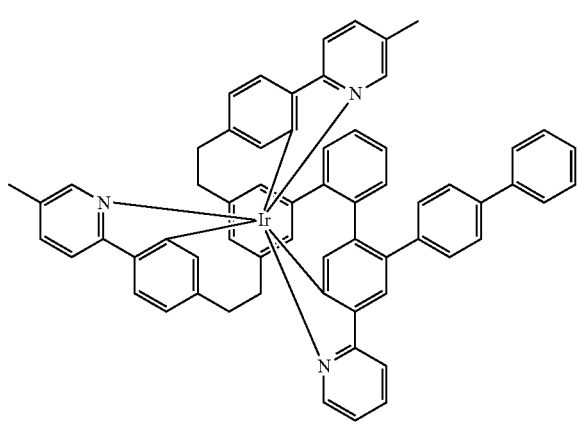
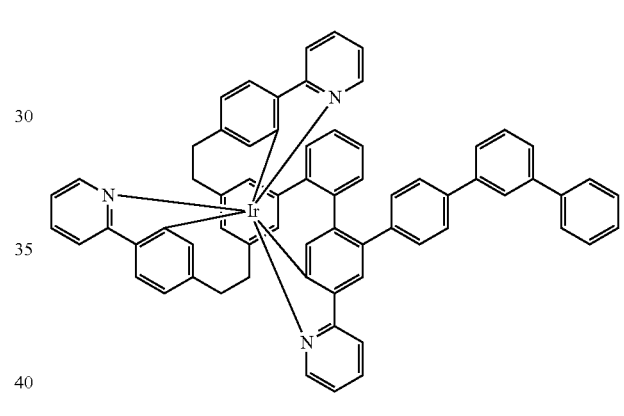
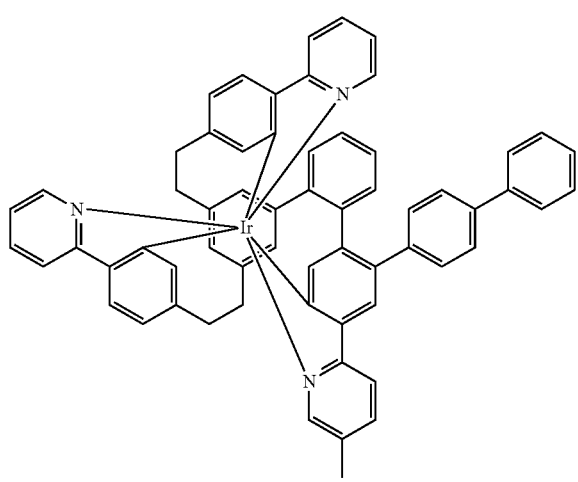
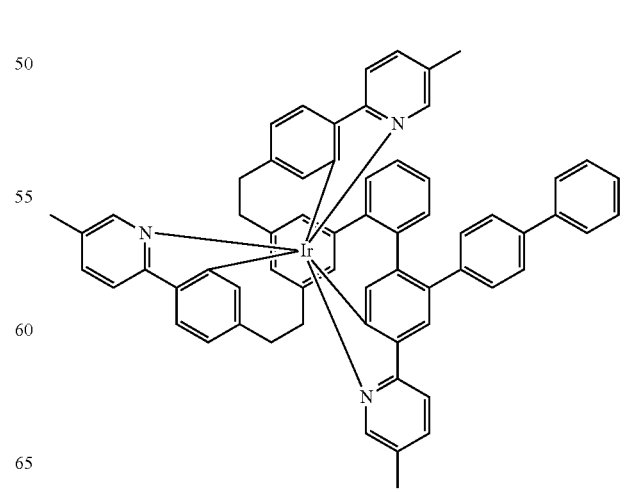

121
-continued
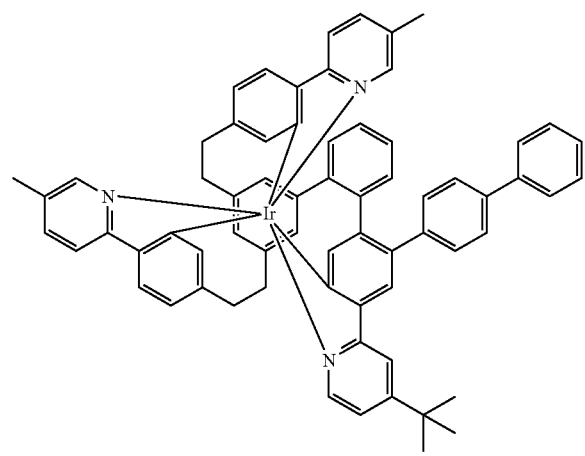
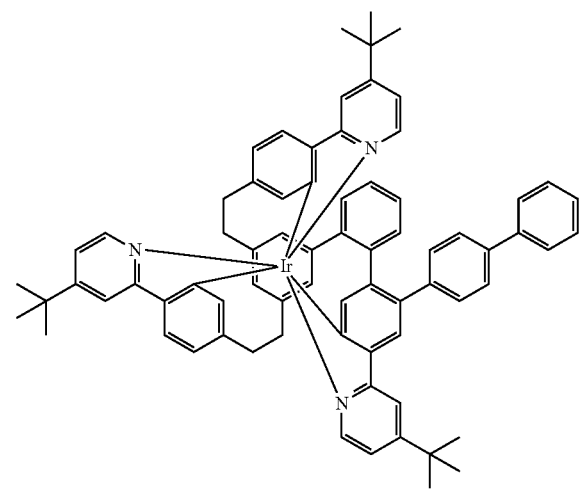
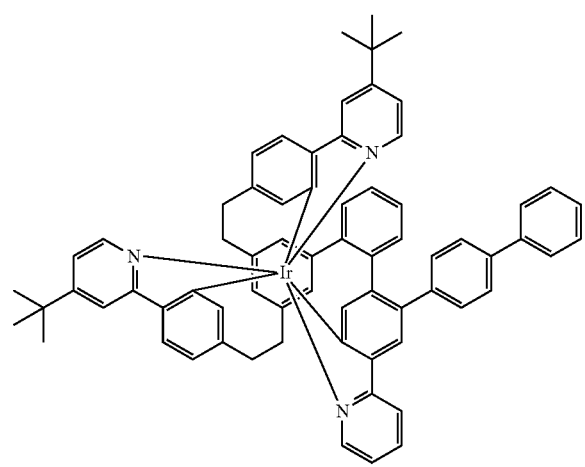
122
-continued
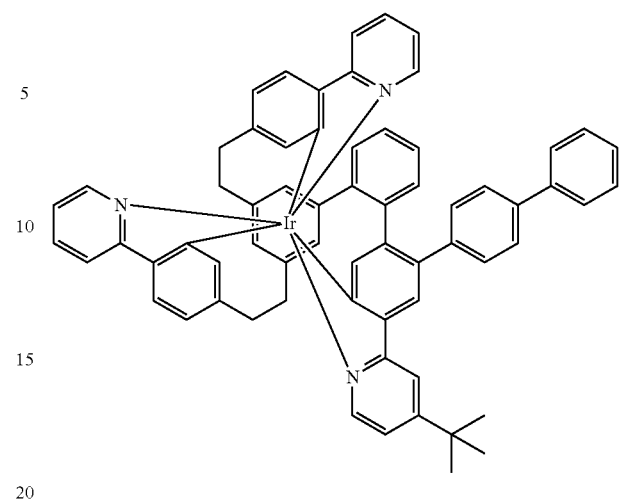
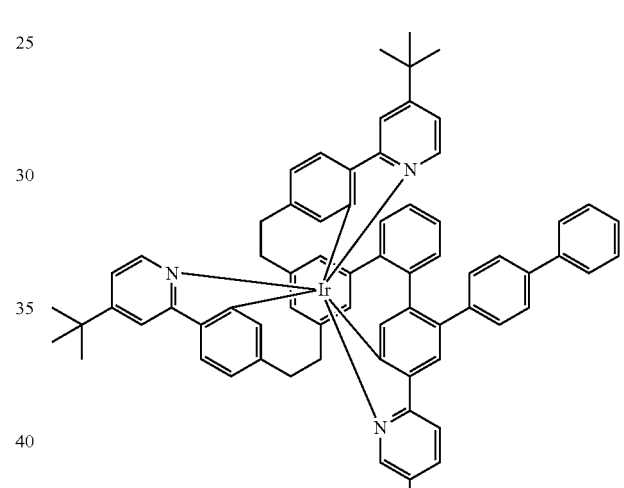
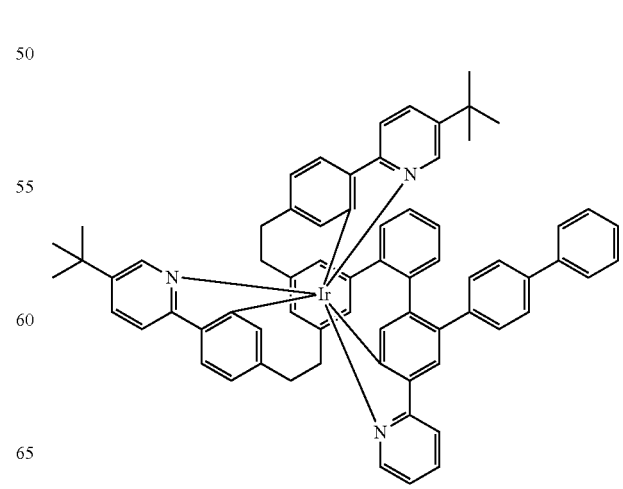

| 123 -continued | 124 -continued |
|---|---|
| 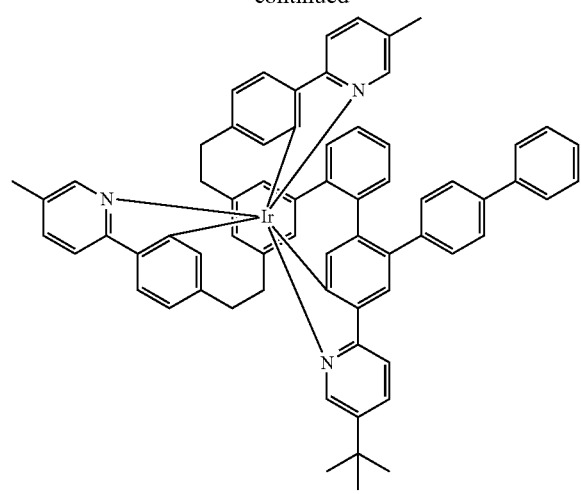 | 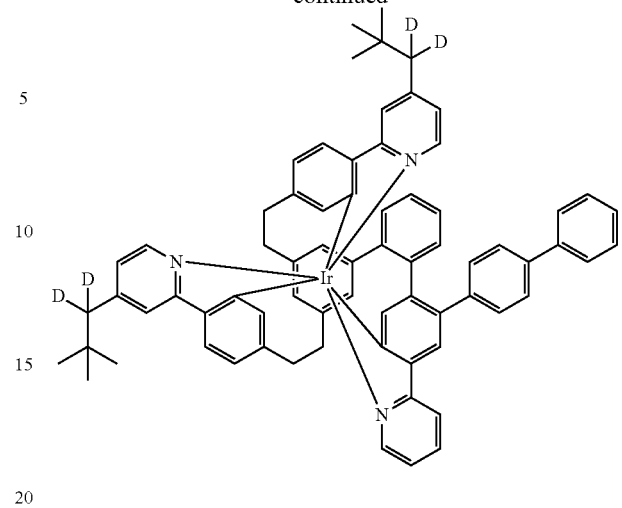 |
| 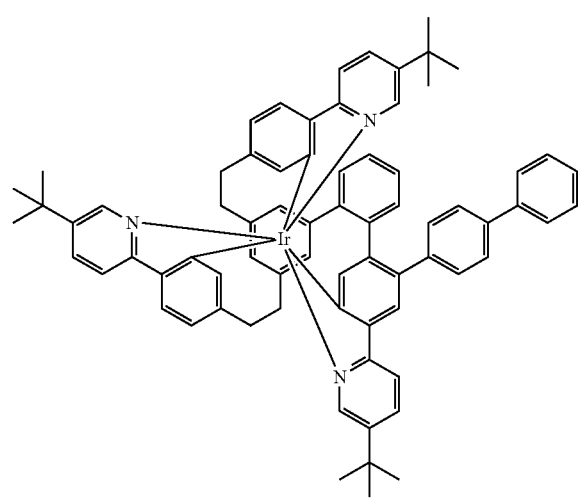 | 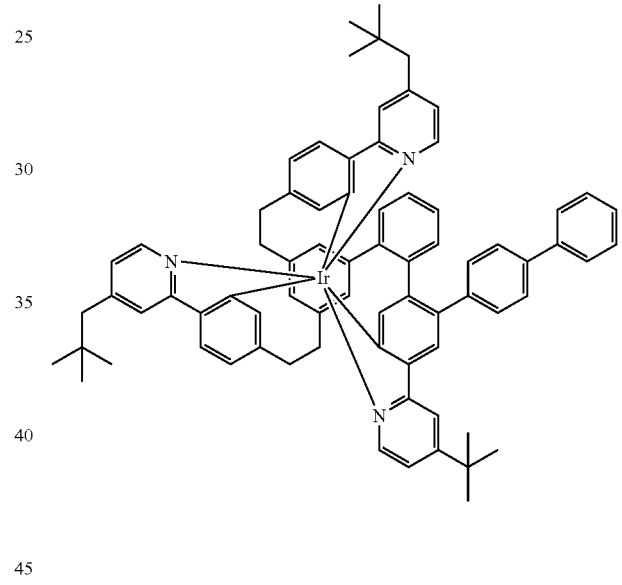 |
| 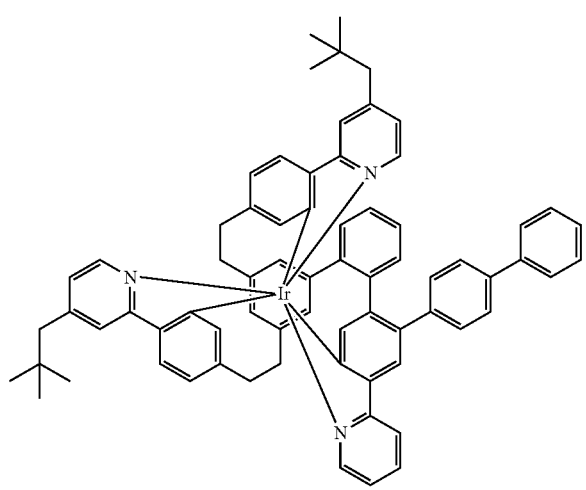 | 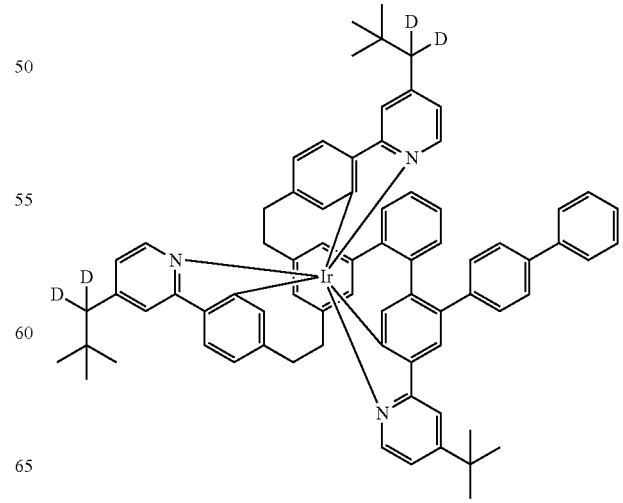 |

125
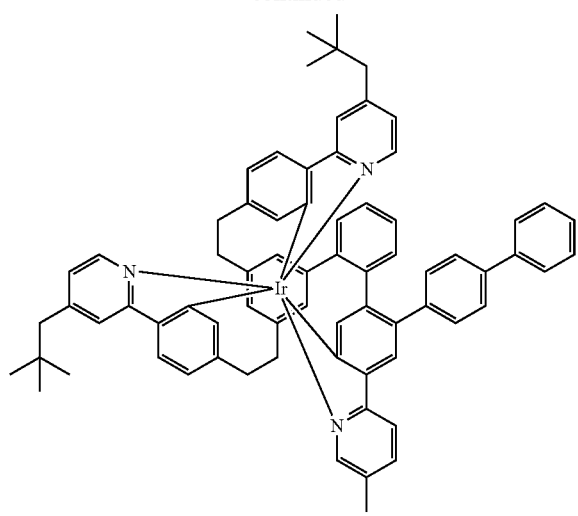
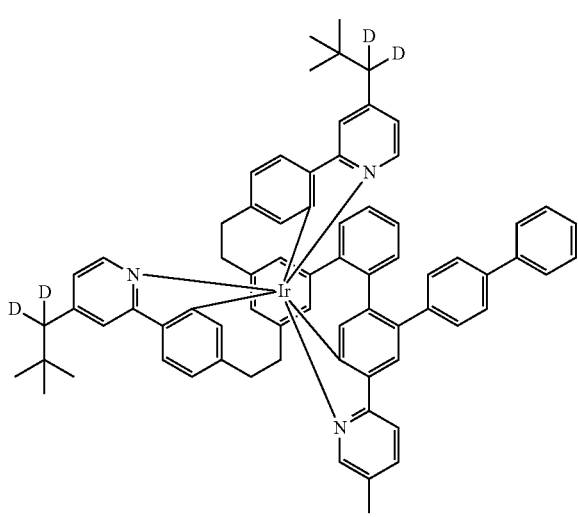
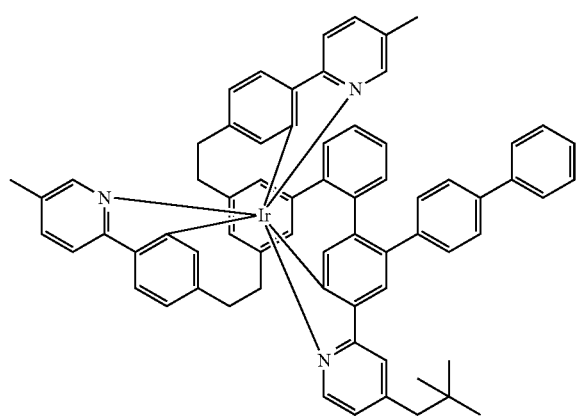
126
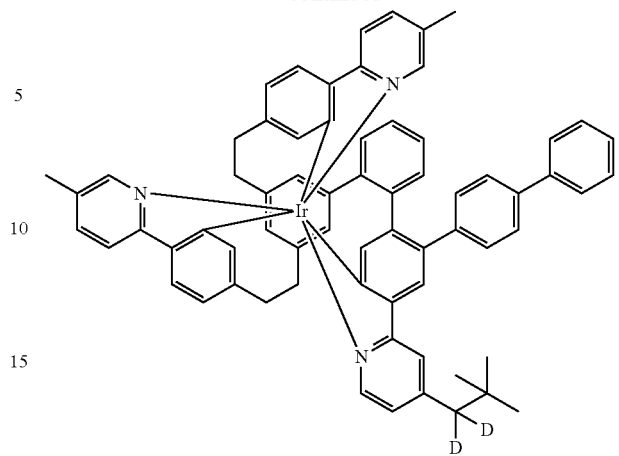
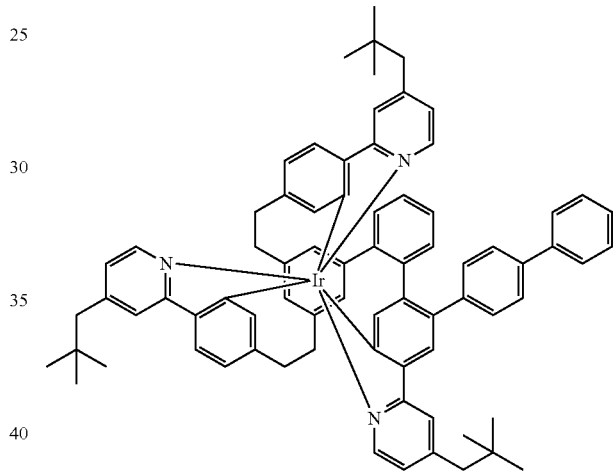
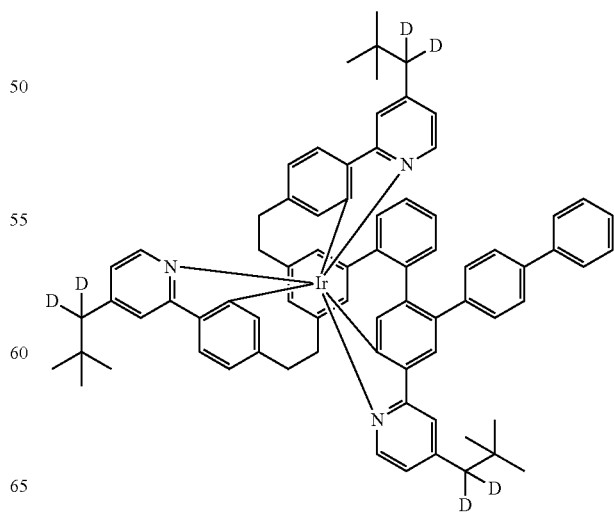

127
-continued
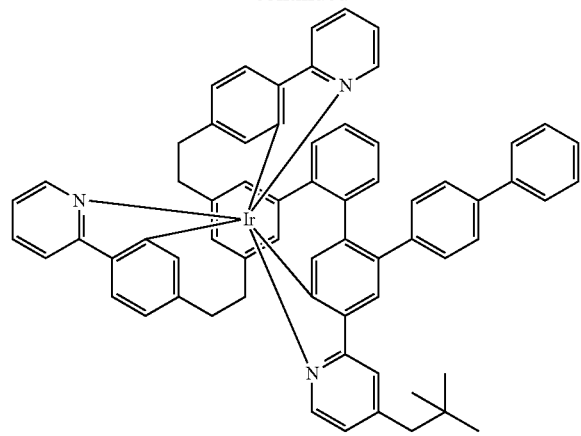
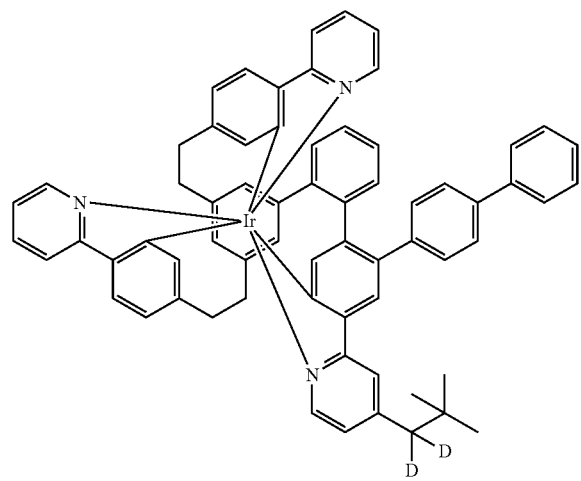
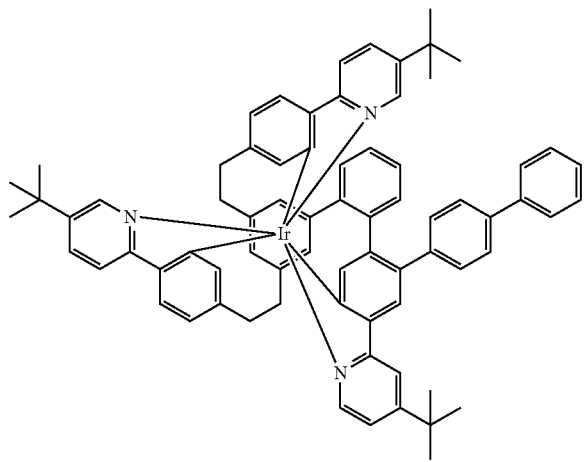
128
-continued
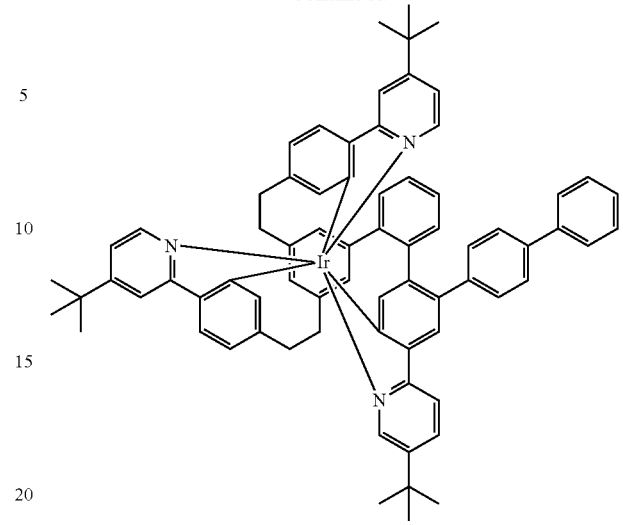
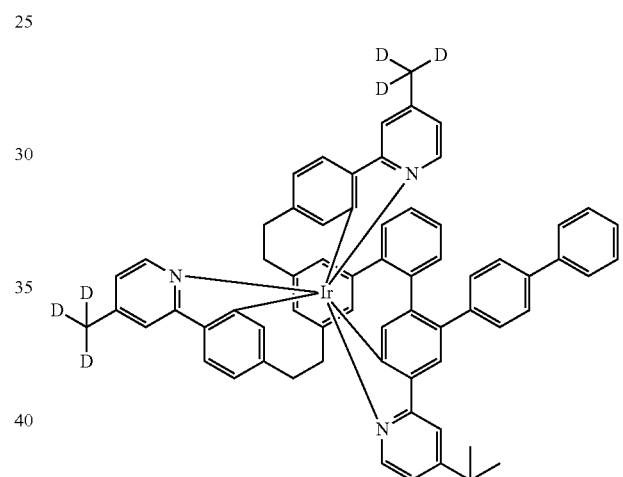
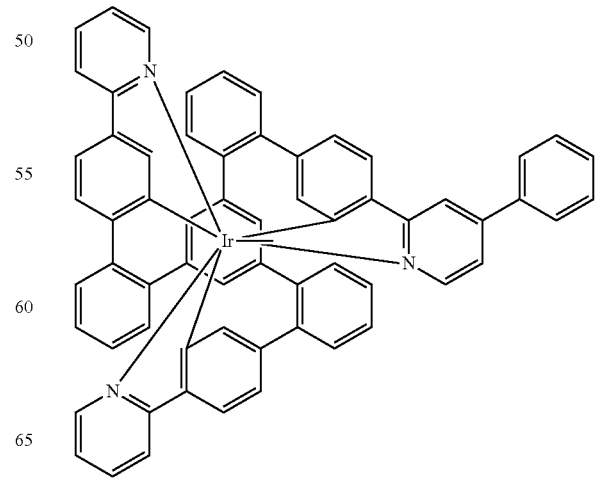

129
-continued
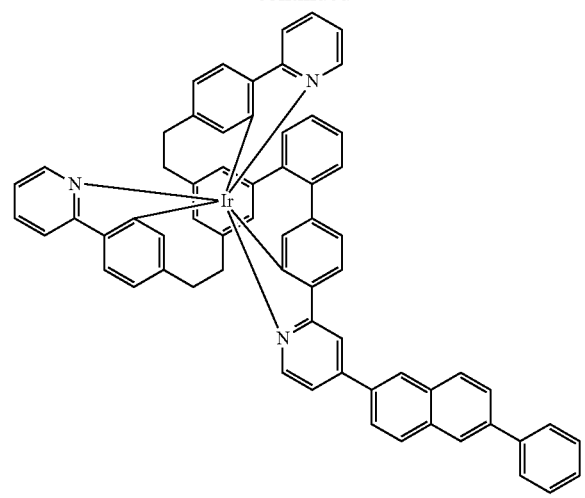
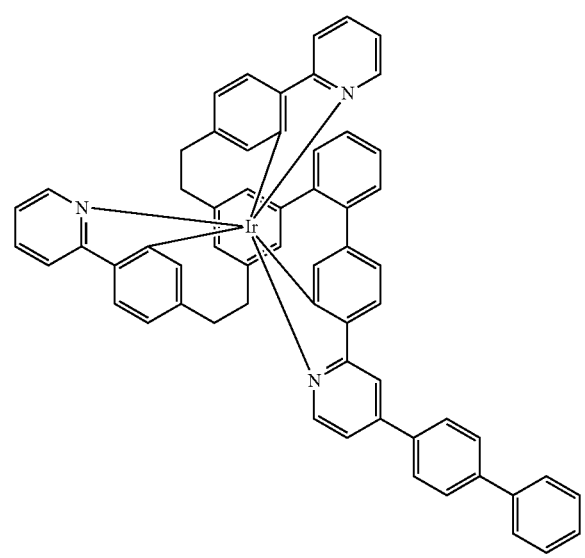
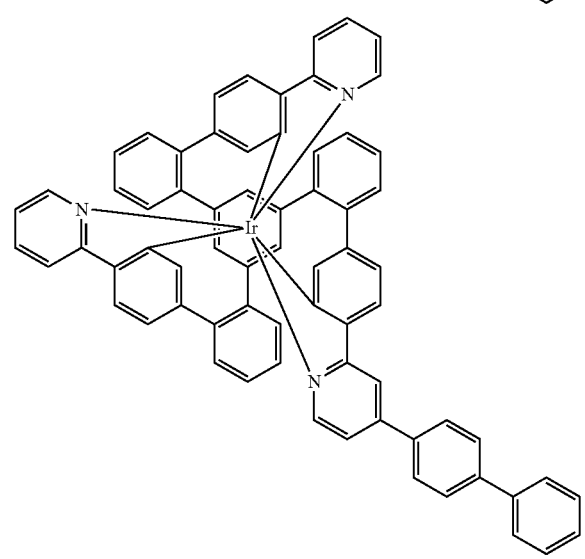
130
-continued
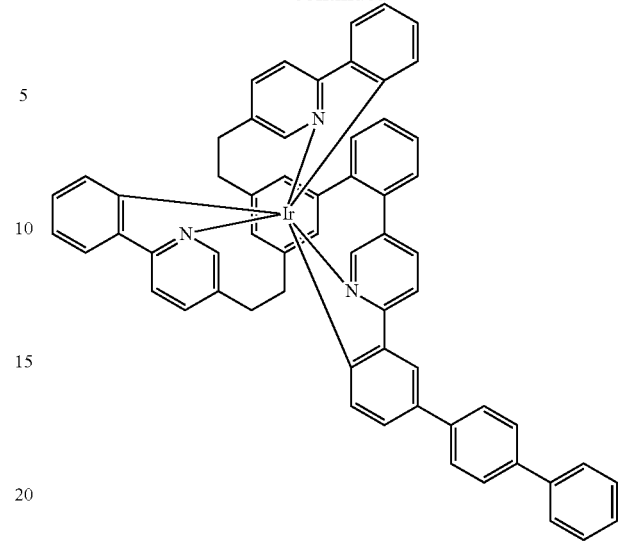
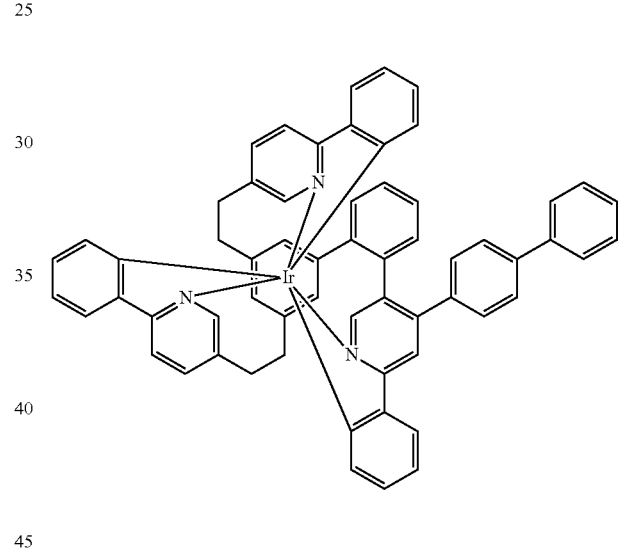
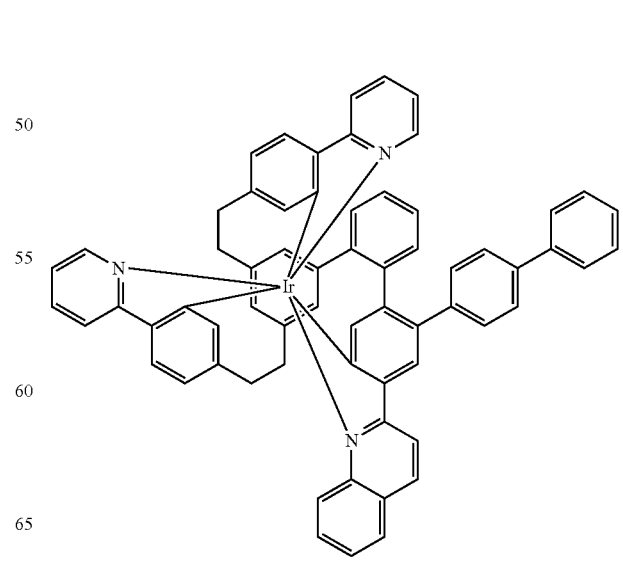

131
-continued
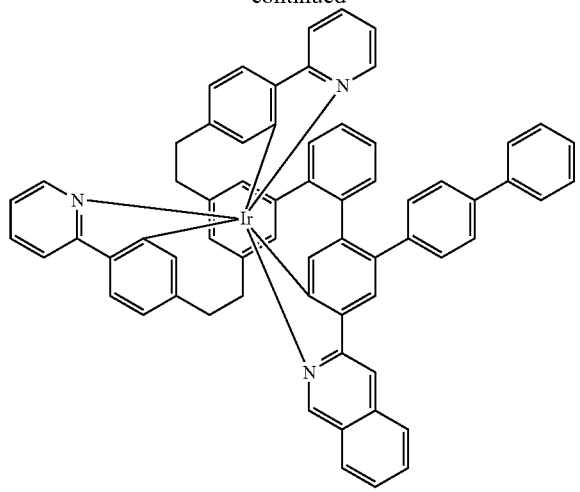
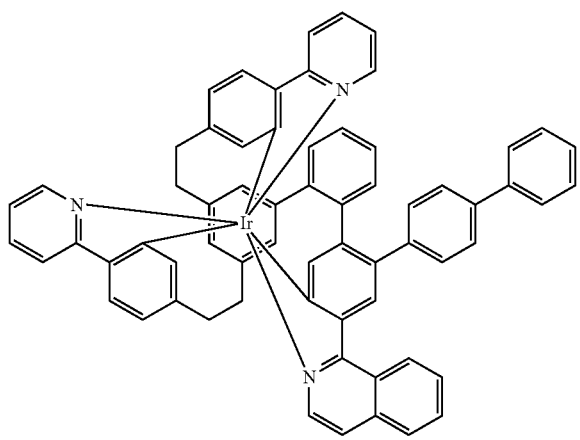
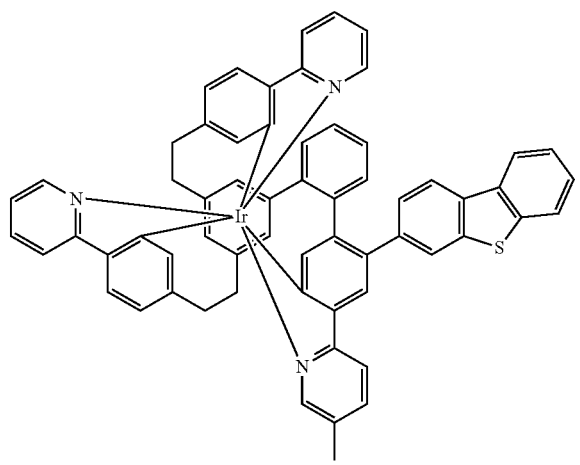
132
-continued
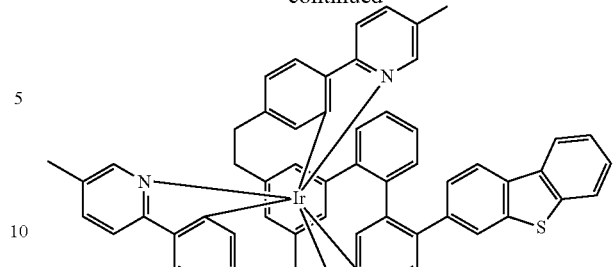
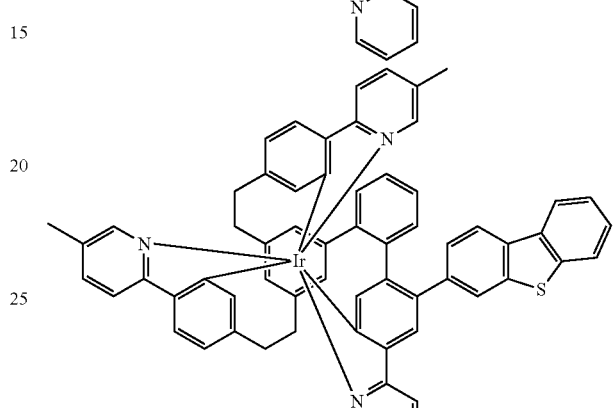
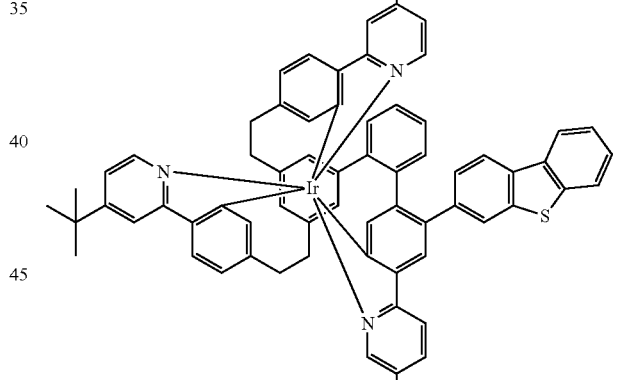
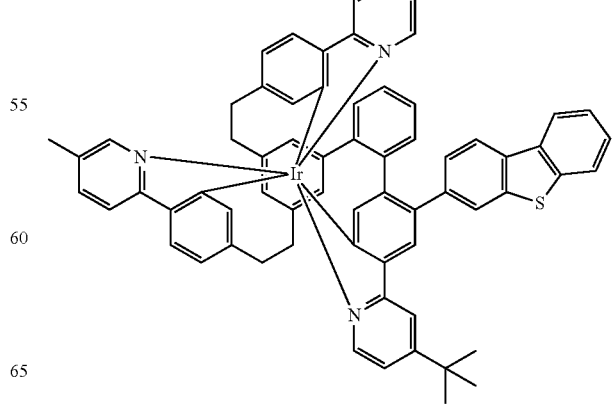

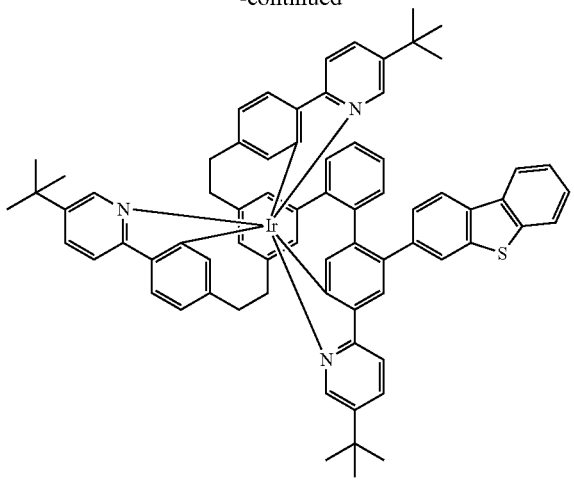

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (I) or the above-recited preferred embodiments.

Additionally preferred is an organic electroluminescent device, characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. However, it is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured.

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

In addition, hybrid methods are possible, in which, for example, one or more layers are applied from solution and one or more further layers are applied by vapor deposition.

Those skilled in the art are generally aware of these methods and are able to apply them without exercising inventive skill to organic electroluminescent devices comprising the compounds of the invention.

EXAMPLES

The syntheses which follow, unless stated otherwise, are conducted under a protective gas atmosphere. The reactants can be sourced from ALDRICH or ABCR (palladium(II) acetate, tri-o-tolylphosphine, inorganic materials, solvents).

The figures in the case of the reactants known from the literature are the CAS numbers.

a) 5-(3-phenylphenyl)quinoxalino[2,1-b]quinazoline-6,12-dione

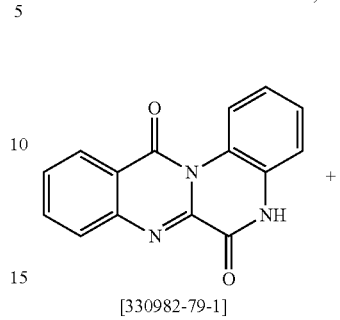

[330982-79-1]

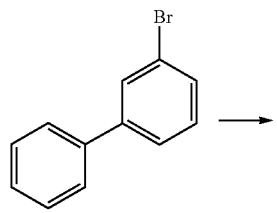

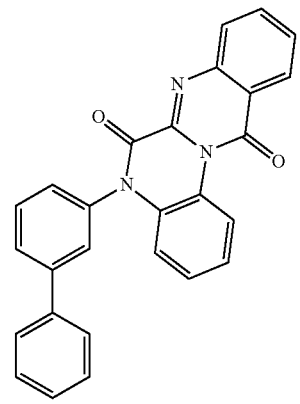

An initial charge of 6.6 g (24.8 mmol, 1.00 eq.) of 5H-quinoxalino[2,1-b]quinazoline-6,12-dione, 21.3 ml (128 mmol, 5.2 eq.) of 3-bromobiphenyl [2113-57-7] and 7.20 g of potassium carbonate (52.1 mmol, 2.10 eq.) in 220 ml of dry DMF is inertized under argon. Subsequently, 0.62 g (2.7 mmol, 0.11 eq) of 1,3-di(2-pyridyl)propane-1,3-dione and 0.52 g (2.7 mmol, 0.11 eq) of copper(I) iodide are added and the mixture is heated at 140° C. for three days. After the reaction has ended, the mixture is concentrated cautiously on a rotary evaporator, and the precipitated solids are filtered off with suction and washed with water and ethanol. The crude product is purified twice by means of a hot extractor (toluene/heptane 1:1), and the solids obtained are recrystallized from toluene. The yield after sublimation is 6.6 g (15 mmol), 60% of theory.

The following compounds are obtained in an analogous manner:

| Ex. | Reactant 1 | Reactant 1 | Product | Yield |
|---|---|---|---|---|
| 1a | [40078-06-6] | [83819-97-0] | | 56% |
| 2a | [40078-06-6] | [1009737-39-6] | | 52% |
| 3a | [500198-60-7] | [374077-23-3] | | 56% |
| 4a | [330982-79-1] | [502161-03-7] | | 60% |

-continued

| Ex. | Reactant 1 | Reactant 1 | Product | Yield |
|---|---|---|---|---|
| 5a | [40078-06-6] | [1692900-05-2] | | 57% |
| 6a | [40078-06-6] | [171408-76-7] | | 61% |
| 7a | [40078-06-6] | [1616881-55-0] | | 58% |

-continued

| Ex. | Reactant 1 | Reactant 1 | Product | Yield |
|---|---|---|---|---|
| 8a | [40078-06-6] | [1628067-38-8] | | 59% |
| 9a | [1416052-96-4] | [2305895-72-9] | | 66% |
| 10a | [1381841-93-5] | [2244026-83-1] | | 60% |

-continued
| Ex. | Reactant 1 | Reactant 1 | Product | Yield |
|---|---|---|---|---|
| 11a | 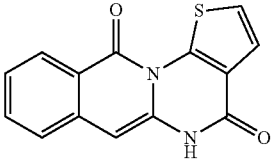<br>[1146577-90-3] | 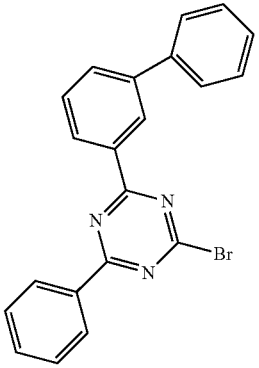<br>[2021249-67-0] | 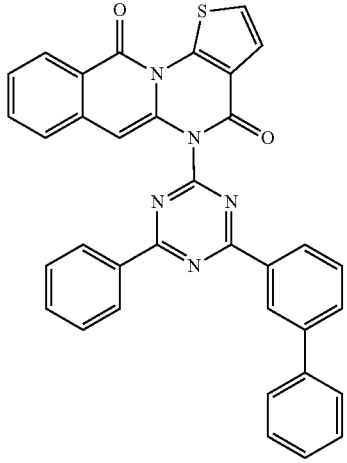 [SMILES: O=c1c2ccsc2n2c(=O)c3ccccc3cc2n1-c1nc(-c2ccccc2)nc(-c2cccc(-c3ccccc3)c2)n1] | 48% |
| 12a | 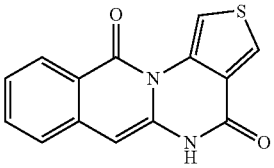<br>[1262629-30-0] | 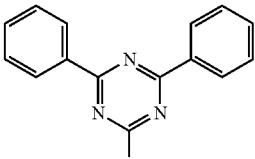<br>[80984-79-8] | 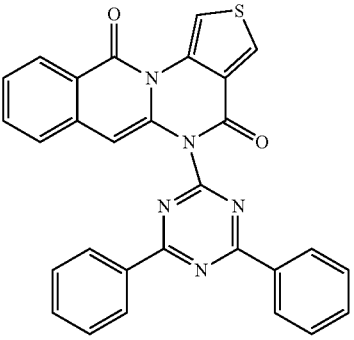 [SMILES: O=c1c2cscc2n2c(=O)c3ccccc3cc2n1-c1nc(-c2ccccc2)nc(-c2ccccc2)n1] | 54% |
| 13a | 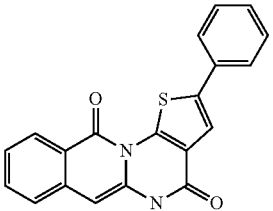<br>[380422-47-9] | <br>[80984-79-8] | 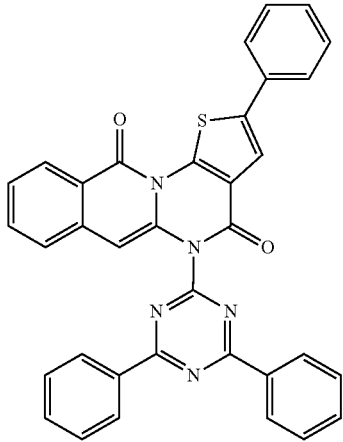 [SMILES: O=c1c2cc(-c3ccccc3)sc2n2c(=O)c3ccccc3cc2n1-c1nc(-c2ccccc2)nc(-c2ccccc2)n1] | 50% |
| 14a | 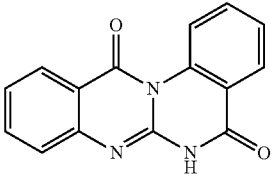<br>[40078-06-6] | 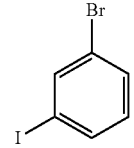 | 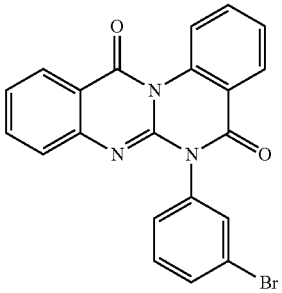 [SMILES: O=c1c2ccccc2n2c(=O)c3ccccc3nc2n1-c1cccc(Br)c1] | 53% |

-continued
| Ex. | Reactant 1 | Reactant 1 | Product | Yield |
|---|---|---|---|---|
| 15a | 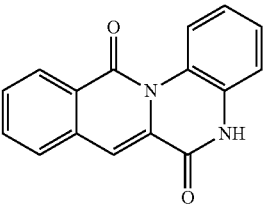 [330982-79-1] | 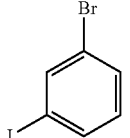 | 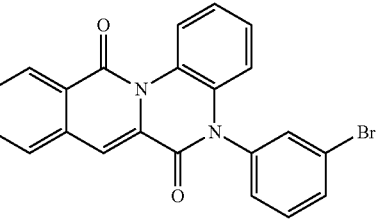 | 55% |
| 16a | 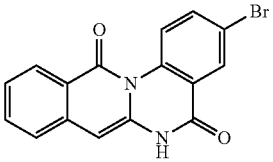 [683779-60-4] | 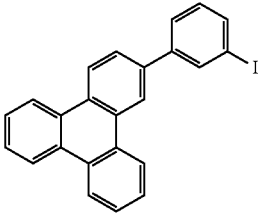 [1395888-84-2] | 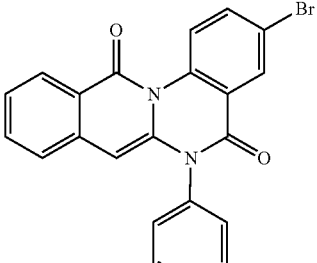 | 60% |
| 17a | 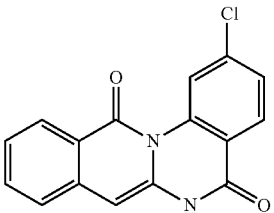 [889767-89-9] | 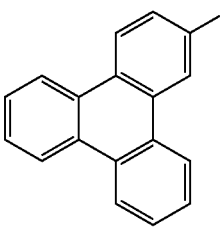 [1228778-59-3] | 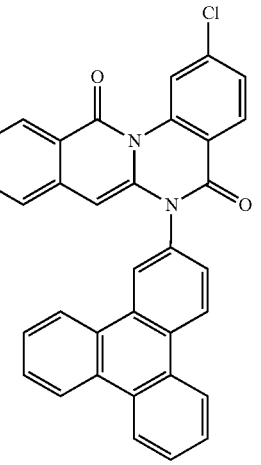 | 59% |
| 18a | 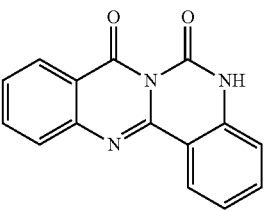 [19589-44-7] | 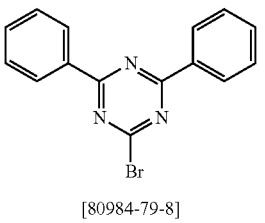 [SMILES: Brc1nc(-c2ccccc2)nc(-c2ccccc2)n1] [80984-79-8] | 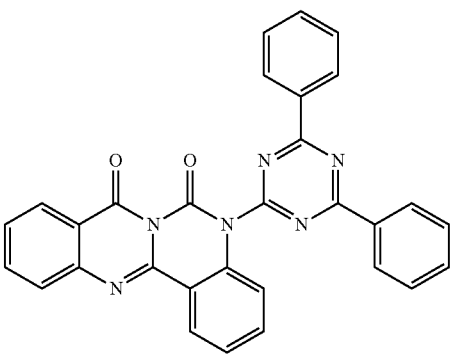 [SMILES: O=c1c2ccccc2nc2c3ccccc3n(-c3nc(-c4ccccc4)nc(-c4ccccc4)n3)c(=O)n12] | 63% |

-continued

| Ex. | Reactant 1 | Reactant 1 | Product | Yield |
|---|---|---|---|---|
| 19a | 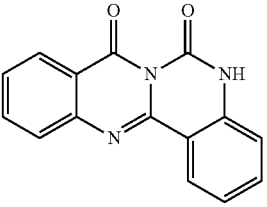 [19589-44-7] | 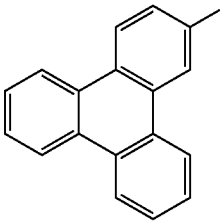 [1228778-59-3] | 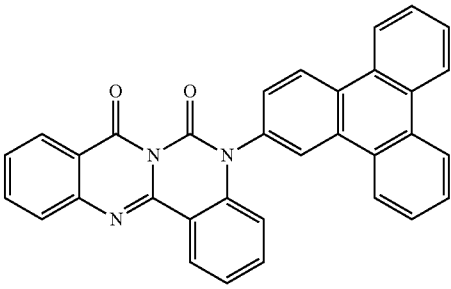 [SMILES: O=c1c2ccccc2nc2c3ccccc3n(-c3ccc4c5ccccc5c5ccccc5c4c3)c(=O)n12] | 60% |
| 20a | 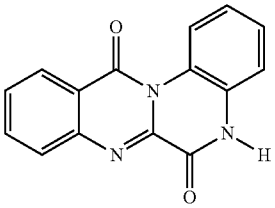 [330982-79-1] | 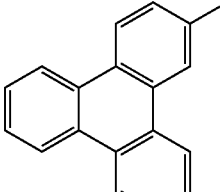 [1228778-59-3] | 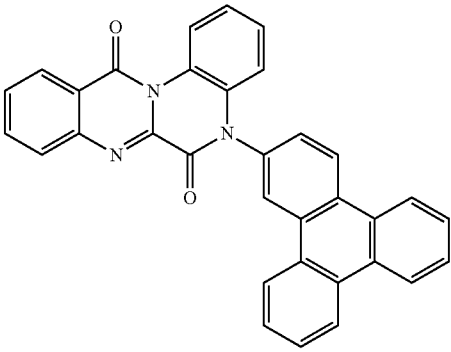 [SMILES: O=c1c2nc3ccccc3c(=O)n2c2ccccc2n1-c1ccc2c3ccccc3c3ccccc3c2c1] | 64% |
| 21a | 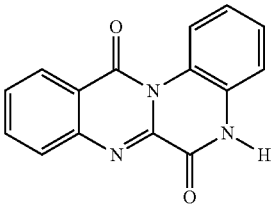 [330982-79-1] | 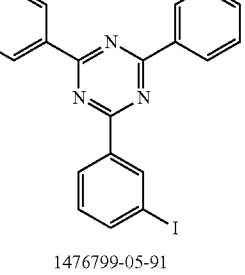 1476799-05-91 | 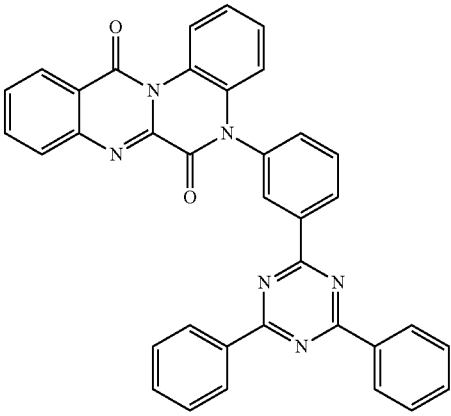 [SMILES: O=c1c2nc3ccccc3c(=O)n2c2ccccc2n1-c1cccc(-c2nc(-c3ccccc3)nc(-c3ccccc3)n2)c1] | 67% | b) 3-Bromo-6-phenyl-5H-quinazolino[3,2-a]quinazoline-5,12(6H)-dione

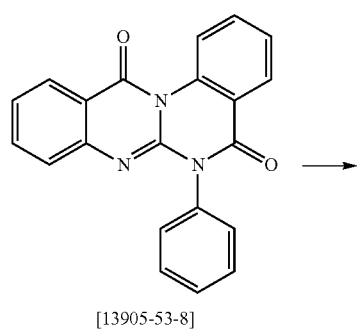

[13905-53-8]

-continued

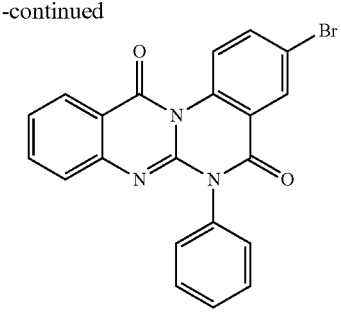

7.8 g (23 mmol) of 6-phenyl-5H-quinazolino[3,2-a]quinazoline-5,12(6H)-dione is additionally charged in 150 ml of DMF. Subsequently, a solution of 4 g (22.5 mmol) of NBS in 100 ml of DMF is added dropwise in the dark at room temperature, the mixture is allowed to come to room temperature and stirring is continued at this temperature for 4 h.

Subsequently, 150 ml of water are added to the mixture and extraction is effected with $CH_2Cl_2$. The organic phase is dried over $MgSO_4$ and the solvents are removed under reduced pressure. The product is subjected to extractive stirring with hot hexane and filtered off with suction. Yield: 7.7 g (18.4 mmol), 80% of theory, purity by $^1$H NMR about 97%.

The following compounds are obtained in an analogous manner:

| Ex. | Reactant 1 | Product | Yield |
|---|---|---|---|
| 1b | | | 85% |
| 2b | | | 79% | c) 6-Phenyl-3-(9-phenylcarbazol-3-yl)quinazolino[2,1-b]quinazoline-5,12-dione

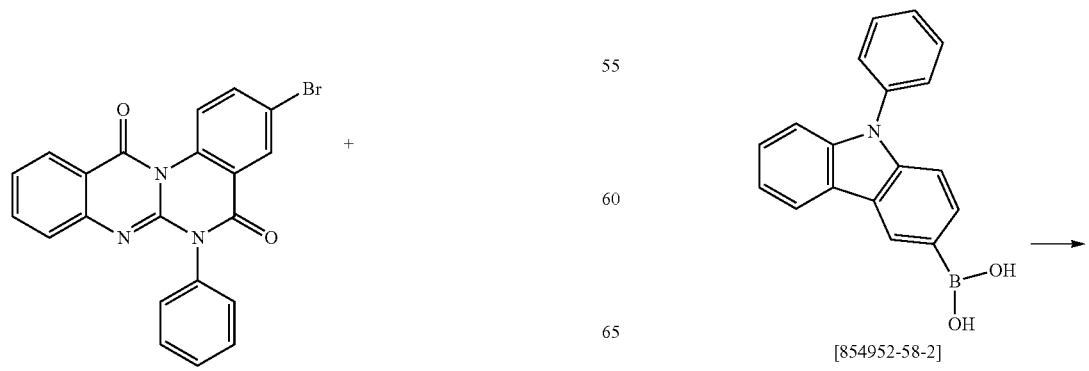

-continued

[854952-58-2]

-continued

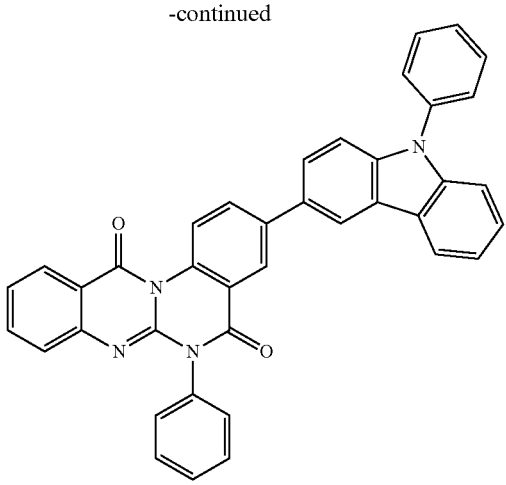

29.9 g (110.0 mmol) of triphenylene-2-boronic acid, 46 g (110.0 mmol) of 3-bromo-6-phenyl-5H-quinazolino[3,2-a]quinazoline-5,12(6H)-dione and 44.6 g (210.0 mmol) of tripotassium phosphate are suspended in 500 ml of toluene, 500 ml of dioxane and 500 ml of water. To this suspension are added 913 mg (3.0 mmol) of tri-o-tolylphosphine and then 112 mg (0.5 mmol) of palladium(II) acetate, and the reaction mixture is heated under reflux for 16 h. After cooling, the organic phase is removed, filtered through silica gel, washed three times with 200 ml each time of water and then concentrated to dryness. The residue is recrystallized from toluene and from dichloromethane/iso-propanol and finally sublimed under high vacuum; purity is 99.9%. The yield is 54 g (93 mmol), corresponding to 85% of theory.

The following compounds are obtained in an analogous manner:

-continued

| | Reactant 1 | Reactant 2 | Product | Yield |
|---|---|---|---|---|
| 3c | | [1612243-82-9] | | 67% |
| 4c | | [1251825-65-6] | | 80% |
| 5c | | [1266389-18-7] | | 60% |

-continued
| | Reactant 1 | Reactant 2 | Product | Yield |
|---|---|---|---|---|
| 6c | 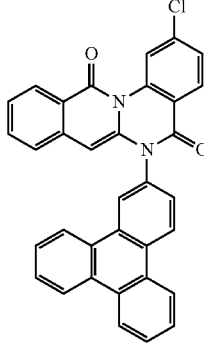 | 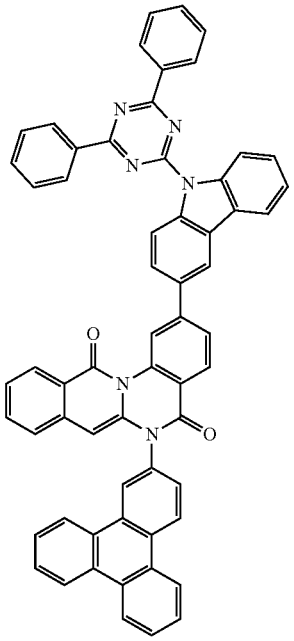 [SMILES: O=c1c2ccc(-c3ccc4c(c3)c3ccccc3n4-c3nc(-c4ccccc4)nc(-c4ccccc4)n3)cc2n2c(=O)c3ccccc3cc2n1-c1ccc2c3ccccc3c3ccccc3c2c1]\n[1266389-18-7] | 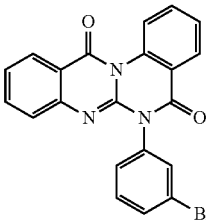 | 72% |
| 7c | 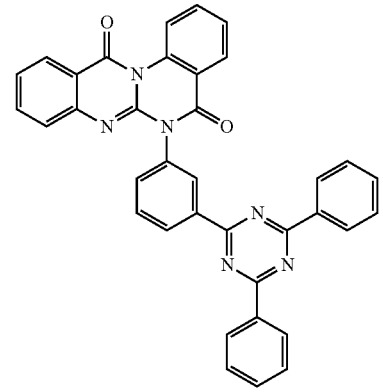 [SMILES: O=c1c2ccccc2n2c(=O)c3ccccc3nc2n1-c1cccc(-c2nc(-c3ccccc3)nc(-c3ccccc3)n2)c1] | 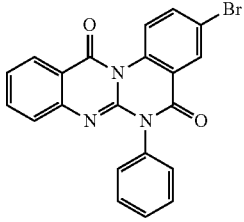 [SMILES: O=c1c2cc(Br)ccc2n2c(=O)c3ccccc3nc2n1-c1ccccc1]\n[1251825-65-6] | 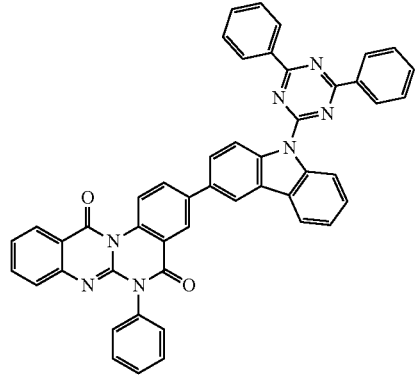 [SMILES: O=c1c2cc(-c3ccc4c(c3)c3ccccc3n4-c3nc(-c4ccccc4)nc(-c4ccccc4)n3)ccc2n2c(=O)c3ccccc3nc2n1-c1ccccc1] | 83% |
| 8c | | | | 75% |

-continued

| Reactant 1 | Reactant 2 | Product | Yield |
|---|---|---|---|
| 9c | [1642121-58-1] | | 71% |
| 10c | [1394815-87-2] | | 66% |
| 11c | [1394815-87-2] | | 69% |

-continued

| Reactant 1 | Reactant 2 | Product | Yield |
|---|---|---|---|
| 12c 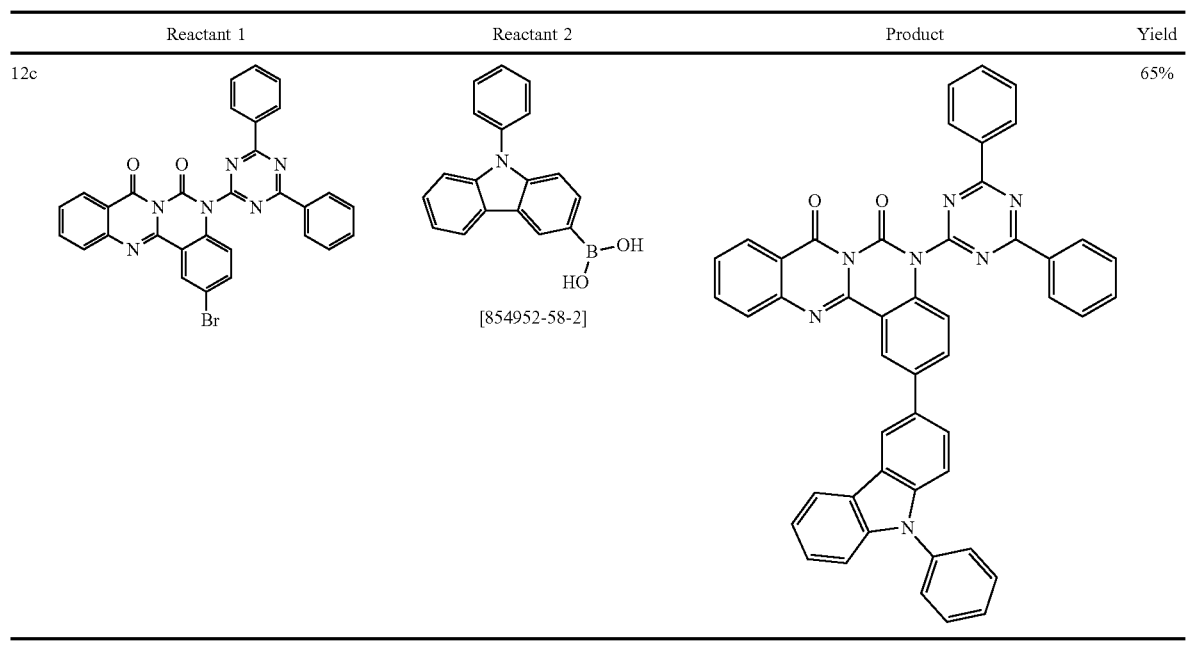 | | | 65% |

Production of the OLEDs

Examples E1 to E9 which follow (see table 1) present the use of the materials of the invention in OLEDs.

Pretreatment for Examples E1 to E9:

Glass plates coated with structured ITO (indium tin oxide) of thickness 50 nm are treated prior to coating with an oxygen plasma, followed by an argon plasma. These plasma-treated glass plates form the substrates to which the OLEDs are applied.

The OLEDs basically have the following layer structure: substrate/optional interlayer (IL)/hole injection layer (HIL)/ hole transport layer (HTL)/electron blocker layer (EBL)/ emission layer (EML)/optional hole blocker layer (HBL)/ electron transport layer (ETL)/optional electron injection layer (EIL) and finally a cathode. The cathode is formed by an aluminum layer of thickness 100 nm. The exact structure of the OLEDs can be found in table 1. The materials required for production of the OLEDs are shown in table 2. The data of the OLEDs are listed in tables 3 and 4.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC1:EG1:TEG1 (45%:45%:10%) mean here that the material 101 is present in the layer in a proportion by volume of 45%, EG1 in a proportion of 45% and TEG1 in a proportion of 10%. Analogously, the electron transport layer may also consist of a mixture of two materials.

The OLEDs are characterized in a standard manner. For this purpose, electroluminescence spectra, current efficiency (CE, measured in cd/A) and external quantum efficiency (EQE, measured in %) are determined as a function of luminance, calculated from current-voltage-luminance characteristics assuming Lambertian emission characteristics. Electroluminescence spectra are determined at a luminance of 1000 cd/m$^2$, and these are used to calculate the CIE 1931 x and y color coordinates. The results thus obtained can be found in table 3.

Use of the Materials of the Invention in OLEDs

The inventive compounds EG1 to EG7 can be used in examples E1 to E8 as matrix material in the emission layer of phosphorescent green OLEDs.

Table 4 summarizes the results of some examples. When the inventive compound EG7 is used as electron transport material, low voltage and good efficiency are obtained.

TABLE 1

Structure of the OLEDs

| Ex. | IL | HIL thickness | HTL thickness | EBL thickness | EML thickness | HBL thickness | ETL thickness | EIL thickness |
|---|---|---|---|---|---|---|---|---|
| E1 | | HATCN 5 nm | SpMA1 230 nm | SpMA2 20 nm | EG1:TEG1 (88%:12%) 40 nm | ST2 5 nm | ST2:LiQ (50%:50%) 30 nm | LiQ 1 nm |
| E2 | | HATCN 5 nm | SpMA1 230 nm | SpMA2 20 nm | EG2:TEG1 (88%:12%) 40 nm | ST2 5 nm | ST2:LiQ (50%:50%) 30 nm | LiQ 1 nm |
| E3 | | HATCN 5 nm | SpMA1 230 nm | SpMA2 20 nm | EG1:IC1:TEG1 (49%:44%:7%) 40 nm | ST2 5 nm | ST2:LiQ (50%:50%) 30 nm | LiQ 1 nm |
| E4 | | HATCN 5 nm | SpMA1 230 nm | SpMA2 20 nm | EG3:IC2:TEG1 (44%:44%:12%) 40 nm | ST2 5 nm | ST2:LiQ (50%:50%) 30 nm | LiQ 1 nm |
| E5 | | HATCN 5 nm | SpMA1 230 nm | SpMA2 20 nm | EG4:IC3:TEG1 (49%:44%:7%) 40 nm | ST2 5 nm | ST2:LiQ (50%:50%) 30 nm | LiQ 1 nm |

TABLE 1-continued

Structure of the OLEDs

| Ex. | IL | HIL thickness | HTL thickness | EBL thickness | EML thickness | HBL thickness | ETL thickness | EIL thickness |
|---|---|---|---|---|---|---|---|---|
| E6 |  | HATCN 5 nm | SpMA1 230 nm | SpMA2 20 nm | EG5:IC4:TEG1 (49%:44%:7%) 40 nm | ST2 5 nm | ST2:LiQ (50%:50%) 30 nm | LiQ 1 nm |
| E7 |  | HATCN 5 nm | SpMA1 230 nm | SpMA2 20 nm | EG6:IC1:TEG1 (49%:44%:7%) 40 nm | ST2 5 nm | ST2:LiQ (50%:50%) 30 nm | LiQ 1 nm |
| E8 |  | HATCN 5 nm | SpMA1 230 nm | SpMA2 20 nm | EG7:IC1:TEG1 (49%:44%:7%) 40 nm | ST2 5 nm | ST2:LiQ (50%:50%) 30 nm | LiQ 1 nm |
| E9 | SpA1 70 nm |  | HATCN 5 nm | SpMA1 90 nm | IC1:TEG1 (90%:10%) 30 nm | — | EG7:LiQ (50%:50%) 40 nm |  |

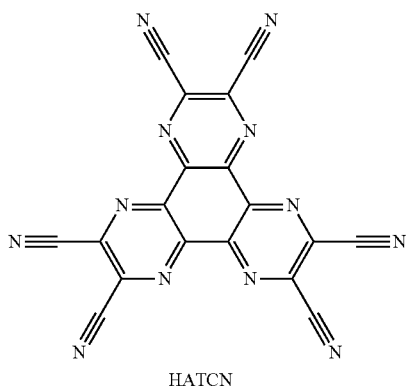

HATCN

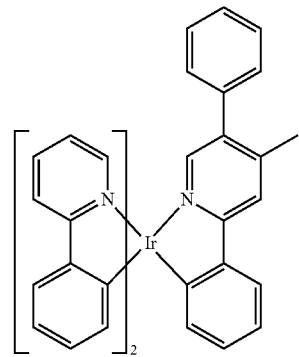

TEG1

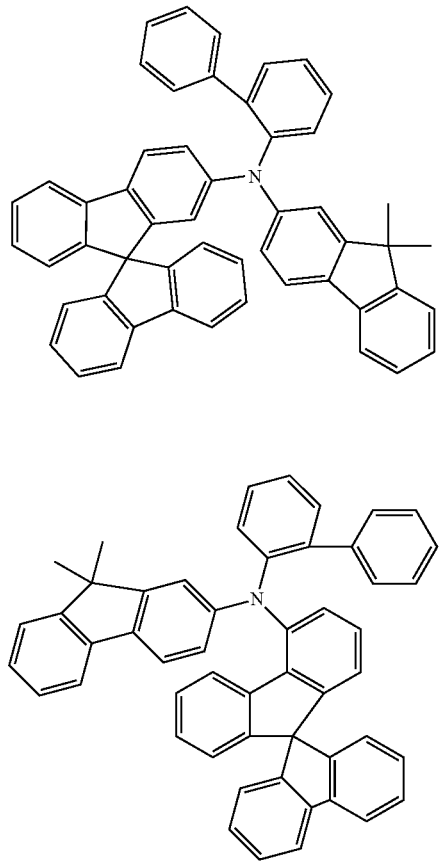

SpMA1

SpMA2

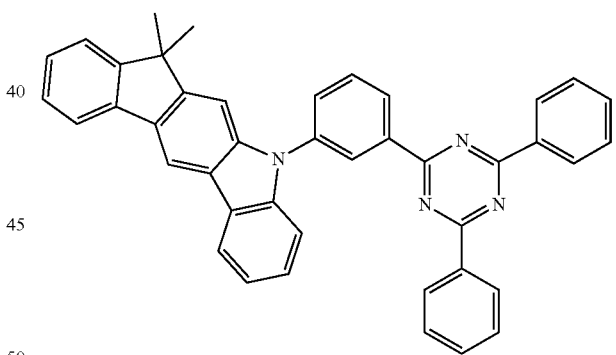

IC1

IC2

-continued
IC3
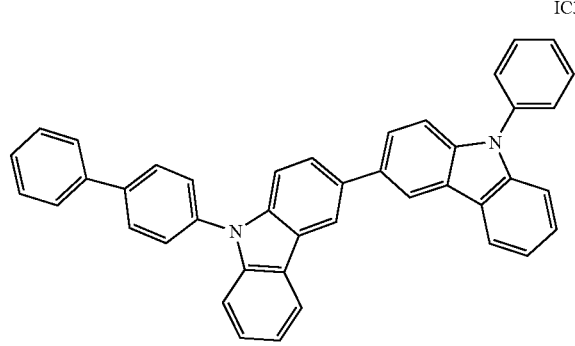
IC4
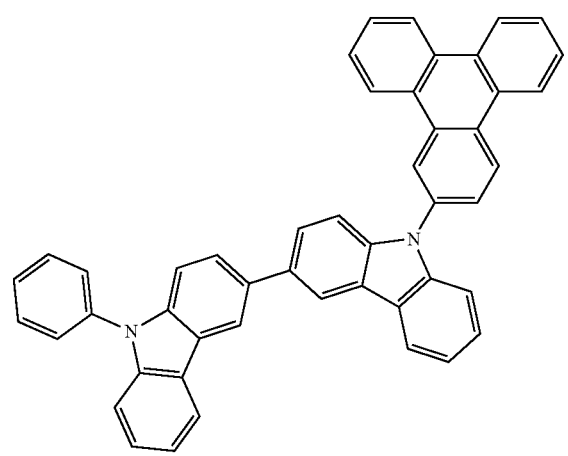
ST2
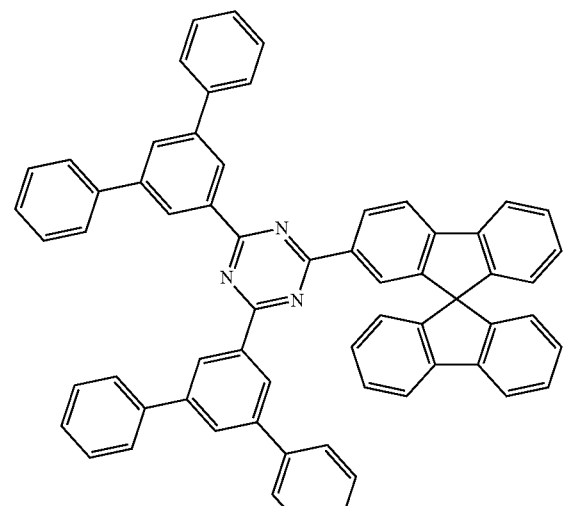
LiQ
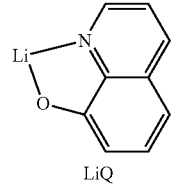
-continued
SpA1
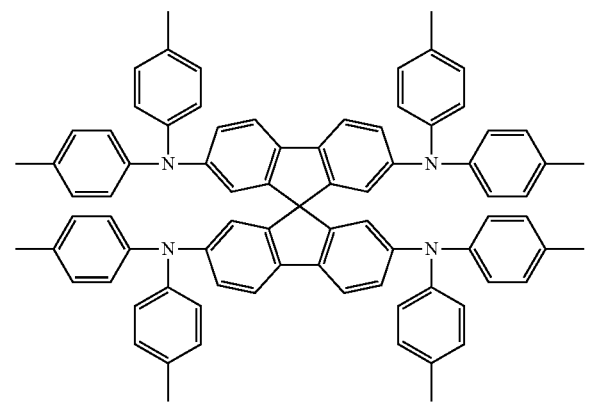
EG1(1C)
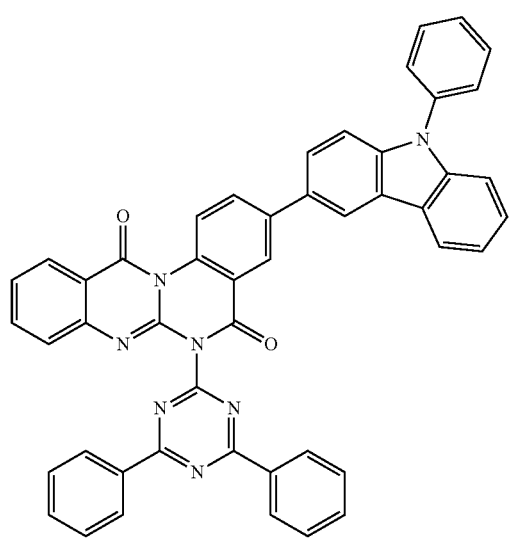
EG2 (6c)
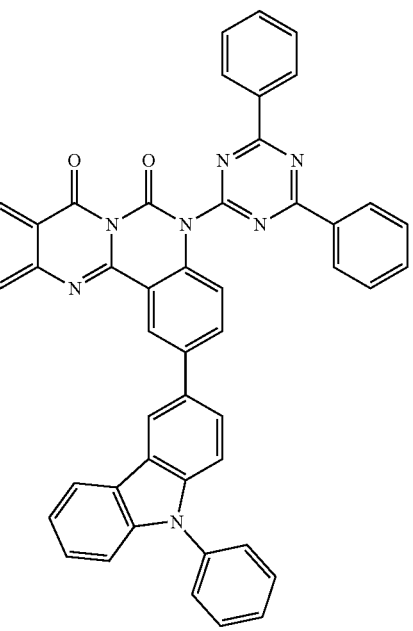

EG3 (1a)
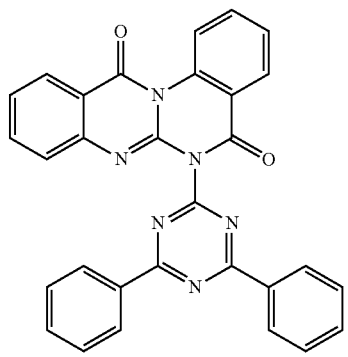
EG4 (3a)
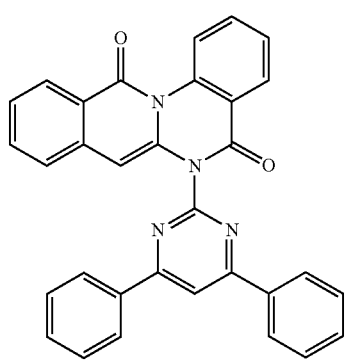
EG5 (18a)
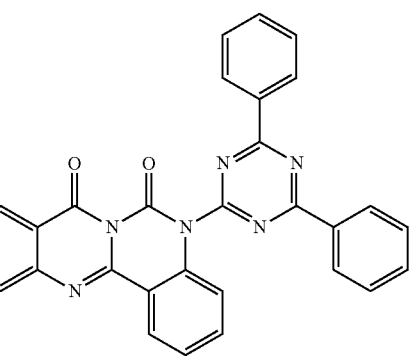
EG6 (4c)
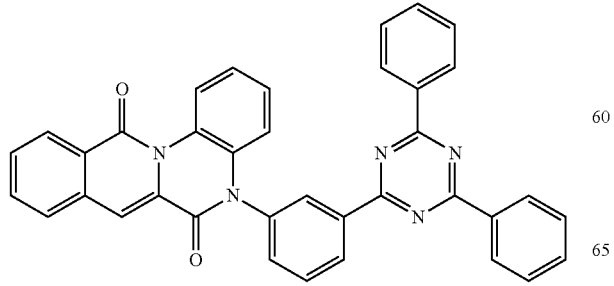
EG7 (7c)
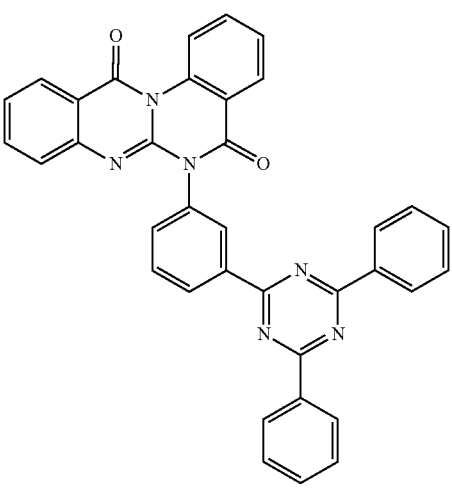
TABLE 3
Data of the OLEDs
| Ex. | U1000 (V) | SE1000 (cd/A) | EQE 1000 (%) | CIE x/y at 1000 cd/m$^2$ |
|---|---|---|---|---|
| E1 | 3.6 | 71 | 15 | 0.35/0.61 |
| E2 | 3.8 | 68 | 17 | 0.34/0.62 |
| E3 | 3.2 | 67 | 17 | 0.35/0.61 |
| E4 | 3.1 | 72 | 15.5 | 0.35/0.60 |
| E5 | 3.1 | 68 | 16 | 0.34/0.62 |
| E6 | 3.2 | 67 | 17 | 0.35/0.61 |
| E7 | 3.1 | 72 | 18 | 0.35/0.62 |
| E8 | 3.1 | 68 | 18 | 0.34/0.61 |
TABLE 4
Data of the OLEDs
| Ex. | U1000 (V) | CE1000 (cd/A) | PE1000 (lm/W) | EQE 1000 (%) | CIE x/y at 1000 cd/m$^2$ |
|---|---|---|---|---|---|
| E9 | 3.7 | 62 | 51 | 17 | 0.31/0.64 |
The invention claimed is:
1. A compound according to one of the formulae (IV) to (VI)
Formula (IV)
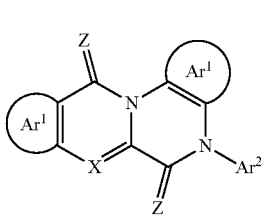

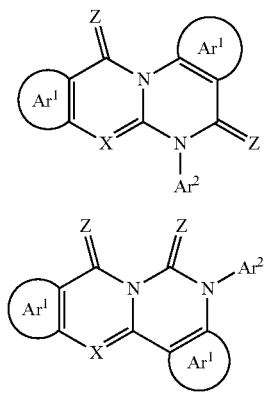

Formula (V)

Formula (VI)

and where the variables that occur are as follows:

X is N or CAr³;

Z is O;

Ar¹ is the same or different at each instance and is selected from fused-on aromatic ring systems having 6 to 18 aromatic ring atoms; where the aromatic ring systems are each substituted by R¹ radicals;

Ar² is selected from phenyl, pyridine, naphthalene, triphenylene, carbazole, pyrimidine, triazine, triazinylphenylene and biphenyl, each substituted by one or more R² radicals;

Ar³ is selected from H, D, and aromatic ring systems having 6 to 40 aromatic ring atoms; where the aromatic ring systems are each substituted by R³ radicals;

R¹ is the same or different at each instance and is selected from H, D, aromatic ring systems having 6 to 40 aromatic ring atoms, and heteroaromatic ring systems having 5 to 40 aromatic ring atoms; where the aromatic ring systems and heteroaromatic ring systems mentioned are each substituted by R⁴ radicals;

R² is the same or different at each instance and is selected from H, D, aromatic ring systems having 6 to 40 aromatic ring atoms, and heteroaromatic ring systems having 5 to 40 aromatic ring atoms; where the aromatic ring systems and heteroaromatic ring systems mentioned are each substituted by R⁴ radicals;

R³ is the same or different at each instance and is selected from H, and D;

R⁴ is the same or different at each instance and is selected from H, and D, and;

excluding the following compounds:

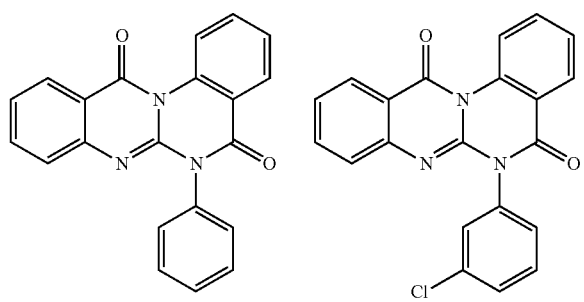

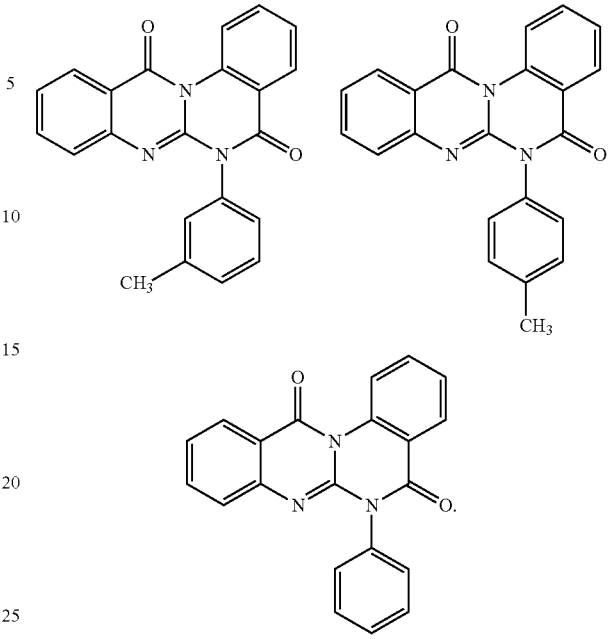

2. The compound as claimed in claim 1, wherein X is N.

3. The compound as claimed in claim 1, wherein Ar¹ is the same or different at each instance and is selected from #phenyl, naphthalene, phenanthrene, anthracene: where the aromatic ring systems are each substituted by R¹ radicals.

4. The compound as claimed in claim 1, wherein Ar² is selected from each substituted by R² radicals.

5. The compound as claimed in claim 1, wherein the compound conforms to one of the formulae (X) and (XI):

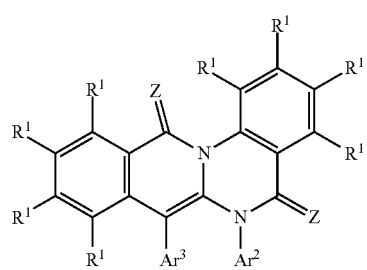

Formula (X)

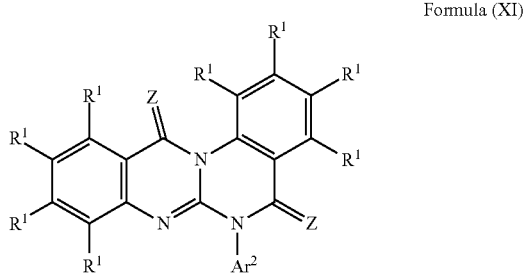

Formula (XI)

where the variables are as defined in claim 1.

6. A process for preparing the compound as claimed in claim 1, comprising preparing first an intermediate of one of the formulae (IV-Int) to (VI-Int)

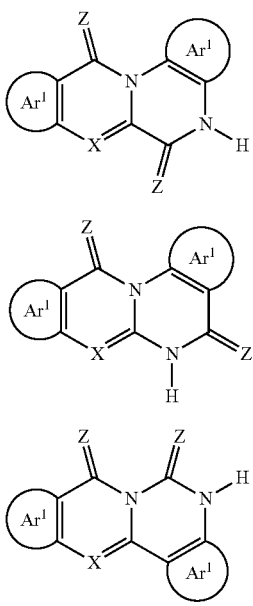

Formula (IV-Int)

Formula (V-Int)

Formula (VI-Int)

by a ring closure reaction,
introducing in an Ullmann reaction or a Buchwald reaction an aromatic or heteroaromatic system in the position of the Ar² group in the formulae (IV) to (VI), and conducting a halogenation reaction on one of the Ar¹ rings, which introduces a halogen substituent in one of the Ar¹ rings, and then conducting a Suzuki reaction in which an aromatic system is introduced in the position of the halogen substituent.

7. A formulation comprising a compound according to one of the formulae (IV) to (VI)

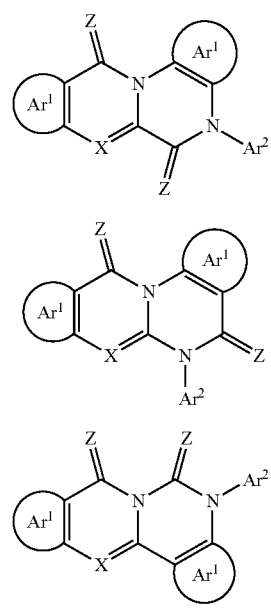

Formula (IV)

Formula (V)

Formula (VI)

and where the variables that occur are as follows:

X is N or $CAr^3$;

Z is O;

$Ar^1$ is the same or different at each instance and is selected from fused-on aromatic ring systems having 6 to 18 aromatic ring atoms, where the aromatic ring systems are each substituted by $R^1$ radicals;

$Ar^2$ is selected from phenyl, pyridine, naphthalene, triphenylene, carbazole, pyrimidine, triazine, triazinylphenylene and biphenyl, each substituted by one or more $R^2$ radicals;

$Ar^3$ is selected from H, D and aromatic ring systems having 6 to 40 aromatic ring atoms; where the aromatic ring systems are each substituted by $R^3$ radicals;

$R^1$ is the same or different at each instance and is selected from H, D, aromatic ring systems having 6 to 40 aromatic ring atoms, and heteroaromatic ring systems having 5 to 40 aromatic ring atoms; where the aromatic ring systems and heteroaromatic ring systems mentioned are each substituted by $R^4$ radicals;

$R^2$ is the same or different at each instance and is selected from H, D, E, aromatic ring systems having 6 to 40 aromatic ring atoms, and heteroaromatic ring systems having 5 to 40 aromatic ring atoms; where the aromatic ring systems and heteroaromatic ring systems mentioned are each substituted by $R^4$ radicals;

$R^3$ is the same or different at each instance and is selected from H, and D;

$R^4$ is the same or different at each instance and is selected from H, and D, and excluding the following compound:

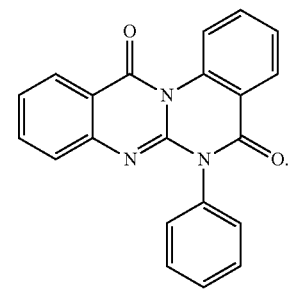 [SMILES: O=c1c2ccccc2n2c(=O)c3ccccc3nc2n1-c1ccccc1]

8. A method comprising utilizing the compound according to one of the formula (IV) to (VI) as defined in claim 7 in an electronic device.

9. An electronic device comprising at least one compound according to one of the formulae (IV) to (VI) as defined in claim 7.

10. The electronic device as claimed in claim 9, wherein the device is an organic electroluminescent device, and wherein the compound is used in an emitting layer as matrix material for one or more phosphorescent emitters or for emitters that exhibit TADF (thermally activated delayed fluorescence), and/or is used in an electron transport layer and/or is used in a hole blocker layer.

* * * * *